US012773423B2

(12) United States Patent
Matray et al.

(10) Patent No.: US 12,773,423 B2
(45) Date of Patent: Oct. 27, 2026

(54) AUTOMATED SYNTHESIS OF POLYMERIC DUAL DRUGS

(71) Applicant: SONY GROUP CORPORATION, Tokyo (JP)

(72) Inventors: Tracy Matray, Snohomish, WA (US); Michael VanBrunt, Bothell, WA (US); John Michael McCutcheon, Shoreline, WA (US)

(73) Assignee: Sony Group Corporation, Tokyo (JP)

( * ) Notice: Subject to any disclaimer, the term of this patent is extended or adjusted under 35 U.S.C. 154(b) by 177 days.

(21) Appl. No.: 18/695,674

(22) PCT Filed: Sep. 27, 2022

(86) PCT No.: PCT/IB2022/059149

§ 371 (c)(1),
(2) Date: Mar. 26, 2024

(87) PCT Pub. No.: WO2023/052971

PCT Pub. Date: Apr. 6, 2023

(65) Prior Publication Data

US 2025/0009786 A1 Jan. 9, 2025

Related U.S. Application Data

(60) Provisional application No. 63/253,071, filed on Oct. 6, 2021, provisional application No. 63/250,913, filed on Sep. 30, 2021.

(51) Int. Cl.

*A61K 31/80* (2006.01)
*A61K 47/68* (2017.01)
*C08G 65/00* (2006.01)

(52) U.S. Cl.

CPC .......... *A61K 31/80* (2013.01); *A61K 47/6835* (2017.08); *C08G 65/00* (2013.01)

(58) Field of Classification Search

None

See application file for complete search history.

(56) References Cited

U.S. PATENT DOCUMENTS

| | | |
|---|---|---|
| 4,450,305 A | 5/1984 | Kamhi |
| 4,476,229 A | 10/1984 | Fino et al. |

(Continued)

FOREIGN PATENT DOCUMENTS

| | | |
|---|---|---|
| CA | 2263671 A1 | 2/1998 |
| CN | 102174078 A | 9/2011 |

(Continued)

OTHER PUBLICATIONS

"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j0I5.3231j0j7&s . . . 2 pages.

(Continued)

*Primary Examiner* — Dominic Lazaro

(74) *Attorney, Agent, or Firm* — Seed Intellectual Property Law Group LLP

(57) ABSTRACT

Compounds useful as biologically active compounds with or without fluorescent or colored dyes are disclosed. In some embodiments, the compounds have the following structure (I): (I) or a stereoisomer, tautomer or salt thereof, wherein $R^1$, $R^2$, $R^3$, $R^4$, $R^5$, $R^6$, $R^7$, $L^1$, $L^2$, $L^3$, $L^4$, $L^5$, $L^6$, $L^7$, $L^8$, $L^9$, $L^{10}$, $L^{11}$, $M^1$, $M^2$, $M^3$, l, m, n, p, and q are as defined herein. Additional compound, methods of preparation, pharmaceutical compositions, and methods of treatment related to compounds of Structure (I) are also provided.

(Continued)

(I)

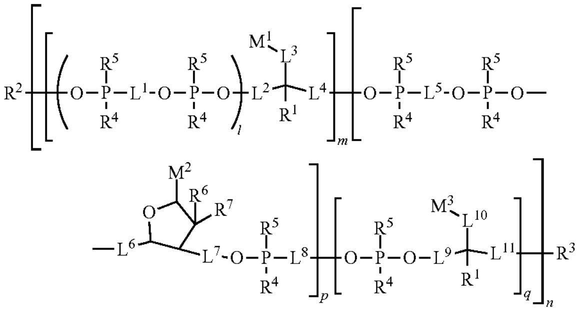

20 Claims, 2 Drawing Sheets

(56) References Cited

U.S. PATENT DOCUMENTS 4,778,753 A 10/1988 Yamanishi et al.
5,053,054 A 10/1991 Kirchanski
5,268,486 A 12/1993 Waggoner et al.
5,318,894 A 6/1994 Pugia
5,582,977 A 12/1996 Yue et al.
5,698,391 A 12/1997 Cook et al.
5,886,177 A 3/1999 Cook et al.
5,994,143 A 11/1999 Bieniarz et al.
6,005,093 A 12/1999 Wood et al.
6,140,480 A 10/2000 Kool
6,171,859 B1 1/2001 Herrnstadt et al.
6,218,108 B1 4/2001 Kool
6,365,730 B1 4/2002 Jennings et al.
6,380,431 B1 4/2002 Whipple et al.
6,479,650 B1 11/2002 Kool
6,514,700 B1 2/2003 Singh
6,534,041 B1 3/2003 Licha et al.
6,627,400 B1 9/2003 Singh et al.
6,670,193 B2 12/2003 Kool
6,716,452 B1 4/2004 Piccariello et al.
6,852,709 B2 2/2005 Leong et al.
7,038,063 B2 5/2006 Lee et al.
7,060,708 B2 6/2006 Piccariello et al.
7,172,907 B2 2/2007 Chen et al.
7,423,133 B2 9/2008 Kool et al.
7,667,024 B2 2/2010 Mao et al.
7,897,684 B2 3/2011 Bazan et al.
8,008,522 B2 8/2011 Lukhtanov et al.
8,101,776 B2 1/2012 Berens et al.
8,153,706 B2 4/2012 Vasudevan
8,217,389 B2 7/2012 Nakano et al.
8,293,700 B2 10/2012 Arranz
8,349,308 B2 1/2013 Yurkovetskiy et al.
8,354,515 B2 1/2013 Ueno et al.
8,431,545 B2 4/2013 Kataoka et al.
8,491,993 B2 7/2013 Nguyen et al.
8,546,590 B2 10/2013 Gall
8,632,947 B2 1/2014 Bentley et al.
8,802,738 B2 8/2014 Emrick
8,895,023 B2 11/2014 Rademacher et al.
8,906,603 B2 12/2014 Castro et al.
8,946,394 B2 2/2015 Na et al.
9,029,537 B2 5/2015 Koch
9,085,799 B2 7/2015 Bazan et al.
9,150,782 B2 10/2015 Lee et al.
9,400,273 B1 7/2016 Liu et al.
9,545,447 B2 1/2017 Wooley et al.
9,649,389 B2 5/2017 Groves et al.
9,687,291 B2 6/2017 Shimizu et al.
9,689,877 B2 6/2017 Matray et al.
9,696,310 B2 7/2017 Margulies et al.
9,714,946 B2 7/2017 Bradner et al.
9,765,220 B2 9/2017 Matray et al.
9,822,134 B2 11/2017 Segev
9,851,359 B2 12/2017 Matray et al.
9,884,070 B2 2/2018 Denardo et al.
9,910,051 B2 3/2018 Beacham et al.
9,913,992 B2 3/2018 Demarest et al.
9,932,578 B2 4/2018 Feinstein et al.
9,939,454 B2 4/2018 Dzubay et al.
10,036,754 B2 7/2018 Matray et al.
10,191,060 B2 1/2019 Chiu et al.
10,435,563 B2 10/2019 Matray et al.
10,617,670 B2 4/2020 Sapra et al.
10,709,791 B2 7/2020 Stayton et al.
10,834,091 B2 11/2020 Deninno et al.
10,865,310 B2 12/2020 Matray et al.
10,866,244 B2 12/2020 Matray et al.
10,954,391 B2 3/2021 Matray et al.
10,989,715 B2 4/2021 Matray et al.
11,013,756 B2 5/2021 Haruta et al.
11,084,932 B2 8/2021 Battrell et al.
11,142,647 B2 10/2021 Matray et al.
11,312,736 B1 4/2022 Matray et al.
11,352,502 B2 6/2022 Matray et al.
11,370,922 B2 6/2022 Matray et al.
11,377,563 B2 7/2022 Matray et al.
11,390,754 B2 7/2022 Singh et al.
11,434,374 B2 9/2022 Matray et al.
11,434,377 B2 9/2022 Matray et al.
11,453,783 B2 9/2022 Matray et al.
11,618,906 B2 4/2023 Steele et al.
11,685,835 B2 6/2023 Matray
11,827,661 B2 11/2023 Battrell et al.
11,874,280 B2 1/2024 Jackson et al.
11,931,419 B2 3/2024 Matray
11,945,955 B2 4/2024 Matray et al.
2001/0018503 A1 8/2001 Whipple et al.
2002/0012947 A1 1/2002 Bevers et al.
2002/0099013 A1 7/2002 Piccariello et al.
2002/0142329 A1 10/2002 Matray et al.
2003/0054361 A1 3/2003 Heller
2003/0207208 A1 11/2003 Uenishi
2003/0207264 A1 11/2003 Packard et al.
2004/0014981 A1 1/2004 Lugade et al.
2004/0067498 A1 4/2004 Chenna et al.
2004/0096825 A1 5/2004 Chenna et al.
2004/0138467 A1 7/2004 French et al.
2004/0224372 A1 11/2004 Li et al.
2004/0241768 A1 12/2004 Whitten et al.
2005/0054024 A1 3/2005 Lawrence
2005/0123935 A1 6/2005 Haugland et al.
2006/0008822 A1 1/2006 Manoharan et al.
2006/0035302 A1 2/2006 Lee
2006/0063186 A1 3/2006 Benson et al.
2007/0042398 A1 2/2007 Peng et al.
2007/0077549 A1 4/2007 Buller et al.
2007/0148094 A1 6/2007 Uzgiris
2007/0269902 A1 11/2007 Beechem et al.
2008/0227939 A1 9/2008 Mizoshita et al.
2009/0253792 A1 10/2009 Mickle et al.
2009/0299070 A1 12/2009 Berens et al.
2010/0039684 A1 2/2010 Kolb et al.
2010/0092386 A1 4/2010 Segev
2010/0129800 A1 5/2010 Aymami Bofarull et al.
2010/0192312 A1 8/2010 Cremer et al.
2011/0144065 A1 6/2011 Denardo et al.
2011/0224516 A1 9/2011 Romey et al.
2012/0021454 A1 1/2012 Bikker et al.
2012/0116079 A1 5/2012 Lukhtanov et al.
2012/0126175 A1 5/2012 Ueno et al.
2013/0059343 A1 3/2013 Cheung
2013/0119363 A1 5/2013 Sasaki et al.
2013/0137755 A1 5/2013 Segev
2013/0202536 A1 8/2013 Mustaev et al.
2013/0244891 A1 9/2013 Waggoner et al.
2014/0023590 A1 1/2014 Gao et al.
2014/0193504 A1 7/2014 Wooley et al.
2014/0275508 A1 9/2014 Scarr et al.

(56) References Cited

U.S. PATENT DOCUMENTS

| | | | |
|---|---|---|---|
| 2015/0030541 A1 | 1/2015 | Rogers | |
| 2015/0110715 A1 | 4/2015 | Eder et al. | |
| 2015/0159198 A1 | 6/2015 | McGall et al. | |
| 2015/0232615 A1 | 8/2015 | Kwiatkowski | |
| 2015/0258217 A1 | 9/2015 | Caravan | |
| 2016/0039850 A1 | 2/2016 | Segev | |
| 2016/0176903 A1 | 6/2016 | Segev | |
| 2016/0264737 A1 | 9/2016 | Bartholomew et al. | |
| 2016/0327859 A1 | 11/2016 | Idei et al. | |
| 2016/0347907 A1 | 12/2016 | Dose | |
| 2017/0326233 A1 | 11/2017 | Demeule et al. | |
| 2018/0065998 A1 | 3/2018 | Battrell et al. | |
| 2018/0092993 A1 | 4/2018 | Desai et al. | |
| 2018/0141935 A1 | 5/2018 | Josel et al. | |
| 2018/0312468 A1 | 11/2018 | Zhang et al. | |
| 2019/0136065 A1 | 5/2019 | Singh et al. | |
| 2019/0153232 A1 | 5/2019 | Matray et al. | |
| 2019/0177549 A1 | 6/2019 | Matray et al. | |
| 2019/0300716 A1 | 10/2019 | Matray et al. | |
| 2020/0032139 A1 | 1/2020 | Behrendt et al. | |
| 2020/0164085 A1 | 5/2020 | Brandish et al. | |
| 2020/0222554 A1 | 7/2020 | Matray et al. | |
| 2020/0330610 A1 | 10/2020 | Desai et al. | |
| 2020/0353089 A1 | 11/2020 | Matray | |
| 2020/0353094 A1 | 11/2020 | Matray | |
| 2020/0360526 A1 | 11/2020 | Matray | |
| 2021/0032277 A1 | 2/2021 | Matray et al. | |
| 2021/0032474 A1 | 2/2021 | Matray et al. | |
| 2021/0095130 A1 | 4/2021 | Matray et al. | |
| 2021/0096135 A1 | 4/2021 | Matray et al. | |
| 2021/0128591 A1 | 5/2021 | Matray | |
| 2021/0139440 A1 | 5/2021 | Ramsden et al. | |
| 2021/0340380 A1 | 11/2021 | Matray et al. | |
| 2021/0395530 A1 | 12/2021 | Matray et al. | |
| 2022/0160887 A1 | 5/2022 | Matray et al. | |
| 2022/0168433 A1 | 6/2022 | Matray et al. | |
| 2022/0168435 A1 | 6/2022 | Matray et al. | |
| 2022/0175951 A1 | 6/2022 | Boitano et al. | |
| 2022/0220314 A1 | 7/2022 | Singh et al. | |
| 2022/0227794 A1 | 7/2022 | Matray et al. | |
| 2022/0305127 A1 | 9/2022 | Thomas et al. | |
| 2022/0372297 A1 | 11/2022 | Matray et al. | |
| 2022/0380603 A1 | 12/2022 | Matray et al. | |
| 2022/0402963 A1 | 12/2022 | Matray et al. | |
| 2023/0012304 A1 | 1/2023 | Matray et al. | |
| 2023/0129481 A1 | 4/2023 | Matray et al. | |
| 2024/0043455 A1 | 2/2024 | Battrell et al. | |
| 2024/0092820 A1 | 3/2024 | Matray et al. | |
| 2024/0132725 A1 | 4/2024 | Sherif | |
| 2024/0207423 A1 | 6/2024 | Matray | |
| 2024/0210408 A1 | 6/2024 | Jackson et al. | |

FOREIGN PATENT DOCUMENTS

| | | | | |
|---|---|---|---|---|
| CN | 103319378 | A | 9/2013 | |
| CN | 104072727 | A | 10/2014 | |
| CN | 106589005 | A | 4/2017 | |
| CN | 107106685 | A | 8/2017 | |
| CN | 107709470 | A | 2/2018 | |
| CN | 109153860 | A | 1/2019 | |
| EP | 0708837 | B1 | 3/2006 | |
| GB | 2 372 256 | A | 8/2002 | |
| GB | 2 554 666 | A | 4/2018 | |
| JP | S61207395 | A | 9/1986 | |
| JP | H04282391 | A | 10/1992 | |
| JP | 2000017183 | A | 1/2000 | |
| JP | 2014527071 | A | 10/2014 | |
| JP | 2017124994 | A | 7/2017 | |
| JP | 2018507863 | A | 3/2018 | |
| JP | 2018515628 | A | 6/2018 | |
| JP | 2019516821 | A | 6/2019 | |
| JP | 2021518410 | A | 8/2021 | |
| JP | 7069033 | B2 | 5/2022 | |
| KR | 101041446 | B1 | 6/2011 | |
| KR | 10-2015-0007795 | A | 1/2015 | |
| KR | 20160022358 | A | 2/2016 | |
| KR | 10-2020-0133374 | A | 11/2020 | |
| KR | 102530707 | B1 | 5/2023 | |
| SU | 1121931 | A1 | 4/1988 | |
| WO | WO 9502700 | A1 | 1/1995 | |
| WO | WO 9506731 | A2 | 3/1995 | |
| WO | WO 9832463 | A2 | 7/1998 | |
| WO | WO 0173123 | A2 | 10/2001 | |
| WO | WO 0222883 | A1 | 3/2002 | |
| WO | WO 02083954 | A1 | 10/2002 | |
| WO | WO 2004007751 | A2 | 1/2004 | |
| WO | WO 2007094135 | A1 | 8/2007 | |
| WO | WO 2009113645 | A1 | 9/2009 | |
| WO | WO 2010026957 | A1 | 3/2010 | |
| WO | WO 2013012687 | A2 | 1/2013 | |
| WO | WO 2014102803 | A1 | 7/2014 | |
| WO | WO 2014147642 | A1 | 9/2014 | |
| WO | WO 2015027176 | A1 | 2/2015 | |
| WO | WO 2015091953 | A1 | 6/2015 | |
| WO | WO 2015155753 | A2 | 10/2015 | |
| WO | WO 2016183185 | A1 | 11/2016 | |
| WO | WO 2017003639 | A2 | 1/2017 | |
| WO | WO 2017062271 | A2 | 4/2017 | |
| WO | WO 2017089890 | A1 | 6/2017 | |
| WO | WO 2017094897 | A1 | 6/2017 | |
| WO | WO 2017177065 | A2 | 10/2017 | |
| WO | WO 2017197144 | A1 | 11/2017 | |
| WO | WO 2018045278 | A1 | 3/2018 | |
| WO | WO 2019126691 | A1 | 6/2019 | |
| WO | WO-2019140227 | A1 * | 7/2019 | ........... A61K 31/192 |
| WO | WO 2019182765 | A1 | 9/2019 | |
| WO | WO 2019182766 | A1 | 9/2019 | |
| WO | WO 2020219959 | A1 | 10/2020 | |

OTHER PUBLICATIONS

Arian et al., "1,9-Dialkoxyanthracene as a 1O2-Sensitive Linker," *J. Am. Chem. Soc.* 133:3972-3980, 2011.

Aviñó et al., "Solid-phase synthesis of oligomers carrying several chromophore units linked by phosphodiester backbones," *Bioorganic & Medicinal Chemistry Letters* 18:2306-2310, 2008.

Avirah et al., "Infrared Absorbing Croconaine Dyes: Synthesis and Metal Ion Binding Properties," *J. Org. Chem.* 73(1):274-279, 2008.

Babitskaya et al., "Bromoacyl Analogues of Phosphatidycholine with Intramolecular Fluorescence Quenching and Their Use as Substrates for Continuous Monitoring of Phospholipase A2 Activity," *Applied Biochemistry and Microbiology* 40(4):351-356, 2004.

Bag et al., "Triazolyl-donor-acceptor chromophore-decorated unnatural amino acids and peptides: FRET events in a β-turn conformation," *Chem. Commun.* 50:433-435, 2014.

Bargh et al., "Cleavable linkers in antibody-drug conjugates," *Chemical Society Reviews* 48(16):4361-4374, Aug. 21, 2019. (15 pages).

Beaucage et al., "The Functionalization of Oligonucleotides Via Phosphoramidite Derivatives," *Tetrahedron* 49(10):1925-1963, 1993.

Becker et al., "New Thermotropic Dyes Based on Amino-Substituted Perylendicarboximides," *Chem. Eur. J.* 6(21):3984-3990, 2000.

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015.

Bergstrom et al., "XMT-1522 induces tumor regressions in pre-clinical models representing HER2-positive and HER2 low-expressing breast cancer," Mersana Therapeutics, Abstract P4-14-28, 2015, 1 page.

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).

Bergstrom et al., "Potent Promise," *Innovations in Pharmaceutical Technology* 49:16-20, 2014.

Boldyrev et al., "Synthesis and Characteristics of New Fluorescent Probes Based on Cardiolipin," *Russian Journal of Bioorganic Chemistry* 35(2):219-224, 2009.

(56) References Cited

OTHER PUBLICATIONS

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Breul et al., "Fluorescent monomers as building blocks for dye labeled polymers: synthesis and application in energy conversion, biolabeling and sensors," Chem. Soc. Rev. 42(12):5366-5407, 2013.

Brinkley, "A brief survey of methods for preparing protein conjugates with dyes, haptens, and cross-linking reagents," *Bioconjugate Chem* 3:2-13, 1992.

Buckhout-White et al., "Assembling programmable FRET-based photonic networks using designer DNA scaffolds," *Nature Communications* 5:5615, Dec. 11, 2014. (16 pages).

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

CAPLUS Accession No. 1991:467753, Mielewczyk et al., "5' end fluorescent labelling of oligonucleotides with riboflavin-derived phosphitylating reagent," *Acta Biochimica Polonica* 36(3-4):225-233, 1989. (1 page).

CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (1 page).

CAPLUS Accession No. 1995:733249, WO9506731A2, filed Mar. 9, 1995. (1 page).

CAPLUS Accession No. 1995:849926, Reed et al., "Structure-Activity Relationships of Cytotoxic Cholesterol-Modified DNA Duplexes," *Journal of Medicinal Chemistry* 38(22):4587-4596, Oct. 27, 1995. (1 page).

CAPLUS Accession No. 1997:497709, Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (1 page).

CAS Registry No. 862288-26-4, American Chemical Society, 2021. (1 page).

Chang et al., "A General Approach for Generating Fluorescent Probes to Visualize Piconewton Forces at the Cell Surface," *J. Am. Chem. Soc.* 138:2901-2904, 2016. (4 pages).

Chattopadhyay et al., "Brilliant Violet Fluorophores: A New Class of Ultrabright Fluorescent Compounds for Immunofluorescence Experiments," *Cytometry Part A* 81A:456-466, 2012.

Chen et al., "Synthesis and properties of new segmented block poly(urethane-urea)s containing phosphatidylcholine analogues and polybutadienes," *Macro-Molecular Chemistry and Physics* 197(5):1587-1597, May 1996. (11 pages).

Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (10 pages).

Chong et al., "Oxygen Quenching of Pyrene-Lipid Fluorescence in Phosphatidylcholine Vesicles—A Probe for Membrane Organization," *Biophys. J.* 47:613-621, 1985.

Ciccotelli et al., "Polyguanine-conjugated antigens for scavenger receptor targeting and self-adjuvanting vaccines (VAC13P.1125)," *The Journal of Immunology* 194(Suppl. 1):214.5, May 1, 2015 [Abstract]. (1 page).

Cuppoletti et al., "Oligomeric fluorescent labels for DNA," *Bioconjug. Chem.* 16(3):528-534, 2005.

Dai et al., "DNA-polyfluorophore excimers as sensitive reporters for esterases and lipases," *Chem. Commun.* 46:1221-1223, 2010.

Damian et al., "Synthesis and DNA Interaction of Platinum Complex/Peptide Chimera as Potential Drug Candidates," *Eur. J. Org. Chem.* 6161-6170, 2010.

De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.

Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.

DiVittorio et al., "Synthetic peptides with selective affinity for apoptotic cells," *Org. Biomol. Chem.* 4:1966-1976, 2006.

Doi et al., "Hetero-Selective DNA-Like Duplex Stabilized by Donor-Acceptor Interactions," *Chem. Eur. J.* 21:15974-15980, 2015.

Drescher et al., "General Synthesis and Aggregation Behaviour of New Single-Chain Bolaphospholipids: Variations in Chain and Headgroup Structures," *Chemistry—A European Journal* 14(22):6796-6804, 2008.

Dropulic et al., "Update on New Antivirals Under Development for the Treatment of Double-Stranded DNA Virus Infections," Clinical Pharmacology & Therapeutics 88(5):610-619, Nov. 2010.

Dubrovsky, "Semiconductor nanoparticles as reporters in multiplexed immunoassay and cell analysis," *International Journal of Nanoscience* 8(1 & 2):163-167, 2009.

Finniss et al., "A versatile acid-labile linker for antibody-drug conjugates," Med. Chem, Commun; 5; Apr. 1, 2014, 4 pages.

Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.

Franzini et al., "Identification of Structure-Activity Relationships from Screening a Structurally Compact DNA-Encoded Chemical Library," *Angewandte Chemie International Edition* 54:3927-3931, Feb. 3, 2015 [with supporting information]. (41 pages).

Gao et al., "Libraries of Composite Polyfluors Built from Fluorescent Deoxyribosides," *Journal of the American Chemical Society* 124:11590-11591, 2002.

Gao et al., "Modified DNA Analogues That Sense Light Exposure with Color Changes," *Journal of the American Chemical Society* 126:12748-12749, 2004.

Gordon et al., "Analysis of simulated and experimental fluorescence recovery after photobleaching. Data for two diffusing components," *Biophysical Journal* 68:766-778, 1995.

Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.

Gupta et al., "Dendrimers: Novel Polymeric Nanoarchitectures for Solubility Enhancement," *Biomacromolecules* 7(3):649-658, Mar. 2006 [Published online Feb. 15, 2006]. (10 pages).

Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.

Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.

Haraguchi, "Live Cell Imaging: Approaches for Studying Protein Dynamics in Living Cells," *Cell Structure And Function* 27:333-334, 2002.

Hasegawa et al., "Cysteine, histidine and glycine exhibit anti-inflammatory effects in human coronary arterial endothelial cells," *Clinical and Experimental Immunology* 167:269-274, Jan. 11, 2012. (6 pages).

Irani et al., "Molecular properties of human IgG subclasses and their implications for designing therapeutic monoclonal antibodies against infectious diseases," *Molecular Immunology* 67:171-182, 2015.

Jain et al. "Current ADC Linker Chemistry," *Pharm. Res.* 32:3526-3540, 2015.

Johansson, "Choosing Reporter-Quencher Pairs for Efficient Quenching Through Formation of Intramolecular Dimers," *Methods in Molecular Biology* 335:17-29, 2006.

(56) References Cited

OTHER PUBLICATIONS

Kashida et al., "A Cationic Dye Triplet as a Unique "Glue" That Can Connect Fully Matched Termini of DNA Duplexes," *Chem. Eur. J.* 17:2614-2622, 2011.
Khandare et al., "Polymer-drug conjugates: Progress in polymeric prodrugs," *Progress in Polymer Science* 31(4):359-397, Apr. 2006. (39 pages).
Kolpashchikov, "Binary Probes for Nucleic Acid Analysis," *Chemical Reviews* 110(8):4709-4723, Jun. 28, 2010. (15 pages).
Koo et al., "Fluorescent DNA chemosensors: identification of bacterial species by their volatile metabolites," *Chemical Communications* 47:11435-11437, 2011.
Kozma et al., "Fluorescent Ligands for Adenosine Receptors," *Bioorganic & Medicinal Chemistry Letters* 23: 26-36, 2013.
Krueger at al., "Fluorescent Amino Acids: Modular Building Blocks for the Assembly of New Tools for Chemical Biology," *ChemBioChem* 14:788-799, 2013.
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.
Lee et al., "The spectroscopic analysis for binding of amphipathic and antimicrobial model peptides containing pyrenylalanine and tryptophan to lipid bilayer," *Biochimica et Biophysica Acta* 984:174-182, Sep. 4, 1989. (9 pages).
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Lewis et al., "Orientation Control of Fluorescence Resonance Energy Transfer Using DNA as a Helical Scaffold," *J. Am. Chem. Soc.* 127(28):10002-10003, 2005.
Li et al., "Polymeric Drugs: Advances in the development of pharmacologically active polymers," *Journal of Controlled Release* 219:369-382, 2015.
Li et al., "Responsive nanogel-based dual fluorescent sensors for temperature and Hg2+ ions with enhanced detection sensitivity," *J. Mater. Chem.* 20:10716-10723, 2010.
Liso et al., "Polymeric drugs derived from Ibuprofen with improved antiinflammatory profile," *Journal of Biomedical Materials Research* 32:553-560, Dec. 1996. (8 pages).
Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010 (14 Pages).
Liu et al., "Imidazole inhibits autophagy flux by blocking autophagic degradation and triggers apoptosis via increasing FoxO3a-Bim expression," *International Journal of Oncology* 46:721-731, Feb. 2015. (11 pages).
Liu et al., "Increased Cytotoxicity and Decreased In Vivo Toxicity of FdUMP[10] Relative to 5-FU," *Nucleosides & Nucleotides* 18(8):1789-1802, Aug. 1999. (14 pages).
Luo et al., "Sensitive and rapid quantification of C-reactive protein using quantum dot-labeled microplate immunoassay," *Journal of Translational Medicine* 10(24):1-9, 2012.
Lvnitski et al., "Introducing charge transfer functionality into prebiotically relevant β-sheet peptide fibrils," *Chemical Communications* 50:6733-6736, May 12, 2014. (4 pages).
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Marras et al., "Efficiencies of fluorescence resonance energy transfer and contact-mediated quenching in oligonucleotide probes," *Nucleic Acids Research* 30(21):e122, Nov. 1, 2002. (8 pages).
Masuko et al., "Fluorescence resonance energy transfer from pyrene to perylene labels for nucleic acid hybridization assays under homogenous solution conditions," *Nucleic Acids Research* 28(8):e34, 2000 (8 pages).
McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.
Mersana Therapeutics, URL= http://www.mersana.com, download date Jan. 3, 2019, 9 pages.
Midoux et al., "Chemical vectors for gene delivery: a current review on polymers, peptides and lipids containing histidine or imidazole as nucleic acids carriers," *British Journal of Pharmacology* 157:166-178, May 2009. (13 pages).
Mielewczyk et al., "5' end fluorescent labelling of oligonucleotides with riboflavin-derived phosphitylating reagent," *Acta Biochimica Polonica* 36(3-4):225-233, 1989. (9 pages).
Molotkovsky et al., "Perylenoyl- and Anthrylvinyl-Labeled Lipids as Membrane Probes," *Biochimica et Biophysica Acta* 778:281-288, 1984.
Moss, "Nomenclature of Fused and Bridged Fused Ring Systems," *Pure & Appl. Chem.* 70(1):143-216, 1998.
Mthembu et al., "Breaking a Couple: Disulfide Reducing Agents," *ChemBioChem* 21, 2020. (10 pages).
Nolting, "Linker Technology for Antibody-Drug Conjugates," in Ducry (ed.), *Antibody-Drug Conjugates,* Humana Press, Totowa, NJ, 2013, Ch. 5, pp. 71-100.
Nussbaumer et al., "Amplification of Chirality by Supramolecular Polymerization of Pyrene Oligomers," *Angewandte Chemie International Edition* 50:5490-5494, 2011.
Oh et al., "Low-dose guanidine and pyridostigmine: relatively safe and effective long-term symptomatic therapy in Lambert-Eaton myasthenic syndrome," *Muscle & Nerve* 20:1146-1152, Sep. 1997. (7 pages).
Paris et al., "Probing DNA sequences in solution with a monomer-excimer fluorescence color change," *Nucleic Acids Research* 26(16):3789-3793, 1998.
Pawelczyk et al., "Molecular Consortia-Various Structural and Synthetic Concepts for More Effective Therapeutics Synthesis," *International Journal of Molecular Sciences* 19:1104, Apr. 6, 2018. (19 pages).
Pelegrin et al., "Antiviral Monoclonal Antibodies: Can They Be More Than Simple Neutralizing Agents?" *Trends in Microbiology* 23(10):653-665, Oct. 2015.
Petersen et al., "Acyclic, achiral enamide nucleoside analogues. The importance of the C=C bond in the analogue for its ability to mimic natural nucleosides," *Organic & Biomolecular Chemistry* 1:3293-3296, Sep. 4, 2003. (4 pages).
Petreus et al., "Polyester imides containing main-chain phosphorus," *Revue Roumaine de Chimie* 34(8):971-978, 1994 (with English Abstract).
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Poupart et al., "Aminopropargyl derivative of terpyridine-bis(methylenamine) tetraacetic acid chelate of europium (Eu (TMT)-AP3): a new reagent for fluorescent labelling of proteins and peptides," Org. Biomol. Chem. 4:4165-4177, Oct. 2006.
Pownall et al., "Kinetics of Spontaneous and Plasma-Stimulated Sphingomyelin Transfer," *Biochimica et Biophysica Acta* 712:169-176, 1982.
PubChem, "US20100012929A1-20100121-C00010_4," SID No. 140452858, retrieved Mar. 29, 2016 from URL https://pubchem.ncbi.nlm.nih.gov/substance/140452858#sectio . . . , 6 pages.
Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (24 pages).
Reed et al., "Structure-Activity Relationships of Cytotoxic Cholesterol-Modified DNA Duplexes," *Journal of Medicinal Chemistry* 38(22):4587-4596, Oct. 27, 1995. (10 pages).

(56) References Cited

OTHER PUBLICATIONS

Ren et al., "An Antisense Oligodeoxynucleotide-Doxorubicin Conjugate: Preparation and Its Reversal Multidrug Resistance of Human Carcinoma Cell Line In Vitro," Nucleosides, Nucleotides & Nucleic Acids 23(10):1595-1607, 2004.
RN 230952-79-1, Registry Database Compound, 1999.
Rochat et al., "Water-Soluble Cationic Conjugated Polymers: Response to Electron-Rich Bioanalytes," *J. Am. Chem. Soc.* 135:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Saito et al., "Dual-labeled oligonucleotide probe for sensing adenosine via FRET: A novel alternative to SNPs genotyping," Chem. Commun.:2133-2135, 2007.
Samal et al., "Cationic polymers and their therapeutic potential," *Chemical Society Reviews* 41:7147-7194, Aug. 2012. (48 pages).
Shuey et al., "Cyclohexanediol Bisphosphates as Models for Phospholipid-Metal Ion Binding Sites," *Bioorganic Chemistry* 21:95-108, Mar. 1993. (14 pages).
Shuman et al., "Bacterial DNA repair by non-homologous end joining," *Nature Reviews Microbiology* 5:852-861, Nov. 2007.
Singh et al., "Multiplexed measurement of membrane protein populations," *Caplus* 2003:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE* 9939:993904, 2016 (10 pages).
STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology* 77:89-97, Oct. 2004 [Published online Jul. 15, 2004]. (9 pages).
Stuart et al., "Site-Specific DNA-Doxorubicin Conjugates Display Enhanced Cytotoxicity to Breast Cancer Cells," *Bioconjugate Chemistry* 25:406-413, 2014.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "High yield production of high molecular weight poly-(ethylene glycol)/ α-cyclodextrin polyrotaxanes by aqueous one-pot approach," *Polymer* 53:2884-2889, 2012.
Sun et al., "Self-assembled biodegradable micellar nanoparticles of amphiphilic and cationic block copolymer for siRNA delivery," *Biomaterials* 29:4348-4355, available online Aug. 2008. (8 pages).
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Tabujew et al., "Chapter One: Functionalization of Cationic Polymers for Drug Delivery Applications," *RSC Polymer Chemistry Series* 13, 2015. (29 pages).
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, Feb. 2002.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Teyssot et al., "Aromatic Nitrogen Donors for Efficient Copper(1)-NHC CuAAC under Reductant-Free Conditions," *Eur. J. Org. Chem.* 3507-3515, 2010.
Tram et al., "Oligonucleotide Labeling Using BODIPY Phosphoramidite," *Nucleosides, Nucleotides & Nucleic Acids* 30(1):1-11, 2011.
Vinogradov et al., "Total synthesis and biochemical characterization of mirror image barnase," *Chem Sci.* 6: 2997-3002, 2015.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
Wang et al., "Novel dexamethasone-HPMA copolymer conjugate and its potential application in treatment of rheumatoid arthritis," *Arthritis Research & Therapy* 9(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007 (18 Pages).
Winiger et al., "Long-Distance Electronic Energy Transfer in Light-Harvesting Supramolecular Polymers," *Angew. Chem. Int. Ed.* 53:13609-13613, 2014.
Wu Yi et al., "$^{Py}$A-Modified Oligodeoxyadenylates: Expanded Fluorescence Phenomena and Structural Formation," *Chemistry—An Asian Journal* 7:60-63, Nov. 2011. (4 pages).
Xu et al., "Synthesis of [D-Pyrenylalanine4,4']gramicidin S by Solid-Phase-Synthesis and Cyclization-Cleavage Method with Oxime Resin," *Chemistry Letters* 21:191-194, Feb. 1992. (4 pages).
Yu et al., "Targeted Delivery of an Anti-Inflammatory PDE4 Inhibitor to Immune Cells via an Antibody-drug Conjugate," Molecular Therapy 24(12):2078-2089, Dec. 2016.
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromol. Biosci.* 17:1600125, 2017 (8 pages).
Zhao et al., "Mussel-Inspired One-Pot Synthesis of a Fluorescent and Water-Soluble Polydopamine-Polyethyleneimine Copolymer," Macromol. Rapid Commun. 36:909-915, 2015.

* cited by examiner

AUTOMATED SYNTHESIS OF POLYMERIC DUAL DRUGS

BACKGROUND

Technical Field

The present disclosure is generally directed to dimeric and polymeric biologically active compounds having spacing groups with or without a chromophore moiety (e.g., a fluorescent dye), compounds, and methods of treatment related to the same.

Description of the Related Art

Targeted drug conjugates, unlike, e.g., chemotherapy, deliver drugs to target cells, with little or no off-target activity. Typically, targeted drug conjugates comprise a targeting molecule that is linked to a biologically active payload or drug. By combining the unique targeting capability with the therapeutic effectiveness of a biologically active drug, conjugates can deliver the drug only to the intended target and minimize potential side effects.

Antibody-drug conjugates (ADCs) are one class of targeted drug conjugates that are of particular interest, for example for cancer treatment. ADCs for cancer treatment combine the targeting features of monoclonal antibodies with cancer-killing ability of cytotoxic agents to provide a therapeutic with several advantages over other chemotherapeutics. However, challenges related to the complexity of ADC constructs, specifically the chemical linker between antibody and drug, has caused significant difficulties for development of new and effective therapeutics. Although the first ADC was approved in 2001, it took almost a decade before the next ADC was approved. As of today, only Adcetris®, Besponsa®, Enhertu®, Mylotarg®, Padcev®, Polivy®, and Kadcyla® are commercially available globally (Zevalin® has been approved in China only).

Thus, there exists a need in the art for developing potent, targeting drug conjugates having a high therapeutic index and methods of preparing the same. The present disclosure fulfills this need and provides further related advantages.

BRIEF SUMMARY

One embodiment provides a compound having the following Structure (I):

(I)

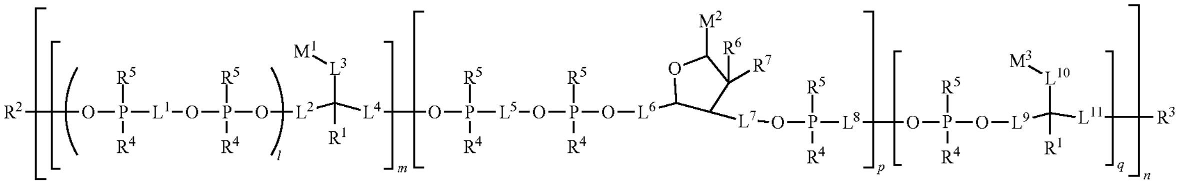

or a pharmaceutically acceptable salt, stereoisomer, or tautomer thereof, wherein $R^1$, $R^2$, $R^3$, $R^4$, $R^5$, $R^6$, $R^7$, $L^1$, $L^2$, $L^3$, $L^4$, $L^5$, $L^6$, $L^7$, $L^8$, $L^9$, $L^{10}$, $L^{11}$, $M^1$, $M^2$, $M^3$, l, m, n, p, and q are as defined herein.

Another embodiment provides a compound having the following structure (Ia):

(Ia)

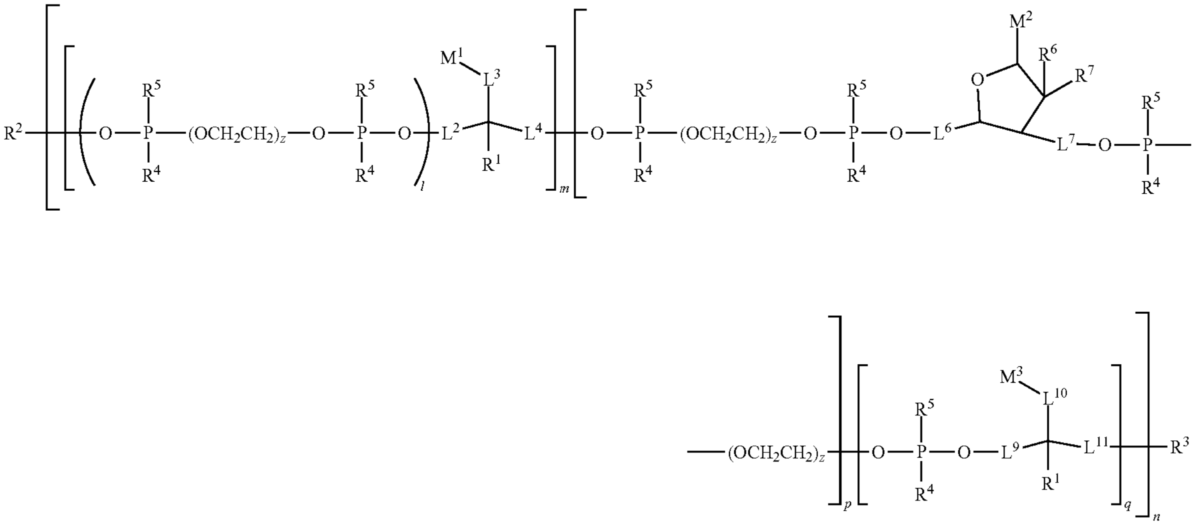

or a pharmaceutically acceptable salt, stereoisomer, or tautomer thereof, wherein $R^1$, $R^2$, $R^3$, $R^4$, $R^5$, $R^6$, $R^7$, $L^2$, $L^3$, $L^4$, $L^6$, $L^7$, $L^9$, $L^{10}$, $L^{11}$, $M^1$, $M^2$, $M^3$, l, m n p and q are as defined herein.

Another embodiment provides a compound having the following structure (Ib):

(Ib)

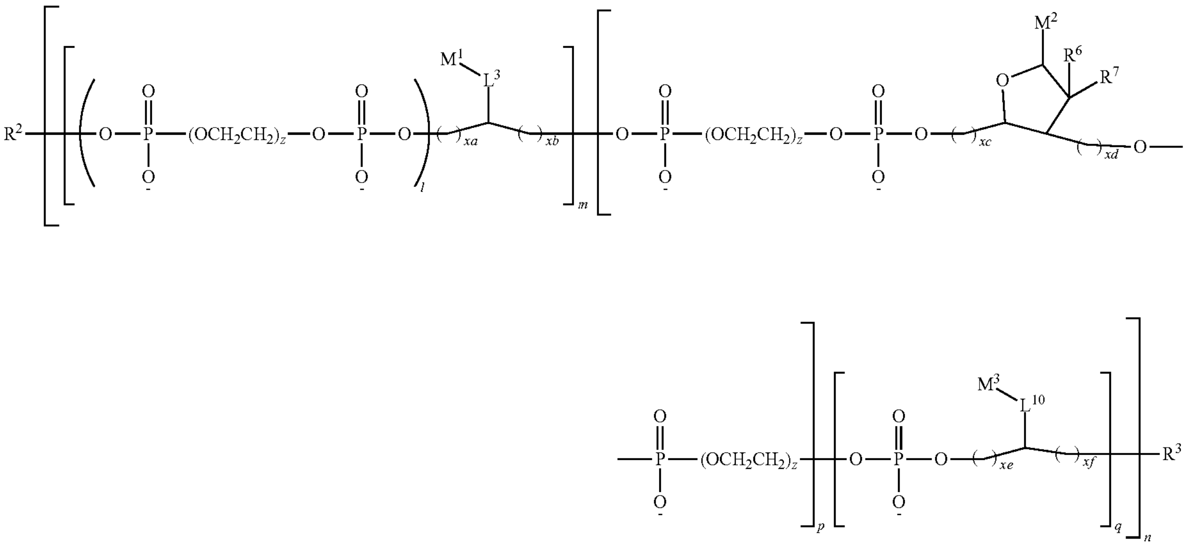

or a pharmaceutically acceptable salt, stereoisomer, or tautomer thereof, wherein $R^2$, $R^3$, $R^6$, $R^7$, $L^3$, $L^{10}$, $M^1$, $M^2$, $M^3$, l, m, n, p, and q are as defined herein.

Yet another embodiment provides a compound having the following structure (Ic):

(Ic)

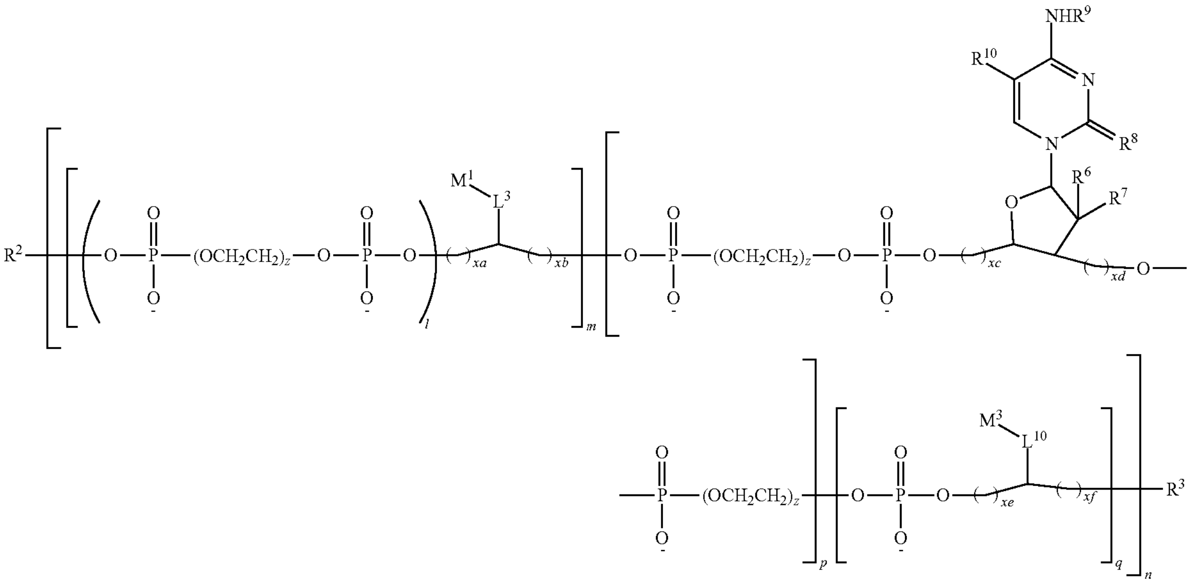

or a pharmaceutically acceptable salt, stereoisomer, or tautomer thereof, wherein $R^2$, $R^3$, $R^6$, $R^7$, $R^8$, $R^9$, $R^{10}$, $L^3$, $L^{10}$, $M^1$, $M^3$, l, m, n, p, and q are as defined herein.

Further, yet another embodiment provides a compound having the following structure (Id):

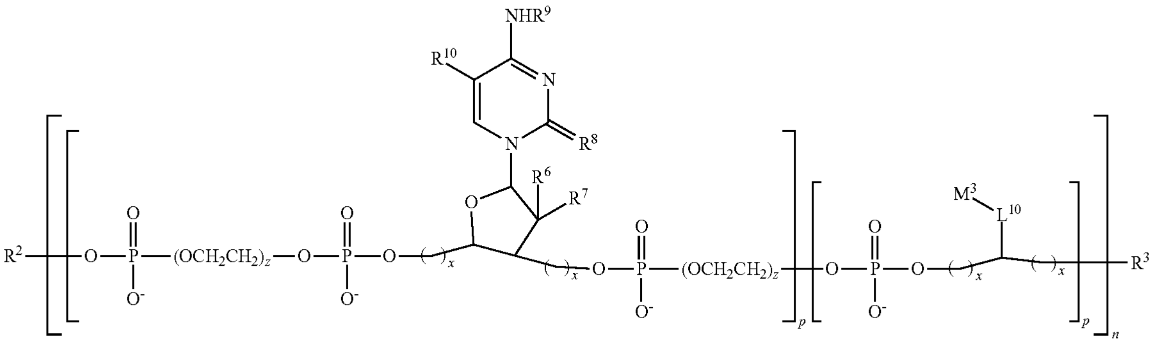

(Id)

or a pharmaceutically acceptable salt, stereoisomer, or tautomer thereof, wherein $R^2$, $R^3$, $R^6$, $R^7$, $R^8$, $R^9$, $R^{10}$, $L^{10}$, $M^3$, n, p, and q are as defined herein.

Further, yet another embodiment provides a compound having the following structure (Ie):

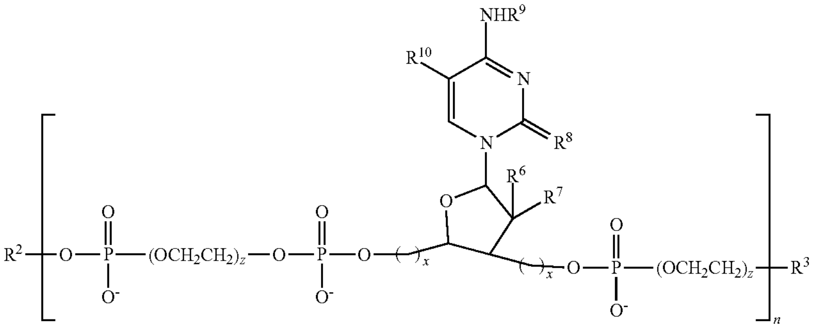

(Ie)

or a pharmaceutically acceptable salt, stereoisomer, or tautomer thereof, wherein $R^2$, $R^3$, $R^6$, $R^7$, $R^8$, $R^9$, $R^{10}$, and n are as defined herein.

One embodiment provides a compound having the following Structure (III):

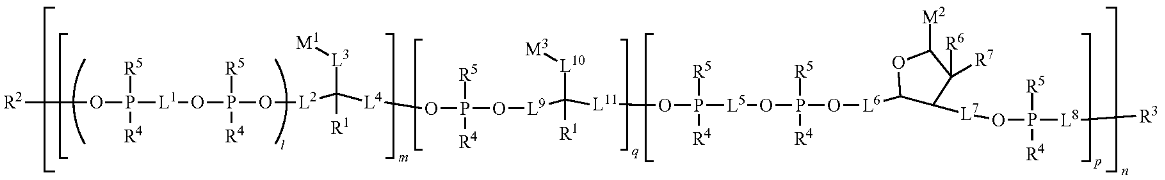

(III)

or a pharmaceutically acceptable salt, stereoisomer, or tautomer thereof, wherein $R^1$, $R^2$, $R^3$, $R^4$, $R^5$, $R^6$, $R^7$, $L^1$, $L^2$, $L^3$, $L^4$, $L^5$, $L^6$, $L^7$, $L^8$, $L^9$, $L^{10}$, $L^{11}$, $M^1$, $M^2$, $M^3$ l, m, n, p, and q are as defined herein.

Another embodiment provides a compound having the following structure (IIIa):

(IIIa)

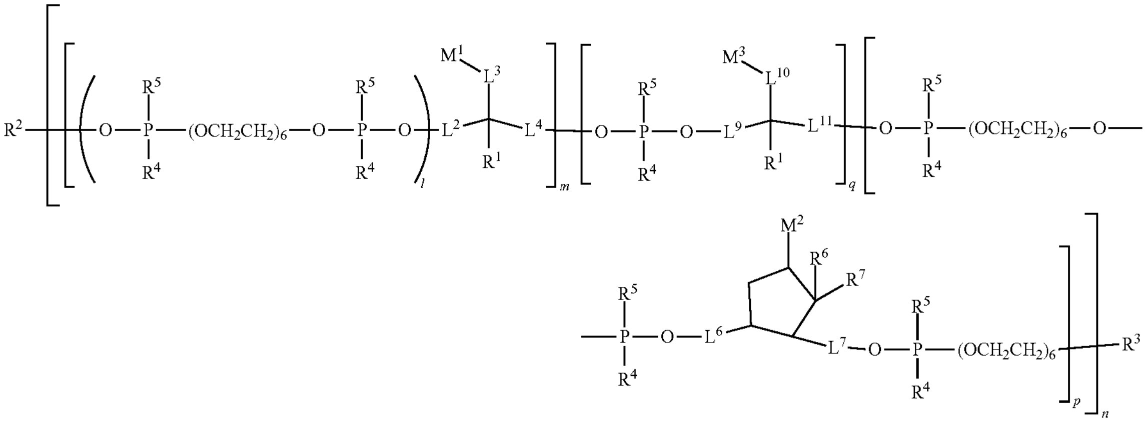

or a pharmaceutically acceptable salt, stereoisomer, or tautomer thereof, wherein $R^1$, $R^2$, $R^3$, $R^4$, $R^5$, $R^6$, $R^7$, $L^2$, $L^3$, $L^4$, $L^6$, $L^7$, $L^9$, $L^{10}$, $L^{11}$, $M^1$, $M^2$, $M^3$, l, m, n, p, and q are as defined herein.

Another embodiment provides a compound having the following structure (IIIb):

(IIIb)

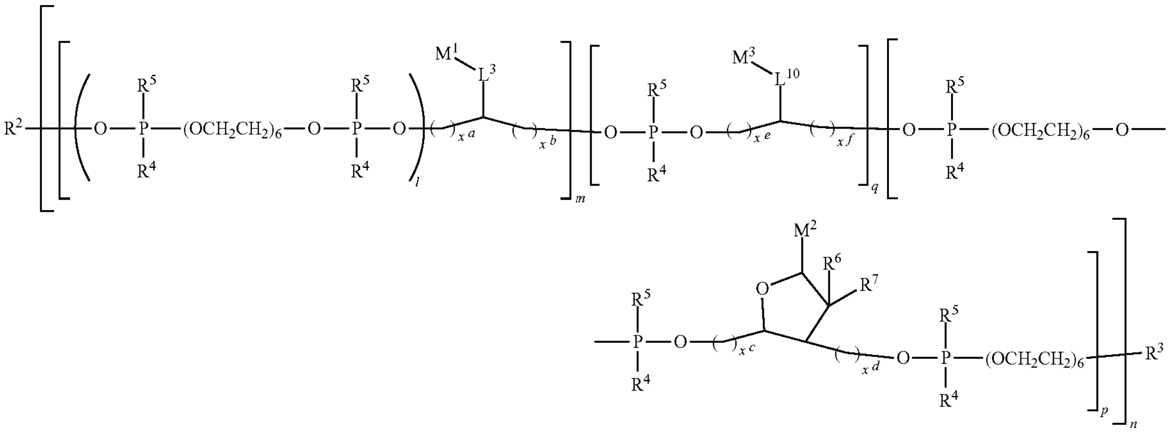

or a pharmaceutically acceptable salt, stereoisomer, or tautomer thereof, wherein $R^2$, $R^3$, $R^6$, $R^7$, $L^3$, $L^{10}$, $M^1$, $M^2$, $M^3$, l, m, n, p, and q are as defined herein.

Yet another embodiment provides a compound having the following structure (IIIc):

(IIIb)

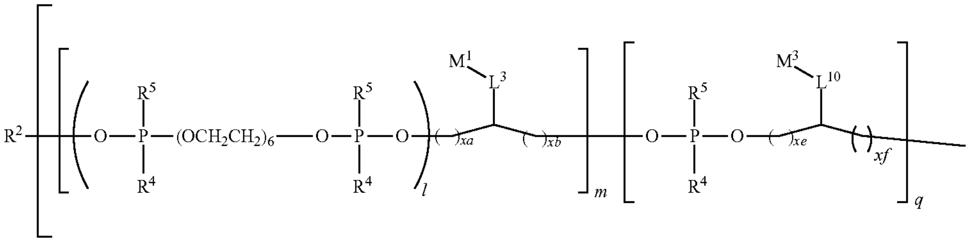

-continued

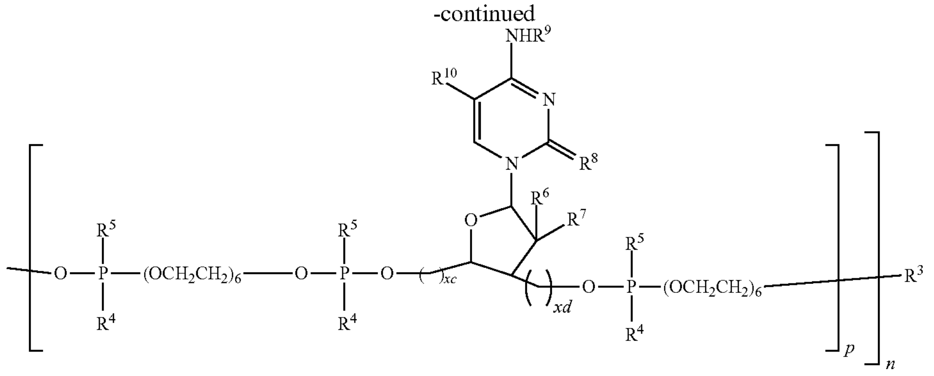

or a pharmaceutically acceptable salt, stereoisomer, or tautomer thereof, wherein $R^2$, $R^3$, $R^6$, $R^7$, $R^3$, $R^9$, $R^{10}$, $L^3$, $L^{10}$, $M^1$, $M^3$, l, m, n, p, and q are as defined herein.

Further, yet another embodiment provides a compound having the following structure (IIId):

(IIId)

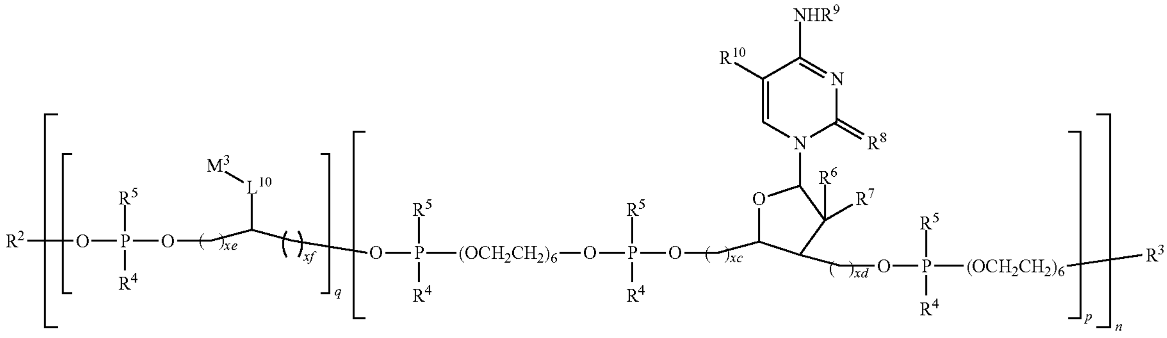

or a pharmaceutically acceptable salt, stereoisomer, or tautomer thereof, wherein $R^2$, $R^3$, $R^6$, $R^7$, $R^8$, $R^9$, $R^{10}$, $L^{10}$, $M^3$, n, p, and q are as defined herein.

These and other aspects of the disclosure will be apparent upon reference to the following detailed description.

BRIEF DESCRIPTION OF THE SEVERAL VIEWS OF THE DRAWINGS

In the FIGURES, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
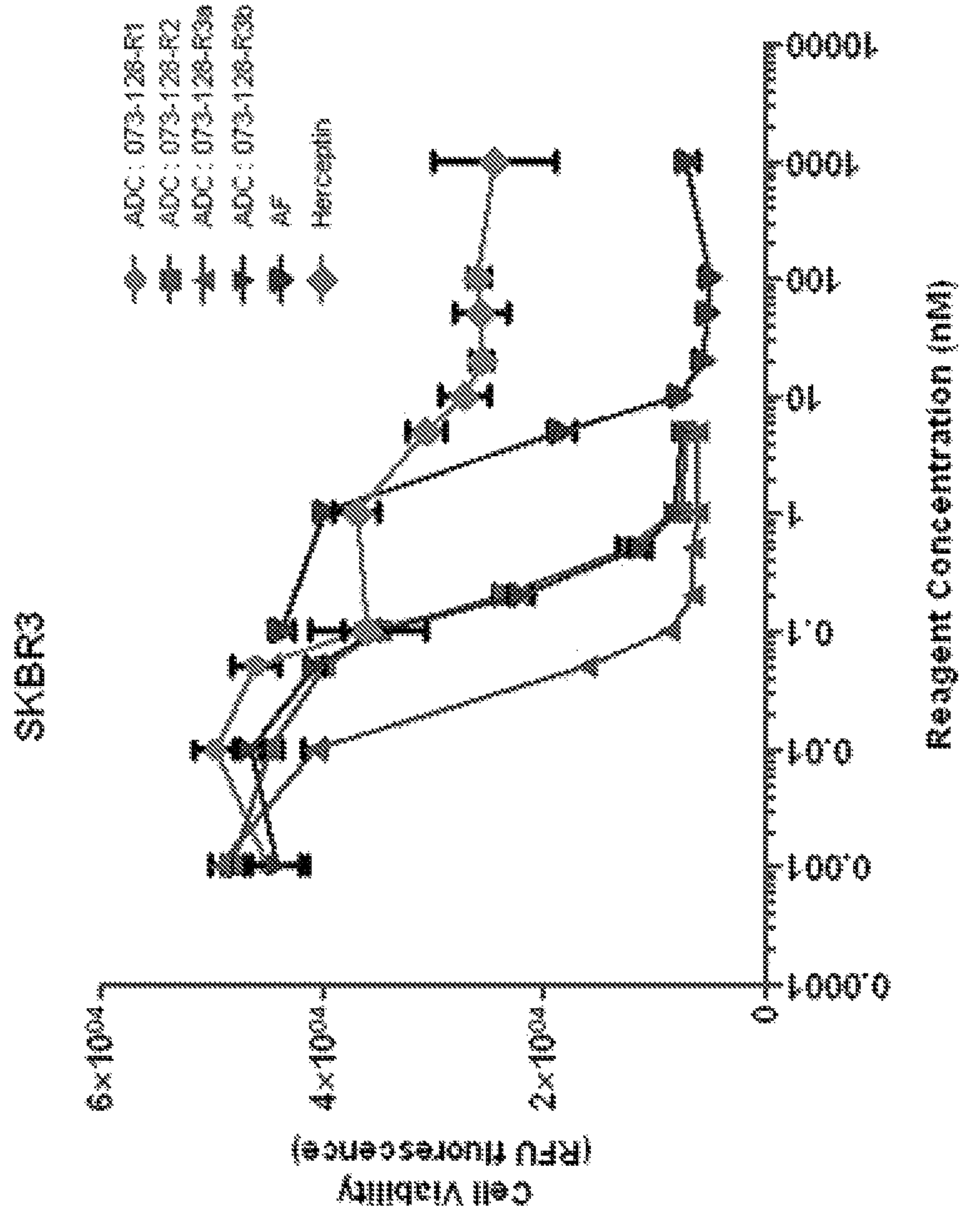
FIGS. 1-2 illustrate cell proliferation assay results for Her2 negative in PC3.

In the following description, certain specific details are set forth in order to provide a thorough understanding of various embodiments of the disclosure. However, one skilled in the art will understand that embodiments of the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the $-NH_2$ group.

"Carboxy" refers to the $-CO_2H$ group.

"Cyano" refers to the —CN group.

"Formyl" refers to the —C(=O)H group.

"Hydroxy" or "hydroxyl" refers to the —OH group.

"Imino" refers to the =NH group.

"Nitro" refers to the $-NO_2$ group.

"Oxo" refers to the =O group.

"Sulfhydryl," "thiol," or "thio" refers to the —SH group.

"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Heteroalkylene" refers to an alkylene group, as defined above, comprising at least one heteroatom (e.g., Si, N, O, P or S) within the alkylene chain or at a terminus of the alkylene chain. In some embodiments, the heteroatom is within the alkylene chain (i.e., the heteroalkylene comprises at least one carbon-[heteroatom]$_x$-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C" linking group and "HEG" linking groups illustrated below:

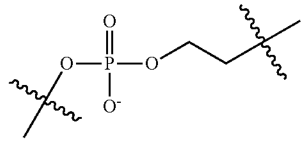

"C linker"

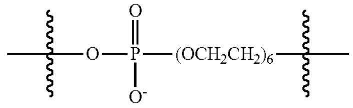

"HEG linker"

Multimers of the above C linker and HEG linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatom. Exemplary heteroatomic linkers include single atoms selected from the group consisting of O, N, P, and S, and multiple heteroatoms for example a linker having the formula —P($O^-$)(=O)O— or —OP($O^-$)(=O)O— and multimers and combinations thereof.

"Phosphate" refers to the —OP(=O)($R_a$)$R_b$ group, wherein $R_a$ is OH, $O^-$ or $OR_c$; and $R_b$ is OH, $O^-$, $OR_c$, a thiophosphate group or a further phosphate group, wherein $R_c$ is a counter ion (e.g., Na+ and the like).

"Phosphoalkyl" refers to the —OP(=O)($R_a$)$R_b$ group, wherein $R_a$ is OH, $O^-$ or $OR_c$; and $R_b$ is —Oalkyl, wherein $R_c$ is a counter ion (e.g., $Na^+$ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Phosphoalkylether" refers to the —OP(=O)($R_a$)$R_b$ group, wherein $R_a$ is OH, $O^-$ or $OR_c$; and $R_b$ is —Oalkylether, wherein $R_c$ is a counter ion (e.g., $Na^+$ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphate" refers to the —OP(=$R_a$)($R_b$)$R_c$ group, wherein $R_a$ is O or S, $R_b$ is OH, $O^-$, $S^-$, $OR_d$ or $SR_d$; and $R_c$ is OH, SH, $O^-$, $S^-$, $OR_a$, $SR_a$, a phosphate group or a further thiophosphate group, wherein $R_d$ is a counter ion (e.g., $Na^+$ and the like) and provided that: i) $R_a$ is S; ii) $R_b$ is $S^-$ or $SR_a$; iii) $R_c$ is SH, $S^-$ or $SR_a$; or iv) a combination of i), ii) and/or iii).

"Thiophosphoalkyl" refers to the —OP(=$R_a$)($R_b$)$R_c$ group, wherein $R_a$ is O or S, $R_b$ is OH, $O^-$, $S^-$, $OR_d$ or $SR_a$; and $R_c$ is —Oalkyl, wherein $R_d$ is a counter ion (e.g., Na+ and the like) and provided that: i) $R_a$ is S; ii) $R_b$ is $S^-$ or $SR_a$; or iii)$R_a$ is S and $R_b$ is $S^-$ or $SR_a$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphoalkylether" refers to the —OP(=$R_a$)($R_b$)$R_c$ group, wherein $R_a$ is O or S, $R_b$ is OH, $O^-$, $S^-$, $OR_a$ or $SR_a$; and $R_c$ is —Oalkylether, wherein $R_d$ is a counter ion (e.g., $Na^+$ and the like) and provided that: i) $R_a$ is S; ii) $R_b$ is $S^-$ or $SR_d$; or iii) $R_a$ is S and $R_b$ is $S^-$ or $SR_a$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

The suffix "-ene" refers to a particular structural feature (e.g., alkyl, aryl, heteroalkyl) attached to the rest of the molecule through a single bond and to the radical group through a single bond. In other words, the suffix "-ene"

refers to a particular structural feature having the description given herein which is a linker between the molecule and a radical group. The points of attachment of the "-ene" chain to the rest of the molecule and to the radical group can be through one atom of or any two atoms within the chain. For example, an alkyleneheteroalkylene refers to a linker comprising an alkylene portion and a heteroalkylene portion.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1,3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous, and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions. In some embodiments, the linker is a heteroatomic linker (e.g., comprising 1-10 Si, N, O, P, or S atoms), a heteroalkylene (e.g., comprising 1-10 Si, N, O, P, or S atoms and an alkylene chain) or an alkylene linker (e.g., comprising 1-12 carbon atoms). In some embodiments, a heteroalkylene linker comprises the following structure:

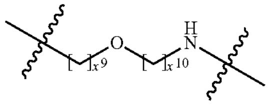

wherein:

$x^9$ and $x^{10}$ are each independently a integer greater than 0. In some embodiments, the heteroatomic linker is —O—, —S—, or —OP(=O)O—O$^-$. In some embodiments, the heteroalkylene linker comprises —OP(=O)O—O$^-$. In some embodiments, the heteroalkylene linker comprises at least one S—S bond.

"Physiologically cleavable linker" refers to a molecular linkage that can be split or separated a prescribed manner, resulting in two or more separate molecules while in the presence of an in vivo or in vitro environment of an organism or cell system. Generally, physiological conditions that induce such a cleavage or scission event may include a temperature ranging from about 20 to 40° C., an atmospheric pressure of about 1 atm (101 kPa or 14.7 psi), a pH of about 6 to 8, a glucose concentration of about 1 to 20 mM, atmospheric oxygen concentration, and earth gravity. In some embodiments, physiological conditions include enzymatic conditions (i.e., enzymatic cleavage). Bond cleavage or scission can be homolytic or heterolytic.

"Solid support" or "solid resin" refers to any solid substrate known in the art for solid-phase support of molecules, for example a "microparticle" refers to any of a number of small particles useful for attachment to compounds of the disclosure, including, but not limited to, glass beads, magnetic beads, polymeric beads, nonpolymeric beads, and the like. In certain embodiments, a microparticle comprises polystyrene beads. In some embodiments, the solid support or solid resin is controlled pore glass or macroporous polystyrene.

A "solid support residue" refers to the functional group remaining attached to a molecule when the molecule is cleaved from the solid support. Solid support residues are known in the art and can be easily derived based on the structure of the solid support and the group linking the molecule thereto.

Embodiments disclosed herein are also meant to encompass all compounds of Structures (I), (Ia), (Ib), (Ic), (Id), (Ie), (III), (IIIa), (IIIb), (IIIc), or (IIId) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of Structure (I), (Ia), (Ib), (Ic), (Id), (Ie), (III), (IIIa), (IIIb), (IIIc), or (IIId) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins, and the like. Particularly preferred organic bases are isopropylamine, diethylamine, ethanolamine, trimethylamine, dicyclohexylamine, choline, caffeine, and the like.

Crystallizations may produce a solvate of the compounds described herein (e.g., a compound of Structure (I), (Ia), (Ib), (Ic), (Id), (Ie), (III), (IIIa), (IIIb), (IIIc), or (IIId). Embodiments of the present disclosure include all solvates of the described compounds. As used herein, the term “solvate” refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compounds of the disclosure may be true solvates, while in other cases the compounds of the disclosure may merely retain adventitious water or another solvent or be a mixture of water plus some adventitious solvent.

Embodiments of the compounds of the disclosure (e.g., compounds of Structure (I), (Ia), (Ib), (Ic), (Id), (Ie), ((III), (IIIa), (IIIb), (IIIc), or (IIId)), or their salts, tautomers or solvates may contain one or more stereocenters and may thus give rise to enantiomers, diastereomers, and other stereoisomeric forms that may be defined, in terms of absolute stereochemistry, as (R)- or (S)- or, as (D)- or (L)- for amino acids. Embodiments of the present disclosure are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other features giving rise to geometric asymmetry, and unless specified otherwise, it is intended that the compounds include both E and Z geometric isomers. Likewise, all tautomeric forms are also intended to be included.

A “stereoisomer” refers to a compound made up of the same atoms bonded by the same bonds but having different three-dimensional structures, which are not interchangeable. The present disclosure contemplates various stereoisomers and mixtures thereof and includes “enantiomers”, which refers to two stereoisomers whose molecules are non-superimposable mirror images of one another.

A “tautomer” refers to a proton shift from one atom of a molecule to another atom of the same molecule. The present disclosure includes tautomers of any said compounds. Various tautomeric forms of the compounds are easily derivable by those of ordinary skill in the art.

The term “biomolecule” refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the disclosure (e.g., compounds of structures (I), (Ia), (Ib), (Ic), (Id), (Ie), (III), (IIIa), (IIIb), (IIIc), or (IIId) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A “reactive group” is a moiety capable of reacting with a second reactive group (e.g., a “complementary reactive group”) to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

“Bio-conjugation” or “bio-conjugate” and related variations refer to a chemical reaction strategy for forming a stable covalent bond between two molecules. The term “bio-conjugation” is generally used when one of the molecules is a biomolecule (e.g., an antibody), but can be used to describe forming a covalent bond with a non-biomolecule (e.g., a polymeric resin). The product or compound resulting from such a reaction strategy is a “conjugate,” “bio-conjugate” or a grammatical equivalent.

The terms “visible” and “visually detectable” are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the disclosure may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the disclosure, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Non-limiting examples of photostable visible dyes suitable for use in the compounds and methods of the disclosure include azo dyes, thioindigo dyes, quinacridone pigments, dioxazine, phthalocyanine, perinone, diketopyrrolopyrrole, quinophthalone, and truarycarbonium.

The polymer compounds of various embodiments of the disclosure are useful for a wide variety of analytical applications, such as biochemical and biomedical applications, in which there is a need to determine the presence, location, spatial interaction or quantity of a particular analyte (e.g., biomolecule). In another aspect, therefore, the disclosure provides a method for visually detecting a biomolecule, comprising: (a) providing a biological system with a visually detectable biomolecule comprising the compound of the embodiments disclosed herein (e.g., compounds of structures ((I), (Ia), (Ib), (Ic), (Id), (Ie), (III), (IIIa), (IIIb), (IIIc), or (IIId) linked to a biomolecule; and (b) detecting the biomolecule by its visible properties. For purposes of the disclosure, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Non-limiting examples of such biological systems include cells, cell extracts, tissue samples, electrophoretic gels, assay mixtures, and hybridization reaction mixtures.

"Optional" or "optionally" means that the subsequently described event or circumstances may or may not occur; such a description includes instances where the event or circumstance occurs and instances where it does not. For example, "optionally substituted alkyl" means that the alkyl group may or may not be substituted and that the description includes both substituted alkyl groups and alkyl groups having no substitution.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

For ease of illustration, various compounds of Structure (I) or (III) comprising phosphorous moieties (e.g., phosphate and the like) are depicted in the anionic state (e.g., —OPO(OH)O—, —$OPO_3^{2-}$). One of skill in the art will readily understand that the charge is dependent on pH and the uncharged (e.g., protonated or salt, such as sodium or other cation) forms are also included in the scope of embodiments of the disclosure.

Compounds

As noted above, in one embodiment of the present disclosure, compounds useful as covalent linkers between biologically active moieties and targeting moieties are provided. In another embodiment, an inclusion of one or more biologically active moieties (e.g., gemcitabine) within the backbone of compounds is provided. In other embodiments, an inclusion of one or more fluorescent dyes into the compounds useful as covalent linkers between biologically active moieties and targeting moieties is provided. Further, an inclusion of one or more fluorescent dyes into the compounds allows for visualizing area that the compounds are attached. In other embodiments, compounds useful as synthetic intermediates for preparation of compounds comprising one or more biologically active moieties are provided.

Numerous advantages are afforded by embodiments disclosed herein, including the ability to control the number of biologically active moieties that are attached to the polymer and any subsequent targeting moiety, the ability to control the type of biologically active moieties that are attached to the polymer and any subsequent targeting moiety, the ability to control the number of fluorescent dye moieties that are attached to the polymer and any subsequent targeting moiety, and the ability to control the order of fluorescent dye moieties and biologically active moieties that are attached to the polymer and any subsequent targeting moiety. The composition of the polymer backbone can also be selected to afford desirable solubility properties, for example, by controlling the incorporation of charged moieties (e.g., number, frequency, spacing, etc.). In addition to the properties provided by the composition of the backbone, the side chains can be selected to provide a source for tuning the solubility of the compounds disclosed herein. Monomeric units of the polymer can be selected to incorporate different anticancer therapeutics during polymer synthesis and as a post synthetic modification following polymer synthesis (e.g., coupling to an amine pendant to the polymer backbone with a therapeutic agent having an activated ester moiety). The composition of the polymer backbone can also be selected to afford desirable fluorescent properties, for example, by controlling the incorporation of fluorescent dye moieties (e.g., number, frequency, spacing, etc.).

That is, the embodiments disclosed herein also provide compounds that can advantageously include multiple therapeutic agents, for example, for complimentary or synergistic therapeutic strategies. In addition, embodiments of the present disclosure provide combinations of therapeutic agents, targeting moieties, and dye moieties (e.g., chromophores or fluorophores) that can be used for simultaneous targeting, treatment, and detection. The ease of coupling polymer-drug constructs to targeting agents such as antibodies, antibody fragments, proteins or other clinically interesting agents provides utility to a wide variety of interesting applications (e.g., surface chemistries, assay development, etc.). Accordingly, in some embodiments, $M^1$ is a chromophore or fluorophore (e.g., FITC, 5-FAM, 6-FAM, and the like), and $M^2$ and/or $M^3$ is a therapeutic agent (e.g., a drug moiety such as Auristatin F or SN 38), and compounds disclosed herein have gemcitabine moieties embedded in the polymer backbone.

The compounds of certain embodiments also provide other desirable properties, including enhanced permeability and retention effects. In addition to providing necessary solubility characteristics, the chemical features of embodiments of the present compounds can be adjusted to modulate the compound's ability to permeate diseased cells/tissue and be retained within the same. These features allow effective delivery of biologically active agents by increasing permeation and increasing efficacy by enhancing retention.

Accordingly, in some embodiments the compounds have the following structure (I):

(I)

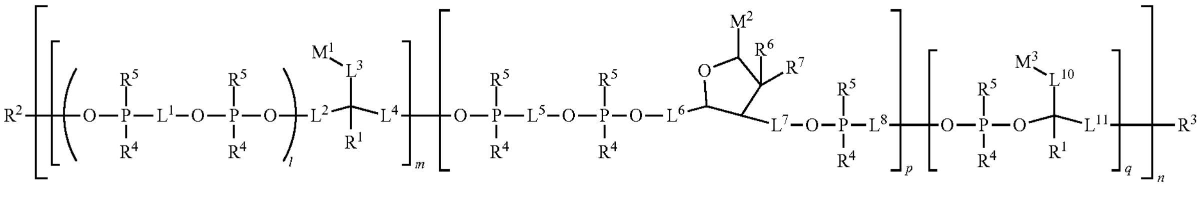

or a pharmaceutically acceptable salt, stereoisomer, or tautomer thereof, wherein:

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q, or a protected form thereof, L';

$R_a$ is O or S;

$R_b$ is OH, SH, $O^-$, $S^-$, $OR_a$ or $SR_a$;

$R_c$ is OH, SH, $O^-$, $S^-$, $OR_a$, OL', $SR_a$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

$R^4$ is, at each occurrence, independently OH, SH, $O^-$, $S^-$, $OR_a$ or $SR_a$;

$R^5$ is, at each occurrence, independently oxo or thioxo;

$R^6$ and $R^7$ are, at each occurrence, independently H, OH, or halo, provided that at least one of $R^6$ or $R^7$ is OH or halo;

$L^3$ and $L^{10}$ are, at each occurrence, independently a linker;

$L^1$, $L^2$, $L^4$, $L^5$, $L^6$, $L^7$, $L^8$, $L^9$, and $L^{11}$ are, at each occurrence, independently a direct bond or an optionally substituted linker;

$M^1$ is, at each occurrence, independently absent or a moiety comprising a fluorescent dye;

$M^2$ is, at each occurrence, independently a chromophore;

$M^3$ is, at each occurrence, independently a moiety comprising an anticancer therapeutic;

Q is, at each occurrence, independently a moiety comprising a reactive group, or protected form thereof, capable of forming a covalent bond with a complementary reactive group Q' on a targeting moiety;

L' is, at each occurrence, independently a linker comprising a covalent bond to Q, a targeting moiety, a linker comprising a covalent bond to a targeting moiety, a linker comprising a covalent bond to a solid support, a linker comprising a covalent bond to a solid support residue, a solid support residue, a linker comprising a covalent bond to a nucleoside, or a linker comprising a covalent bond to a further compound of Structure (I); and l is, at each occurrence, independently an integer of one or greater;

m is, at each occurrence, independently an integer of zero or greater;

n is an integer of one or greater;

at least one occurrence of p is an integer of 1 or greater, and each remaining p is either 0 or an integer of 1 or greater; and q is, at each occurrence, independently an integer of zero or greater.

In more specific embodiments, at least one occurrence of $L^1$, $L^5$, or $L^8$ is alkylene. In certain embodiments, at least one occurrence of $L^1$, $L^5$, or $L^8$ is methylene.

In more specific embodiments at least one occurrence of $L^1$, $L^5$, or $L^8$ is heteroalkylene. In certain embodiments, at least one occurrence of $L^1$, $L^5$, or $L^8$ comprises alkylene oxide. Further in some embodiments, the alkylene oxide is ethylene oxide. For example, the ethylene oxide is polyethylene oxide.

In some embodiments, $R^2$ is L'. In some other embodiments, L' is a linker to a targeting moiety.

In some more specific embodiments, L' is a linker to a targeting moiety, the linker comprising an alkylene oxide or phosphodiester moiety, or combinations thereof. In certain embodiments, L' has one of the following structures:

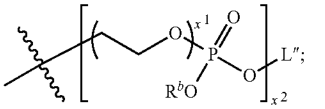

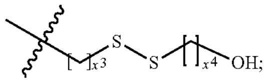

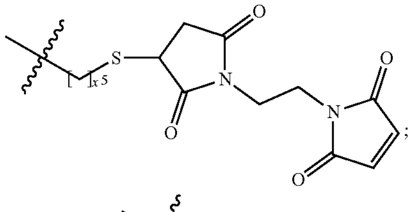

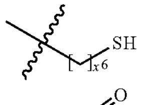

or

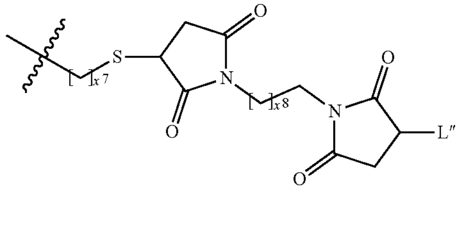

wherein:

$x^1$, $x^2$, $x^3$, $x^4$, $x^5$, $x^6$, $x^7$ and $x^8$ are independently an integer from 1 to 10;

$R^b$ is H, an electron pair or a counter ion;

L" is the targeting moiety or a linkage to the targeting moiety.

In some embodiments, the targeting moiety is an antibody or cell surface receptor antagonist. In some more specific embodiments, the antibody or cell surface receptor antagonist is an epidermal growth factor receptor (EGFR) inhibitor, a hepatocyte growth factor receptor (HGFR) inhibitor, an insulin-like growth factor receptor (IGFR) inhibitor, a folate, or a MET inhibitor.

In some embodiments, the targeting moiety is a monoclonal antibody which includes Abciximab, Adalimumab, Alemtuzumab, Alirocumab, Avibactam, Basiliximab, Benralizumab, Bezlotoxumab, Blinatumomab, Brodalumab, Burosumab, Canakinumab, Caplacizumab, Certolizumab pegol, Daclizumab, Denosumab, Dupilumab, Eculizumab, Emicizumab, Erenumab, Evolocumab, Fremanezumab, Galcanezumab, Golimumab, Guselkumab, Ibalizumab, Idarucizumab, Infliximab, Itolizumab, Ixekizumab, Lanadelumab, Lokivetmab, Mepolizumab, Natalizumab, Obiltoxaximab, Ocrelizumab, Omalizumab, Palivizumab, Ranibizumab, Raxibacumab, Reslizumab, Rmab, Rovelizumab, Ruplizumab, Sarilumab, Secukinumab, Tildrakizumab, Thiomab, Tocilizumab, Ustekinumab, Vedolizumab, Abrilumab, Actoxumab, Aducanumab, Afasevikumab, Afelimomab, Anifrolumab, Anrukinzumab (IMA-638), Aselizumab, Atorolimumab, Bapineuzumab, BCD-100, Bertilimumab, Besilesomab, Biciromab, Bimagrumab, Bimekizumab, Birtamimab, Bleselumab, Blosozumab, Bococizumab, Brazikumab, Briakinumab, Brolucizumab, Carlumab, Carotuximab, Cedelizumab, Clazakizumab, Clenoliximab, Concizumab, Cosfroviximab, CR6261, Crenezumab, Crizanlizumab, Crotedumab, Depatuxizumab, mafodotin, Derlotuximab biotin, Dezamizumab, Diridavumab, Domagrozumab, Dusigitumab, Ecromeximab, Edobacomab, Efalizumab, Efungumab, Eldelumab, Elezanumab, Enokizumab, Eptinezumab, Erlizumab, Etrolizumab, Evinacumab, Exbivirumab, Fanolesomab, Faralimomab, Faricimab, Fasinumab, Felvizumab, Fezakinumab, Flanvotumab, Fletikumab, Flotetuzumab, Fontolizumab, Foravirumab, Frovocimab, Fulranumab, Gantenerumab, Gavilimomab, Gevokizumab, Gimsilumab, Gomiliximab, Gosuranemab, Ianalumab, Inclacumab, Inolimomab, Iomab-B, Keliximab, Lampalizumab, Landogrozumab, Larcaviximab, Lebrikizumab, Lenvervimab, Lerdelimumab, Letolizumab, Libivirumab, Ligelizumab, Lodelcizumab, Lulizumab pegol, Marstacimab, Mavrilimumab, Metelimumab, Mirikizumab, Motavizumab, Muromonab CD3, Nebacumab, Nemolizumab, NEOD001, Nirsevimab, Odulimomab, Olendalizumab, Olokizumab, OMS721, Opicinumab, Orticumab, Otelixizumab, Otilimab, Oxelumab, Ozanezumab, Ozoralizumab, Pagibaximab, Panobacumab, Pascolizumab, Pateclizumab, PDR001, Perakizumab, Pexelizumab, Placulumab, Plozalizumab, Ponezumab, Porgaviximab, Prasinezumab, Priliximab, PRO 140, Quilizumab, Rafivirumab, Ralpancizumab, Ranevetmab, Ravagalimab, Ravulizumab, Refanezumab, Regavirumab, Relatlimab, Rinucumab, Risankizumab, Roledumab, Romosozumab, Rontalizumab, SA237, Satralizumab, Sevirumab, SHP647, Sifalimumab, Simtuzumab, Siplizumab, Sirukumab, Solanezumab, Sonepcizumab, Spartalizumab, Stamulumab, Sulesomab, Suptavumab, Sutimlimab, Suvizumab, Suvratoxumab, Tadocizumab, Talizumab, Tamtuvetmab, Tanezumab, Tefibazumab, Telimomab aritox, Teneliximab, Teplizumab, Teprotumumab, Tezepelumab, Tibulizumab, Toralizumab, Tralokinumab, Trevogrumab, Tuvirumab, Ulocuplumab, Urtoxazumab, Varisacumab, Vepalimomab, Vesencumab, Visilizumab, Vobarilizumab, Zolimomab aritox, trastuzumab, gemtuzumab, brentuximab, vorsetuzumab, lorvotuzumab, cantuzumab, bivatuzumabor inotuzumab, or vadastuximab.

In some embodiments, $R^2$ or $R^3$ has one of the following structures:

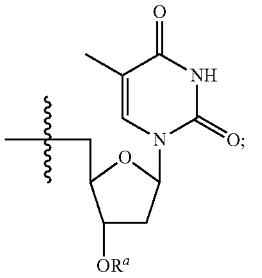

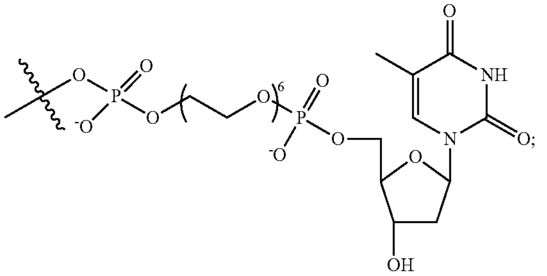

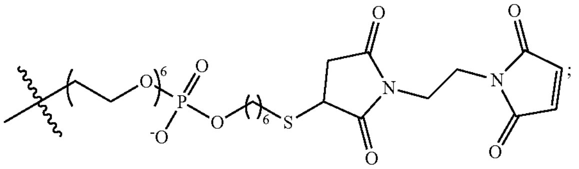

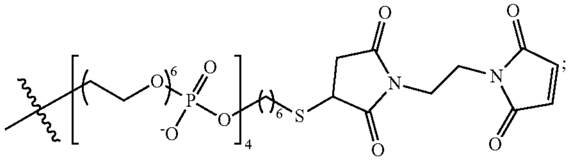

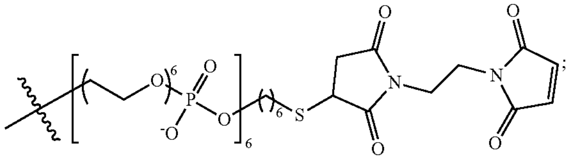

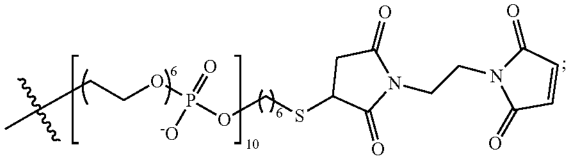

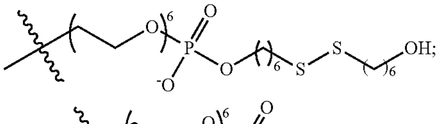

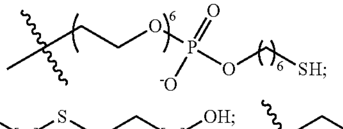

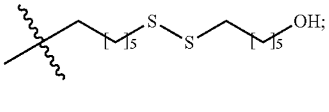

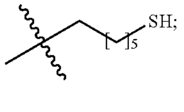

-continued
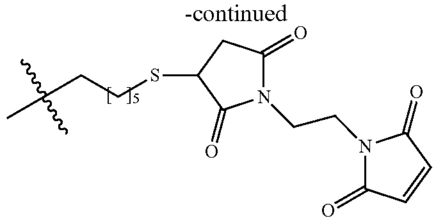
or
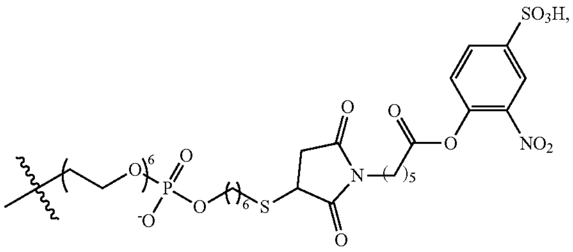
wherein
$R_a$ is H or a solid support.
In some more specific embodiments, $R^2$ has one of the following structures:
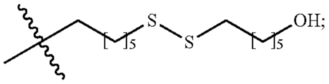
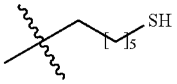
or
-continued
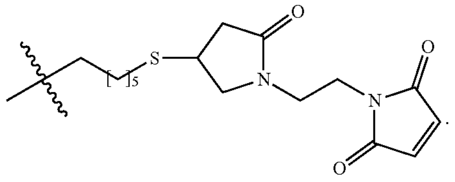
Further in some more specific embodiments, $R^3$ has the following structure:
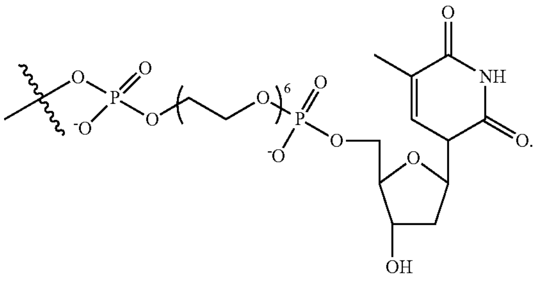
In some embodiments, the compound has the following structure (Ia):
(Ia)
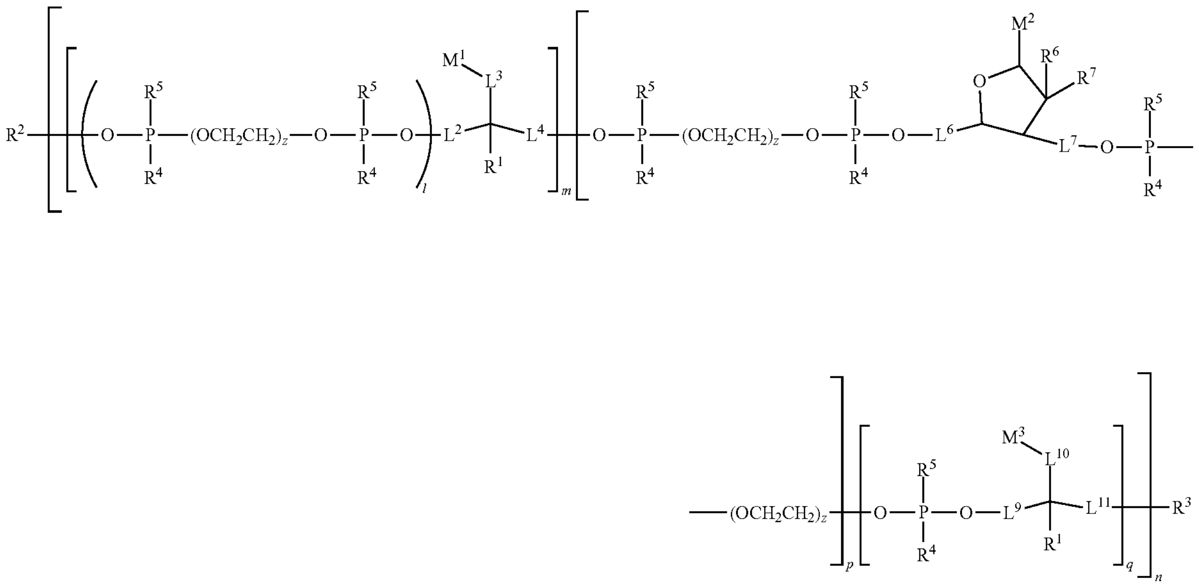

or a pharmaceutically acceptable salt, stereoisomer, or tautomer thereof, wherein z is, at each occurrence, independently an integer from 1 to 10.

In some embodiments, $R^5$ is, at each occurrence, independently OH, $O^-$ or $OR_d$. In some other embodiments, $R^4$ is, at each occurrence, oxo.

In some embodiments, the compound has the following structure (Ib):

(Ib)

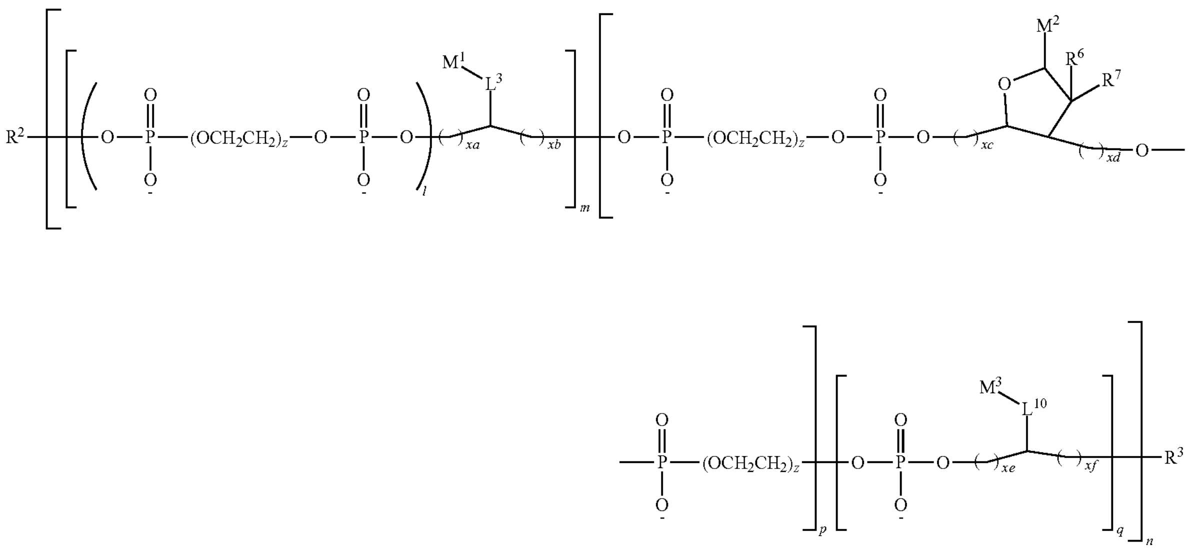

or a pharmaceutically acceptable salt, stereoisomer, or tautomer thereof, wherein $x^a$, $x^b$, $x^c$, $x^d$, $x^e$, and $x^f$ are, at each occurrence, independently an integer from 0 to 6.

In some more specific embodiments, the compound has the following structure (Ic):

(Ic)

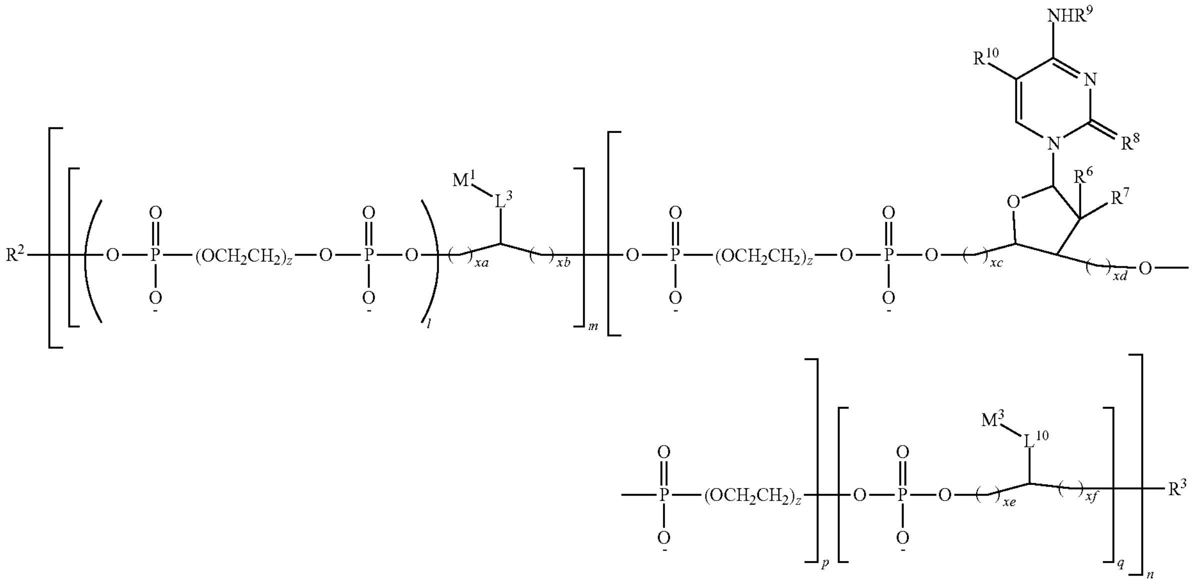

or a pharmaceutically acceptable salt, stereoisomer, or tautomer thereof, wherein $R^8$ is, at each occurrence, independently O, NH, or $NR^e$;

$R^9$ is, at each occurrence, independently H, alkyl, or optionally substituted alkyl;

$R^{10}$ is, at each occurrence, independently H or F; and $R^e$ is, at each occurrence, independently alkyl or optionally substituted alkyl.

In certain embodiments, m is an integer of zero.

In some more specific embodiments, the compound has the following structure (Id):

(Id)

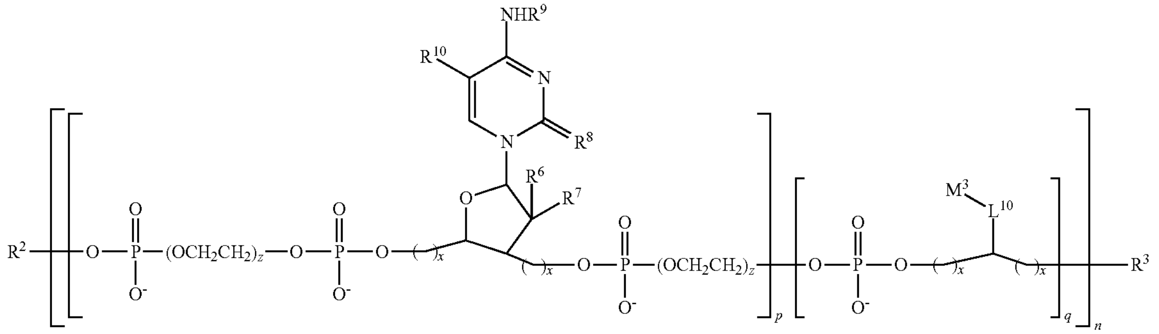

or a pharmaceutically acceptable salt, stereoisomer, or tautomer thereof.

In some more specific embodiments, the compound has the following structure (Ie):

(Ie)

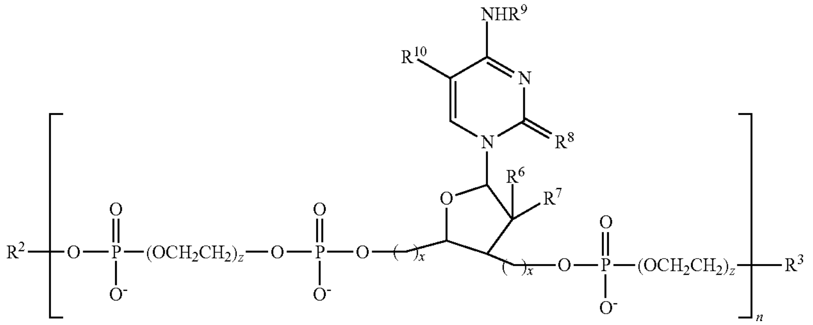

or a pharmaceutically acceptable salt, stereoisomer, or tautomer thereof.

In some embodiments, the compound has the following Structure (III):

(III)

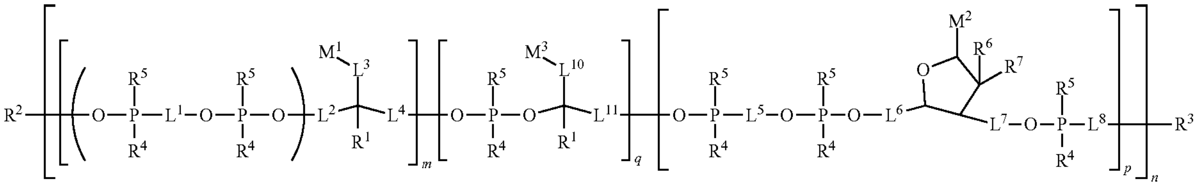

or a pharmaceutically acceptable salt, stereoisomer, or tautomer thereof, wherein $R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q, or a protected form thereof, L';

$R_a$ is O or S;

$R_b$ is OH, SH, $O^-$, $S^-$, $OR_a$ or $SR_d$;

$R_c$ is OH, SH, $O^-$, $S^-$, $OR_a$, OL', $SR_a$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

$R^4$ is, at each occurrence, independently OH, SH, $O^-$, $S^-$, $OR_d$ or $SR_d$;

$R^5$ is, at each occurrence, independently oxo or thioxo;

$R^6$ and $R^7$ are, at each occurrence, independently H, OH, or halo, provided that at least one of $R^6$ or $R^7$ is OH or halo;

$L^3$ and $L^{10}$ are, at each occurrence, independently a linker;

$L^1$, $L^2$, $L^4$, $L^5$, $L^6$, $L^7$, $L^8$, $L^9$, and $L^{11}$ are, at each occurrence, independently a direct bond or an optionally substituted linker;

$M^1$ is, at each occurrence, independently absent, a moiety comprising a fluorescent dye;

$M^2$ is, at each occurrence, independently a chromophore;

$M^3$ is, at each occurrence, independently a moiety comprising an anticancer therapeutic;

Q is, at each occurrence, independently a moiety comprising a reactive group, or protected form thereof, capable of forming a covalent bond with a complementary reactive group Q' on a targeting moiety;

L' is, at each occurrence, independently a linker comprising a covalent bond to Q, a targeting moiety, a linker comprising a covalent bond to a targeting moiety, a linker comprising a covalent bond to a solid support, a linker comprising a covalent bond to a solid support residue, a solid support residue, a linker comprising a covalent bond to a nucleoside, or a linker comprising a covalent bond to a further compound of Structure (I); and l is, at each occurrence, independently an integer of one or greater;

m is, at each occurrence, independently an integer of zero or greater;

n is an integer of one or greater;

at least one occurrence of p is an integer of 1 or greater, and each remaining p is either 0 or an integer of 1 or greater; and q is, at each occurrence, independently an integer of zero or greater.

In some more embodiments, the compound has the following structure (IIIa):

(IIIa)

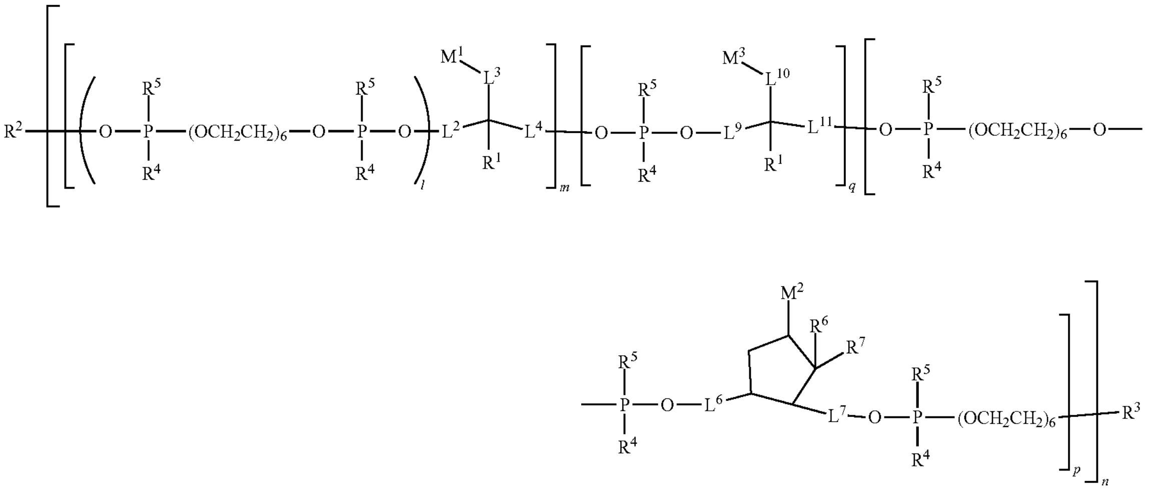

or a pharmaceutically acceptable salt, stereoisomer, or tautomer thereof.

In some more specific embodiments, the compound has the following structure (IIIb):

(IIIb)

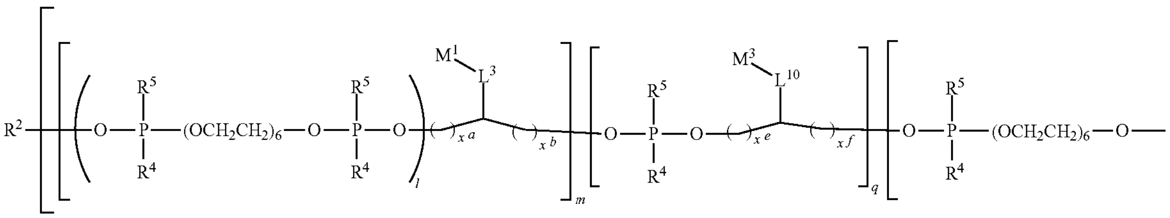

-continued

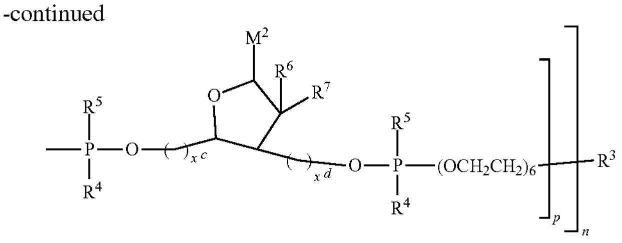

or a pharmaceutically acceptable salt, stereoisomer, or tautomer thereof, wherein $x^a$, $x^b$, $x^c$, $x^d$, $x^e$, and $x^f$ are, at each occurrence, independently an integer from 0 to 6.

In some more specific embodiments, the compound has the following structure (IIIc):

(IIIc)

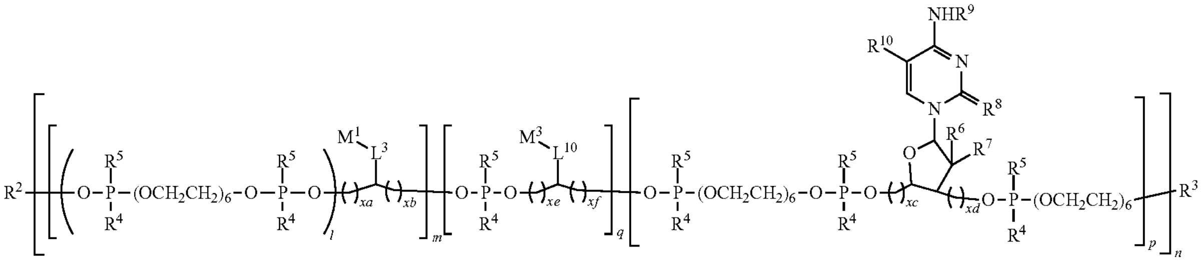

or a pharmaceutically acceptable salt, stereoisomer, or tautomer thereof, wherein $R^8$ is, at each occurrence, independently O, NH, or $NR^e$;

$R^9$ is, at each occurrence, independently H, alkyl, or optionally substituted alkyl;

$R^{10}$ is, at each occurrence, independently H or F; and $R^e$ is, at each occurrence, independently alkyl or optionally substituted alkyl.

In some more specific embodiments, the compound has the following structure (IIId):

(IIId)

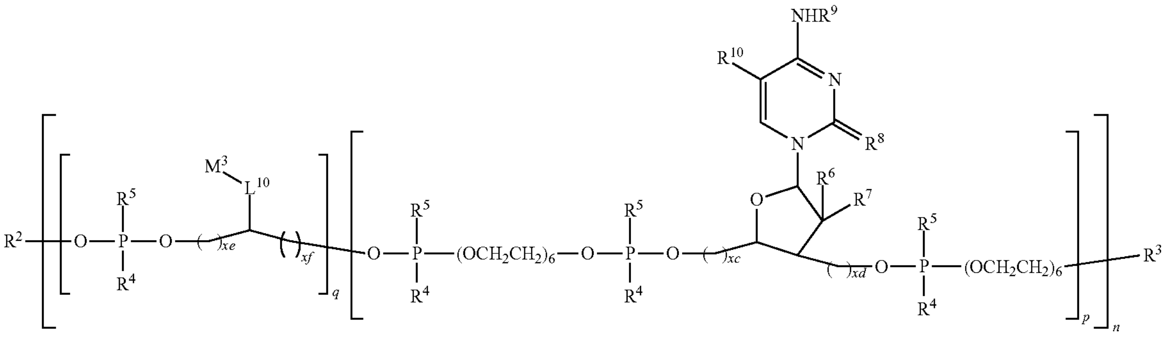

or a pharmaceutically acceptable salt, stereoisomer, or tautomer thereof.

The various linkers and substituents (e.g., $M^1$, $M^2$, $M^3$, Q, $R^1$, $R^2$, $R^3$, $L^1$, $L^2$, $L^3$, $L^4$, $L^5$, $L^6$, $L^7$, $L^8$, $L^9$, $L^{10}$, or $L^{11}$) in the compounds of structures (I), (Ia), (Ib), (Ic), (Id), (Ie), (III), (IIIa), (IIIb), (IIIc), or (IIId) are optionally substituted with one more substituent. For example, in some embodiments the optional substituent is selected to optimize the water solubility or other property of the compounds of structures (I), (Ia), (Ib), (Ic), (Id), (Ie), ((III), (IIIa), (IIIb), (IIIc), or (IIId). In certain embodiments, each alkyl, alkoxy, alkylether, alkoxyalkylether, phosphoalkyl, thiophosphoalkyl, phosphoalkylether and thiophosphoalkylether in the compounds of structures (I), (Ia), (Ib), (Ic), (Id), (Ie), (III), (IIIa), (IIIb), (IIIc), or (IIId) are optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether.

In some embodiments, $L^3$ or $L^{10}$ is, at each occurrence, independently a direct bond or an optionally substituted linker. In some embodiments, $L^3$ or $L^{10}$ is, at each occurrence, independently an optional alkylene, alkenylene, alkynylene, heteroalkylene, heteroalkenylene, heteroalkynylene, or heteroatomic linker. In some embodiments, $L^3$ or $L^{10}$ is a linker comprising a functional group capable of formation by reaction of two complementary reactive groups (e.g., an azide and an alkyne). In some embodiments, $L^3$ or $L^{10}$ is, at each occurrence, independently an optional alkylene, alkenylene, alkynylene, heteroalkylene, heteroalkenylene, heteroalkynylene, alkyleneheteroarylenealkylene, alkyleneheterocyclylenealkylene, alkylenecarbocyclylenealkylene, heteroalkyleneheteroarylenealkylene, heteroalkyleneheterocyclylenealkylene, heteroalkylenecarbocyclylenealkylene, heteroalkyleneheteroaryleneheteroalkylene, heteroalkyleneheterocyclyleneheteroalkylene, heteroalkylenecarbocyclyleneheteroalkylene, alkyleneheteroaryleneheteroalkylene, alkyleneheterocyclyleneheteroalkylene, alkylenecarbocyclyleneheteroalkylene, heteroarylene, heterocyclylene, carbocyclylene, alkyleneheteroarylene, alkyleneheterocyclylene, heteroarylenealkylene, alkylenecarbocyclylene, carbocyclylenealkylene, heteroalkyleneheteroarylene, heteroalkyleneheterocyclylene, heteroaryleneheteroalkylene, heteroalkylenecarbocyclylene, carbocyclyleneheteroalkylene, or heteroatomic linker. In some embodiments, $L^3$ or $L^{10}$ is optionally substituted.

In some embodiments, the linkers $L^3$ or $L^{10}$ can be used as a point of attachment of the $M^1$ and $M^3$ moieties to the remainder of the compound. In certain embodiments, $L^3$ or $L^{10}$, or both, is absent. In some embodiments, $L^3$ or $L^{10}$, or both, is present. In some more specific embodiments, $L^3$ or $L^{10}$, when present, are each independently alkylene or heteroalkylene. In certain embodiments, at least one occurrence of $L^3$ or $L^{10}$ is heteroalkylene. In some more specific embodiments, at least one occurrence of $L^3$ or $L^{10}$ comprises oxygen. In some embodiments, at least one occurrence of $L^3$ or $L^{10}$ has the following structure:

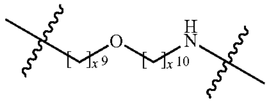

wherein:

$x^9$ and $x^{10}$ are each independently a integer greater than 0.

In some embodiments, $x^9$ is 1, 2, 3, or 4. In certain embodiments, $x^{10}$ is 2, 3, 4, or 5. In some specific embodiments, $x^9$ is 1 or 2 and $x^{10}$ is 2, 3, or 4. In certain specific embodiments, each occurrence of $L^3$ or $L^{10}$ is heteroalkylene. In some more specific embodiments, each occurrence of $L^3$ or $L^{10}$ comprises oxygen. In certain more specific embodiments, each occurrence of $L^3$ or $L^{10}$ has the following structure:

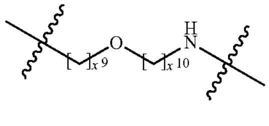

wherein:

$x^9$ and $x^{10}$ are each independently a integer greater than 0.

In some embodiments, $x^9$ is 1, 2, 3, or 4. In certain embodiments, $x^{10}$ is 2, 3, 4, or 5. In more specific embodiments, $x^9$ is 1 or 2 and $x^{10}$ is 2, 3, or 4. In certain other embodiments, at least one occurrence of $L^3$ or $L^{10}$ comprises the following structure:

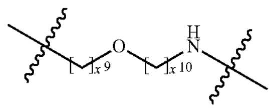

wherein:

$x^9$ and $x^{10}$ are each independently a integer greater than 0.

In certain embodiments, $L^3$ or $L^{10}$ further comprises a physiologically cleavable linker. In more specific embodiments, at least one occurrence of $L^3$ or $L^{10}$ comprises an amide bond, an ester bond, a phosphodiester bond, a disulfide bond, a double bond, a triple bond, an ether bond, a hydrazone, an amino acid sequence comprising one or more amino acid residues, a ketone, a diol, a cyano, a nitro, or combinations thereof. In more specific embodiments, at least one occurrence of $L^3$ or $L^{10}$ comprises one of the following structures:

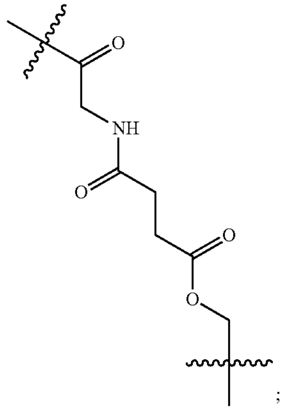 ; 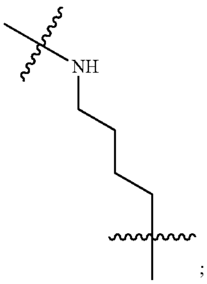 ;

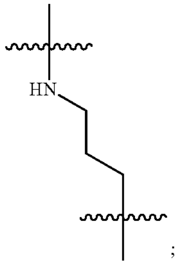 ; 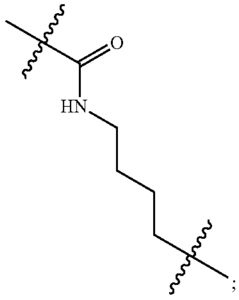 ;

-continued

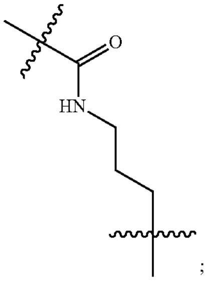

;

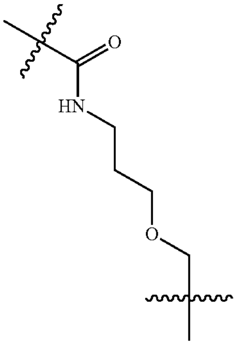

or

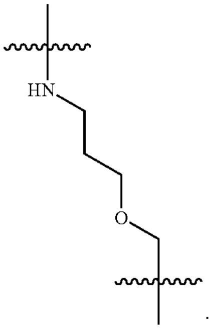

.

In certain embodiments, each occurrence of $L^3$ or $L^{10}$ comprises an amide bond, an ester bond, a phosphodiester bond, a disulfide bond, a double bond, a triple bond, an ether bond, a hydrazone, an amino acid sequence, a ketone, a diol, a cyano, a nitro or combinations thereof. In some more specific embodiments, each occurrence of $L^3$ or $L^{10}$ comprises one of the following structures:

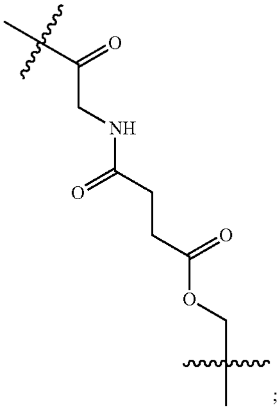

;

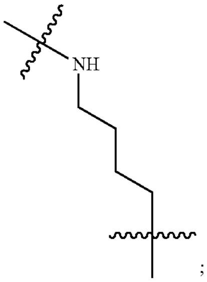

;

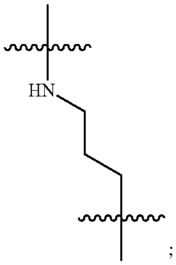

;

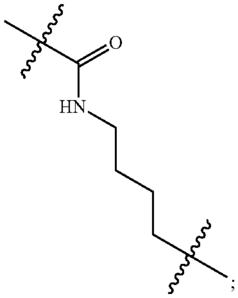

;

-continued

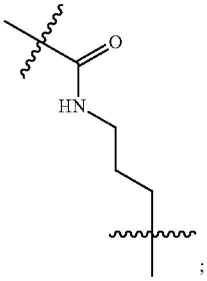

;

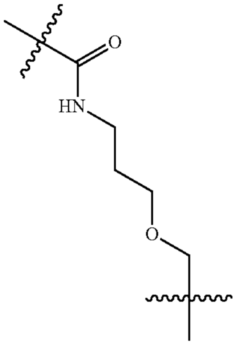

or

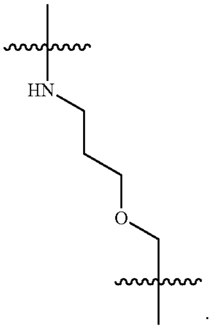

.

In more specific embodiments, at least one occurrence of $L^3$ or $L^{10}$ has one of the following structures:

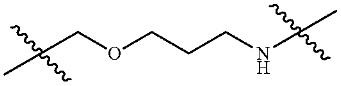

or

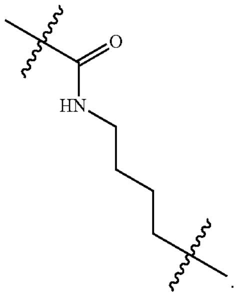

.

In some specific embodiments, each occurrence of $L^3$ or $L^{10}$ has one of the following structures:

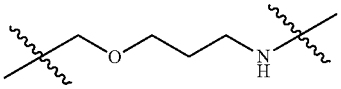

or

-continued

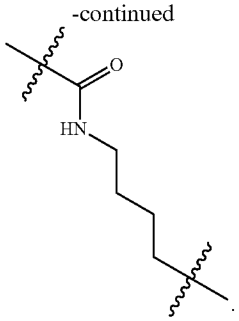

In some embodiments, each occurrence of $L^1$, $L^5$, or $L^9$ independently comprise a phosphodiester. In certain embodiments, at least one occurrence of $L^1$, $L^5$, or $L^9$ comprises ethylene oxide. In more specific embodiments, at least one occurrence of $L^1$, $L^5$, or $L^9$ comprises one of the following structures:

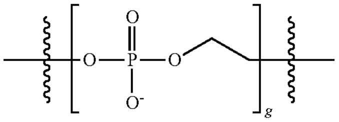

or

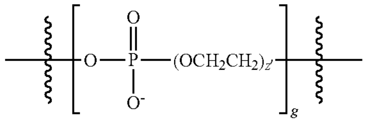

wherein:

g is an integer ranging from 1-10; and z' is an integer ranging from 1-30.

In some of the foregoing embodiments, z' is 3, 6, or 11-28. In some embodiments, g ranges from 2-5. In other more specific embodiments, at least one occurrence of $L^1$, $L^5$, or $L^9$ comprises the following structure:

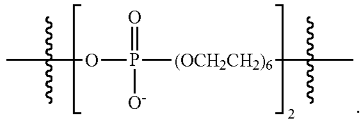

In certain embodiments, each occurrence of $L^1$, $L^5$, or $L^9$ comprises the following structure:

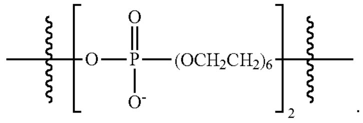

In other various embodiments, $R^2$ and $R^3$ are each independently OH or —OP(=$R_a$)($R_b$)$R_c$. In some different embodiments, $R^2$ or $R^3$ is OH or —OP(=$R_a$)($R_b$)$R_c$, and the other of $R^2$ or $R^3$ is Q or a linker comprising a covalent bond to Q. In some embodiments, $R^2$ and $R^3$ are each independently —OP(=$R_a$)($R_b$)$R_c$. In some specific embodiments, $R_c$ is OL'. In some of those embodiments, L' is a heteroalkylene linker to: Q, a targeting moiety, an analyte molecule, a solid support, a solid support residue, a nucleoside or a further compound of structure (I), (Ia), (Ib), (Ic), (Id), (Ie), ((III), (IIIa), (IIIb), (IIIc), or (IIId). In some embodiments, L' comprises an alkylene oxide or phosphodiester moiety, or combinations thereof. In certain embodiments, L' has the following structure:

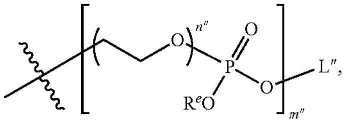

wherein:

m'' and n'' are independently an integer from 1 to 10;

$R^e$ is H, an electron pair or a counter ion;

$L^{11}$ is $R^e$ or a direct bond or linkage to: Q, a targeting moiety, an analyte molecule, a solid support, a solid support residue, a nucleoside or a further compound of structure (I), (Ia), (Ib), (Ic), (Id), (Ie), (III), (IIIa), (IIIb), (IIIc), or (IIId).

In still other embodiments, Q is, at each occurrence, independently a moiety comprising a reactive group capable of forming a covalent bond with an analyte molecule or a solid support (e.g., controlled pore glass or polystyrene beads). In other embodiments, Q is, at each occurrence, independently a moiety comprising a reactive group capable of forming a covalent bond with a complementary reactive group Q'. For example, in some embodiments, Q' is present on a further compound of (I), (Ia), (Ib), (Ic), (Id), (Ie), (III), (IIIa), (IIIb), (IIIc), or (IIId) (e.g., in the $R^2$ or $R^3$ position), and Q and Q' comprise complementary reactive groups such that reaction of the compound of structure (I), (Ia), (Ib), (Ic), (Id), (Ie), (III), (IIIa), (IIIb), (IIIc), or (IIId) and the further compound of structure (I), (Ia), (Ib), (Ic), (Id), (Ie), (III), (IIIa), (IIIb), (IIIc), or (IIId) results in covalently bound dimer of the compound of structure (I), (Ia), (Ib), (Ic), (Id), (Ie), (III), (IIIa), (IIIb), (IIIc), or (IIId). Multimer compounds of structures (I), (Ia), (Ib), (Ic), (Id), (Ie), (III), (IIIa), (IIIb), (IIIc), or (IIId) and combinations thereof can also be prepared in an analogous manner and are included within the scope of embodiments of the disclosure.

The type of Q group and connectivity of the Q group to the remainder of the compound of structure (I), (Ia), (Ib), (Ic), (Id), (Ie), (III), (IIIa), (IIIb), (IIIc), or (IIId) is not particularly limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule (e.g., a biomolecule) or solid support (e.g., an amine, azide, or alkyne).

Certain embodiments of compounds of structure (I), (Ia), (Ib), (Ic), (Id), (Ie), (III), (IIIa), (IIIb), (IIIc), and/or (IIId) comprise Q groups commonly employed in the field of bio-conjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino, or maleimide functional group. In some embodiments, the activated ester is an N-succinimide ester, imidoester, or polyflourophenyl ester. In other embodiments, the alkyne is an alkyl azide or acyl azide. In some embodiments, Q comprises a maleimide functional group.

Exemplary Q moieties are provided in Table I below.
TABLE 1
| Exemplary Q Moieties | |
|---|---|
| Structure | Class |
| 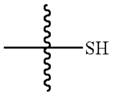 | Sulfhydryl |
| 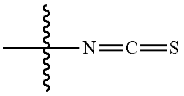 [SMILES: *N=C=S] | Isothiocyanate |
| 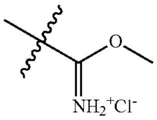 | Imidoester |
| 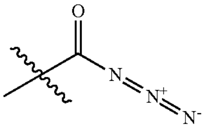 [SMILES: *C(=O)N=[N+]=[N-]] | Acyl Azide |
| 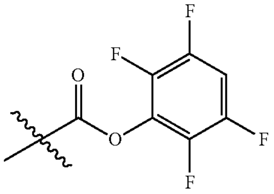 [SMILES: *C(=O)Oc1c(F)c(F)cc(F)c1F] | Activated Ester |
| 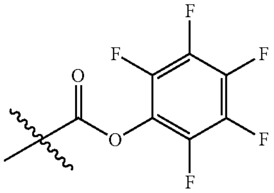 [SMILES: *C(=O)Oc1c(F)c(F)c(F)c(F)c1F] | Activated Ester |
| 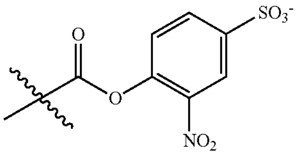 | Activated Ester |
| 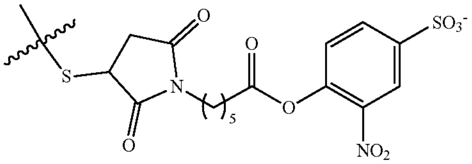 | Activated Ester |
| 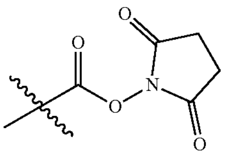 [SMILES: *C(=O)ON1C(=O)CCC1=O] | Activated Ester |

TABLE 1-continued
| Exemplary Q Moieties | |
|---|---|
| Structure | Class |
| 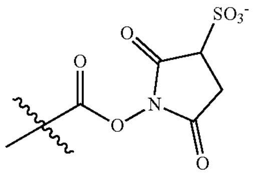 | Activated Ester |
| 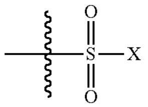 X = halo | Sulfonyl halide |
| 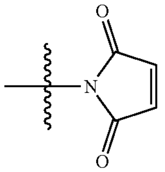 [SMILES: *N1C(=O)C=CC1=O] | Maleimide |
| 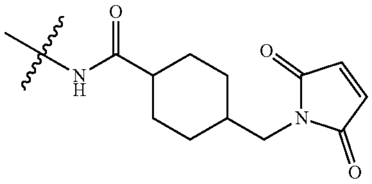 [SMILES: *NC(=O)C1CCC(CN2C(=O)C=CC2=O)CC1] | Maleimide |
| 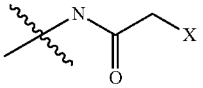 X = halo | α-haloimide |
| 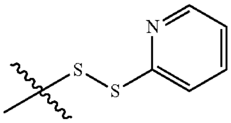 [SMILES: *SSc1ccccn1] | Disulfide |
| 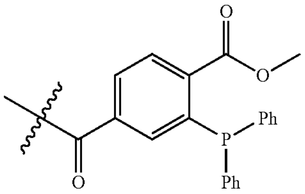 [SMILES: *C(=O)c1ccc(C(=O)OC)c(P(c2ccccc2)c2ccccc2)c1] | Phosphine |
| 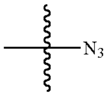 [SMILES: *N=[N+]=[N-]] | Azide |
| 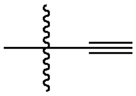 | Alkyne |

TABLE 1-continued

| Exemplary Q Moieties | |
|---|---|
| Structure | Class |
| 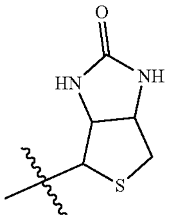 [SMILES: *C1SCC2NC(=O)NC21] | Biotin |
| 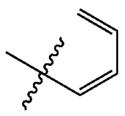 [SMILES: */C=C\C=C] | Diene |
| 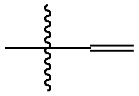 [SMILES: *C=C] | Alkene/dienophile |
| 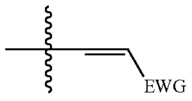<br>EWG = eletron withdrawing group | Alkene/dienophile |
| —$NH_2$ | Amino |

It should be noted that in some embodiments, wherein Q is SH, the SH moiety will tend to form disulfide bonds with another sulfhydryl group on another compound of structure (I), (Ia), (Ib), (Ic), (Id), (Ie), (III), (IIIa), (IIIb), (IIIc), or (IIId).

Accordingly, some embodiments include compounds of structure (I), (Ia), (Ib), (Ic), (Id), (Ie), (III), (IIIa), (IIIb), (IIIc), or (IIId) which are in the form of disulfide dimers, the disulfide bond being derived from SH Q groups.

In some other embodiments, one of $R^2$ or $R^3$ is OH or —OP(=$R_a$)($R_b$)$R_c$, and the other of $R^2$ or $R^3$ is a linker comprising a covalent bond to an analyte molecule or a linker comprising a covalent bond to a solid support. For example, in some embodiments the analyte molecule is a nucleic acid or a polymer thereof or an amino acid or a polymer thereof. In other embodiments, the analyte molecule is an enzyme, receptor, receptor ligand, antibody, glycoprotein, aptamer or prion. In still different embodiments, the solid support is a polymeric bead or non-polymeric bead. In some embodiments, the targeting moiety is an antibody or cell surface receptor antagonist.

In certain specific embodiments, $R^2$ or $R^3$ has one of the following structures:

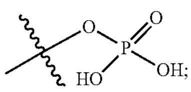

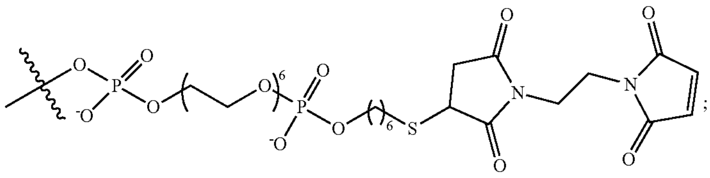

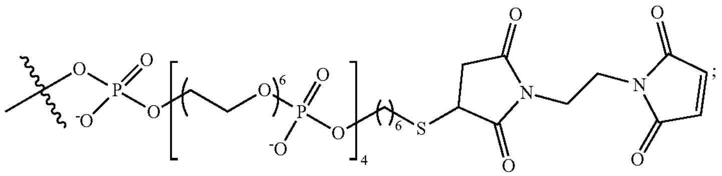

-continued

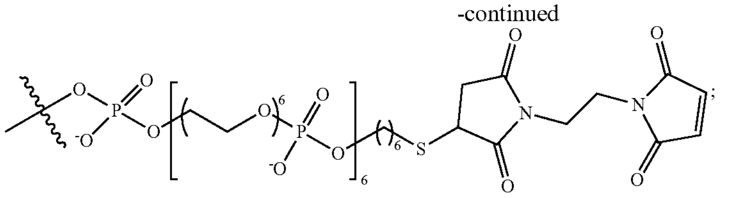

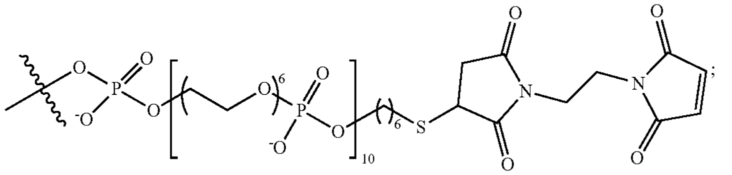

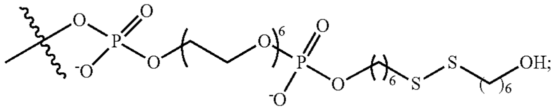

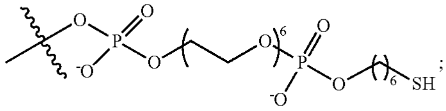

or

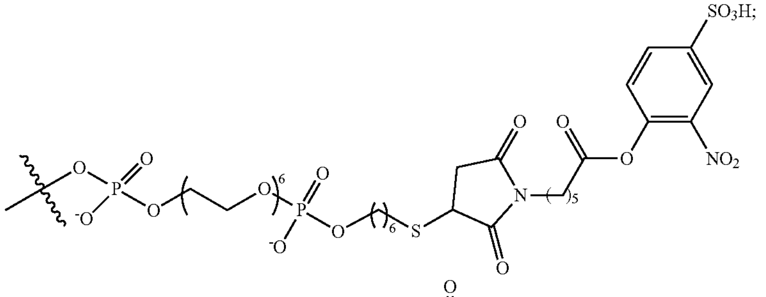

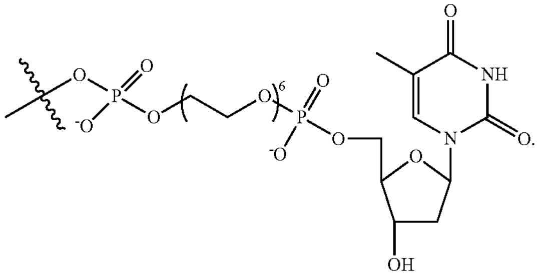

In some embodiments, one of $R^2$ or $R^3$ is OH or —OP(═$R_a$)($R_b$)$R_c$, and the other of $R^2$ or $R^3$ comprises the following structure:

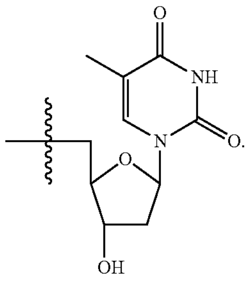 [SMILES: *CC1OC(n2cc(C)c(=O)[nH]c2=O)CC1O]

In some embodiments, at least one occurrence of $M^3$ is an alkylating agent, an antimetabolite, a microtubule inhibitor, a topoisomerase inhibitor, or a cytotoxic antibiotic. In some more specific embodiments, each occurrence of $M^3$ is an alkylating agent, an antimetabolite, a microtubule inhibitor, a topoisomerase inhibitor, or a cytotoxic antibiotic.

In certain embodiments, at least one occurrence of $M^3$ is a nitrogen mustard, a nitrosourea, a tetrazine, an aziridine, a cisplatin or cisplatin derivative, or a non-classical alkylating agent. In more specific embodiments, at least one occurrence of $M^3$ is mechlorethamine, cyclophosphamide, melphalan, chlorambucil, ifosfamide, busulfan, N-nitroso-N-methylurea (MNU), carmustine (BCNU), lomustine (CCNU), semustine (MeCCNU), fotemustine, streptozotocin, dacarbazine, mitozolomide, temozolomide, thiotepa, mytomycin, diaziquone (AZQ), cisplatin, carboplatin, oxaliplatin, procarbazine, or hexamethylmelamine. In some embodiments, at least one occurrence of $M^3$ is an anti-folate, a fluoropyrimidines, a deoxynucleoside analogue, or a thiopurine. In certain embodiments, at least one occurrence of $M^3$ is methotrexate, pemetrexed, fluorouracil, capecitabine, cytarabine, gemcitabine, decitabine, azacitidine, fludarabine, nelarabine, cladribine, clofarabine, pentostatin, thioguanine, and mercaptopurine. In some specific embodiments, at least one occurrence of $M^3$ is an auristatin, a Vinca alkaloid, or a taxane. In certain specific embodiments, at least one occurrence of $M^3$ is auristatin F, auristatin E, vincristine, vinblastine, vinorelbine, vindesine, vinflunine, paclitaxel, docetaxel, etoposide, or teniposide. In some more specific embodiments, at least one occurrence of $M^3$ is irinotecan, SN 38, topotecan, camptothecin, doxorubicin, mitoxantrone, teniposide, novobiocin, merbarone, or aclarubicin. In certain more specific embodiments, at least one occurrence of $M^3$ is an anthracycline or a bleomycin. In some embodiments, at least one occurrence of $M^3$ is doxorubicin, daunorubicin, epirubicin, idarubicin, pirarubicin, aclarubicin, or mitoxantrone. In some embodiments, at least one occurrence of $M^3$ is auristatin F, monomethyl auristatin F, monomethyl auristatin E, paciltaxol, SN-38, calicheamicin, anthramycin, abbeymycin, chicamycin, DC-81, mazethramycin, neothramycin A, neothramycin B, porothramycin prothracarcin, sibanomicin, sibiromycin, tomamycin, mertansine, emtansine, irinotecan, camptothecin, topotecan, silatecan, cositecan, Exatecan, Lurtotecan, gimatecan, Belotecan, and Rubitecan. In some embodiments, each occurrence of $M^3$ is auristatin F, monomethyl auristatin F, monomethyl auristatin E, paciltaxol, SN-38, calicheamicin, anthramycin, abbeymycin, chicamycin, DC-81, mazethramycin, neothramycin A, neothramycin B, porothramycin prothracarcin, sibanomicin, sibiromycin, tomamycin, mertansine, emtansine, irinotecan, camptothecin, topotecan, silatecan, cositecan, Exatecan, Lurtotecan, gimatecan, Belotecan, and Rubitecan.

In certain embodiments, at least one occurrence of $M^3$ has the following structure:

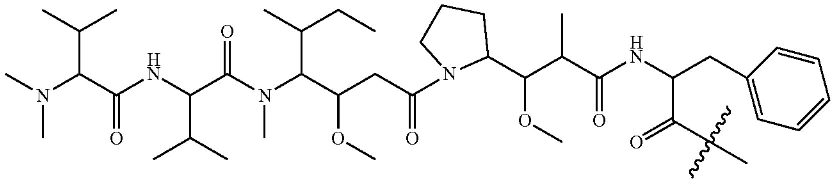 [SMILES: *C(=O)C(Cc1ccccc1)NC(=O)C(C)C(OC)C1CCCN1C(=O)CC(OC)C(C(C)CC)N(C)C(=O)C(NC(=O)C(C(C)C)N(C)C)C(C)C]

In some specific embodiments, each occurrence of $M^3$ has the following structure:

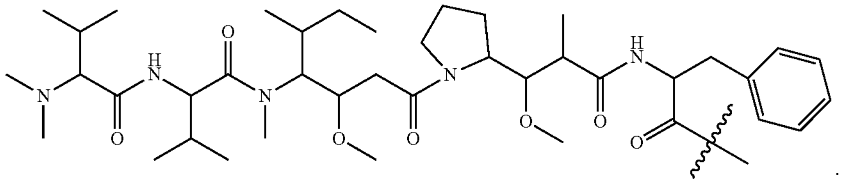 [SMILES: *C(=O)C(Cc1ccccc1)NC(=O)C(C)C(OC)C1CCCN1C(=O)CC(OC)C(C(C)CC)N(C)C(=O)C(NC(=O)C(C(C)C)N(C)C)C(C)C]

In certain embodiments, at least one occurrence of $-L^{10}-M^3$ has the following structure:

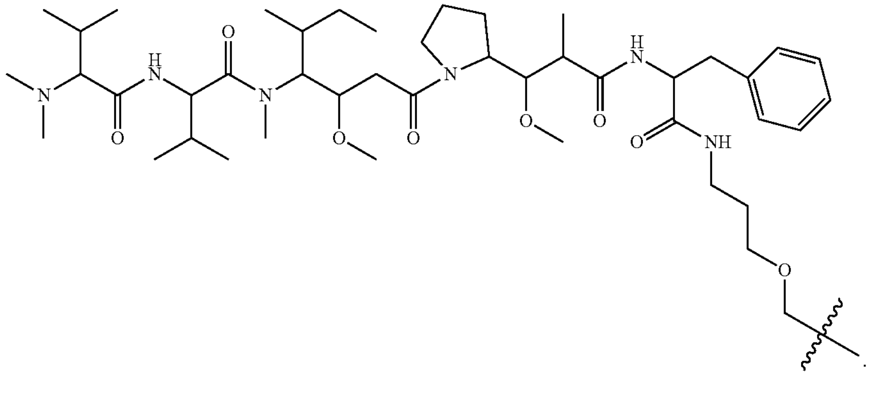 [SMILES: *COCCCNC(=O)C(Cc1ccccc1)NC(=O)C(C)C(OC)C1CCCN1C(=O)CC(OC)C(C(C)CC)N(C)C(=O)C(NC(=O)C(C(C)C)N(C)C)C(C)C]

In certain embodiments, each occurrence of $-L^{10}-M^3$ has the following structure:
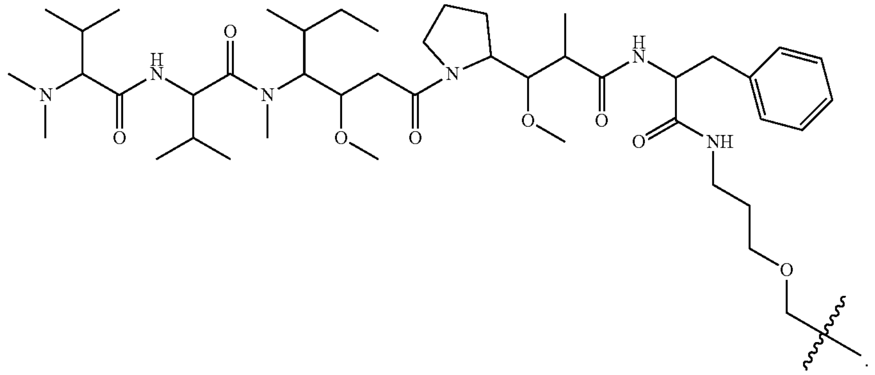 [SMILES: *COCCCNC(=O)C(Cc1ccccc1)NC(=O)C(C)C(OC)C1CCCN1C(=O)CC(OC)C(C(C)CC)N(C)C(=O)C(NC(=O)C(C(C)C)N(C)C)C(C)C]
In certain embodiments, at least one occurrence of $M^3$ has the following structure:
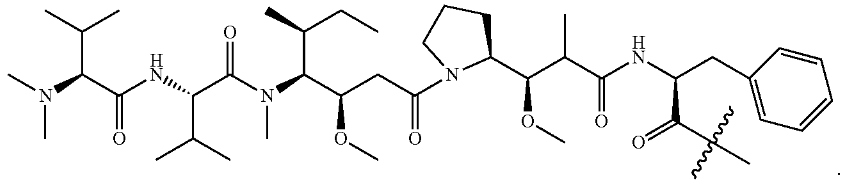 [SMILES: *C(=O)[C@H](Cc1ccccc1)NC(=O)C(C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C]
In some specific embodiments, each occurrence of $M^3$ has the following structure:
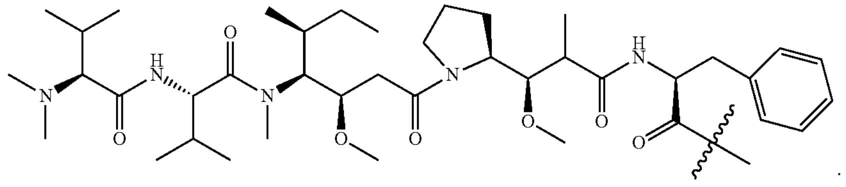 [SMILES: *C(=O)[C@H](Cc1ccccc1)NC(=O)C(C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C]
In certain embodiments, at least one occurrence of $-L^{10}-M^3$ has the following structure:
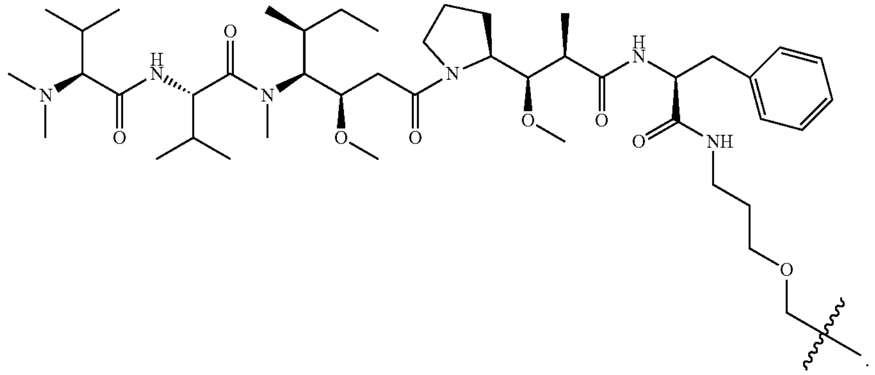 [SMILES: *COCCCNC(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C]

In certain embodiments, each occurrence of $-L^{10}-M^3$ has the following structure:

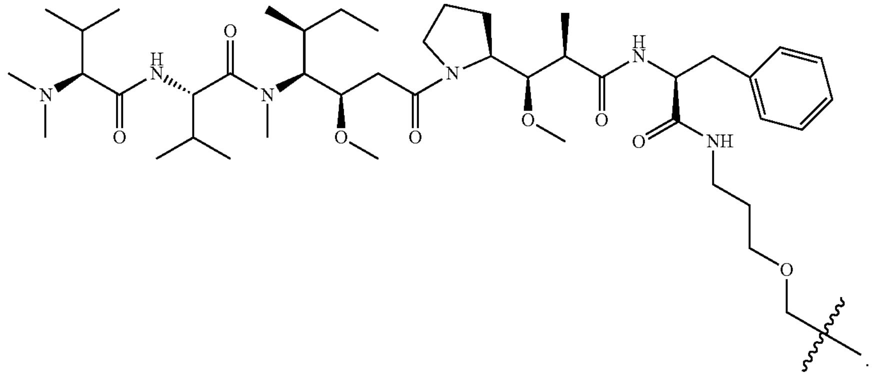 [SMILES: *COCCCNC(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C]
.

In still other embodiments of any of the foregoing, $M^1$, at each occurrence, independently comprises two or more aryl or heteroaryl rings, or combinations thereof, for example three or more or four or more aryl or heteroaryl rings, or combinations thereof, or even five or more aryl or heteroaryl rings, or combinations thereof. In some embodiments, $M^1$, at each occurrence, independently comprises six aryl or heteroaryl rings, or combinations thereof. In further embodiments, the rings are fused. For example in some embodiments, $M^1$, at each occurrence, independently comprises two or more fused rings, three or more fused rings, four or more fused rings, five or more fused rings, or even six or more fused rings. In some more specific embodiments, $M^1$, at each occurrence, independently comprises a fused-multicyclic aryl moiety comprising at least two fused rings.

In certain specific embodiments, $M^1$ is, at each occurrence, independently selected from the group consisting of a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9,10-ethynylanthracene, and ter-naphthyl moiety.

In some embodiments, $M^1$ is, at each occurrence, independently selected from the group consisting of p-terphenyl, perylene, azobenzene, phenazine, phenanthroline, acridine, thioxanthrene, chrysene, rubrene, coronene, cyanine, perylene imide, perylene amide, and derivatives thereof. In some embodiments, $M^1$ is, at each occurrence, independently selected from the group consisting of a coumarin dye, resorufin dye, dipyrrometheneboron difluoride dye, ruthenium bipyridyl dye, thiazole orange dye, polymethine, and N-aryl-1,8-naphthalimide dye. In certain embodiments, $M^1$, $M^2$, or $M^3$ are, at each occurrence, independently selected from the group consisting of a coumarin dye, boron-dipyrromethene, rhodamine, cyanine, pyrene, perylene, perylene monoimide, 6-FAM, 5-FAM, 6-FITC, 5-FITC, and derivatives thereof. In certain embodiments, $M^1$, at each occurrence, independently has one of the following structures:

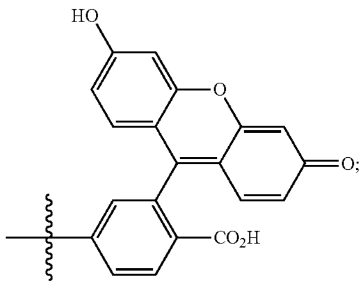

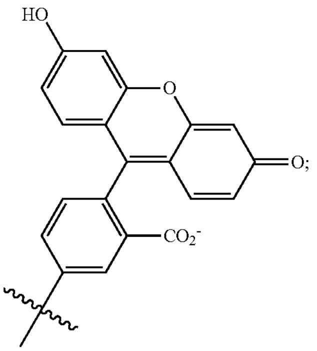

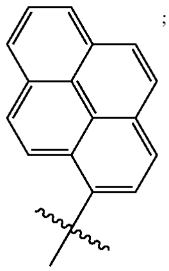
;

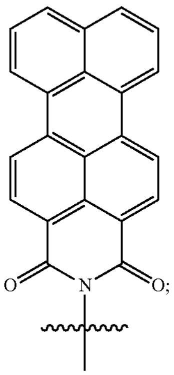

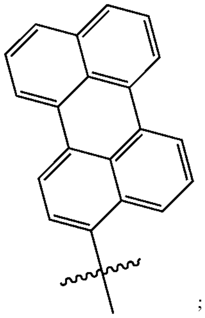
;

-continued
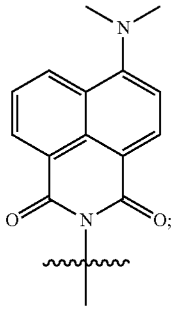
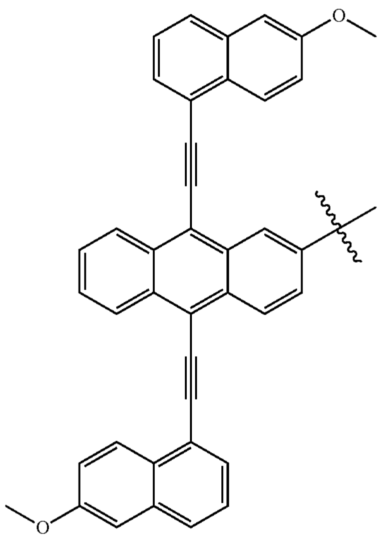
or
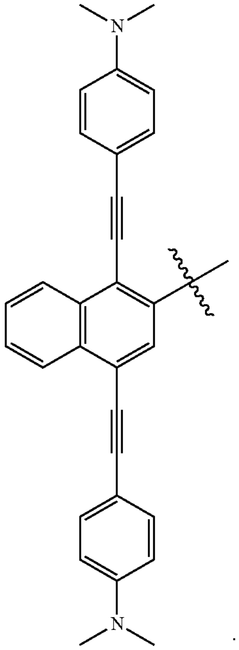
.
In some more specific embodiments, at least one occurrence of $M^1$ has the following structure:
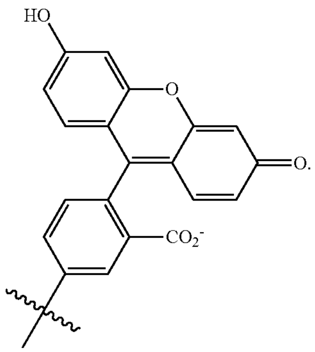
In some more specific embodiments, each occurrence of $M^1$ has the following structure:
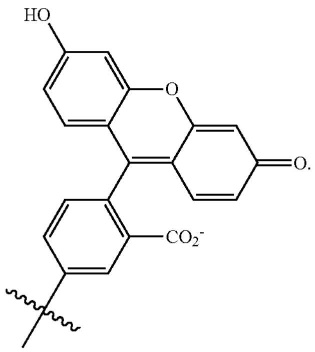
In some more specific embodiments, at least one occurrence of $-L^3-M^1$ has the following structure:
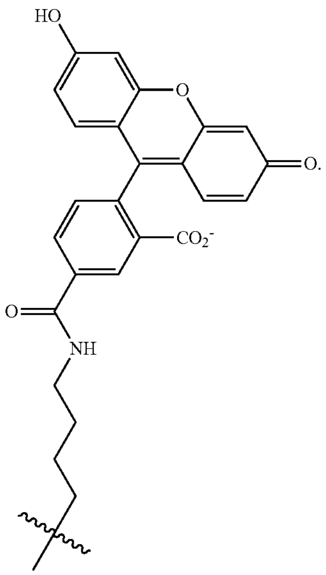

In some more specific embodiments, each occurrence of $-L^3-M^1$ has the following structure:

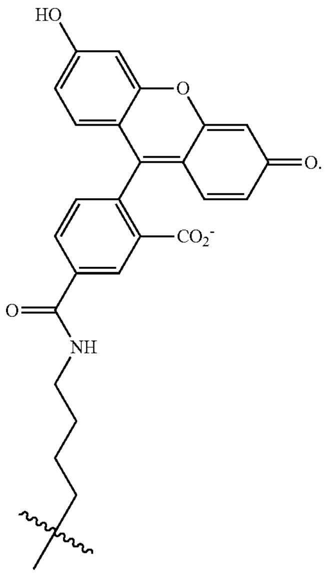

Compounds of the present disclosure (e.g., compounds of Structure (I), (Ia), (Ib), (Ic), (Id), (Ie), (III), (IIIa), (IIIb), (IIIc), or (IIId) are useful partly because they may be attached to a targeting molecule (e.g., an antibody or fragment thereof). Such an attachment may be made by reducing a disulfide bond of a compound of Structure (I), (Ia), (Ib), (Ic), (Id), (Ie), (III), (IIIa), (IIIb), (IIIc), or (IIId) with an appropriate reagent (e.g., TCEP) and coupling the resultant molecule to an appropriate linker reagent (e.g., 1,1'-(ethane-1,2-diyl)bis(1H-pyrrole-2,5-dione) which is commonly known as bis-maleimidoethane or "BMOE"). The resultant product can then be coupled to a targeting molecule (e.g., an antibody or fragment thereof) having a free thiol (—SH) group (e.g., present via reduction of a disulfide bond of the targeting molecule).

Accordingly, in some embodiments, $R^2$ comprises the following structure:

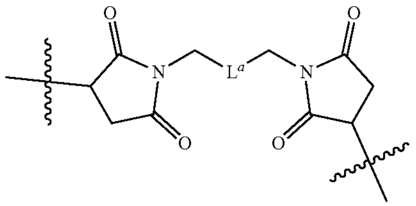

wherein:

$L^a$ is a direct bond or $C_1$-$C_6$ alkylene. In some embodiments, $L^a$ is a direct bond In some embodiments, $R^2$ further comprises a covalent bond to an antibody (e.g., monoclonal antibody such as brentuximab, gemtuzumab, trastuzumab, inotuzumab, polatuzumab, enfortumab, trastuzumab, sacituzumab, belantamab, moxetumomab, etc.) or fragment thereof. For example, in some embodiments, $R^2$ comprises the following structure:

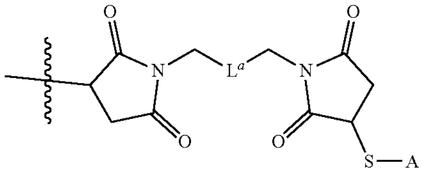

wherein:

A is an antibody (e.g., monoclonal antibody such as brentuximab, gemtuzumab, trastuzumab, inotuzumab, polatuzumab, enfortumab, trastuzumab, sacituzumab, belantamab, or moxetumomab). In some related embodiments, $L^a$ is a direct bond. In some embodiments, $R^2$ has the following structure:

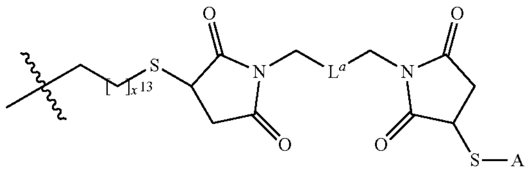

wherein:

$x^{13}$ is 0 or an integer greater than 0 (e.g., 1, 2, 3, 4, 5, 6, 7, 8, 9, 10, 11, or 12).

In some embodiments, a compound of Structure (I), (Ia), (Ib), (Ic), (Id), (Ie), (III), (IIIa), (IIIb), (IIIc), or (IIId) has m from 0 to 10. In certain embodiments, a compound of Structure (I), (Ia), (Ib), (Ic), (Id), or (Ie) has m being 0, 1, 2, 3, 4, or 5.

In some embodiments, a compound of Structure (I), (Ia), (Ib), (Ic), (Id), (Ie), (III), (IIIa), (IIIb), (IIIc), or (IIId) has n being 1, 2, 3, or 4. In certain embodiments, a compound of Structure (I), (Ia), (Ib), (Ic), (Id), (Ie), (III), (IIIa), (IIIb), (IIIc), or (IIId) has n being 1 or 2.

In some embodiments, a compound of Structure (I), (Ia), (Ib), (Ic), (Id), (Ie), (III), (IIIa), (IIIb), (IIIc), or (IIId) has p being 1, 2, 3, or 4. In certain embodiments, a compound of Structure (I), (Ia), (Ib), (Ic), (Id), (Ie), (III), (IIIa), (IIIb), (IIIc), or (IIId) has p being 1 or 2.

In some more specific embodiments, a compound of Structure (I), (Ia), (Ib), (Ic), (Id), (Ie), (III), (IIIa), (IIIb), (IIIc), or (IIId) has m being 0, n being 1, and p being 2. In some more specific embodiments, a compound of Structure (I), (Ia), (Ib), (Ic), (Id), (Ie), (III), (IIIa), (IIIb), (IIIc), or (IIId) has m being 1, n being 1, and p being 2. In some more specific embodiments, a compound of Structure (I), (Ia), (Ib), (Ic), (Id), (Ie), (III), (IIIa), (IIIb), (IIIc), or (IIId) has m being 5, n being 1, and p being 2.

In some more specific embodiments, a compound of Structure (I), (Ia), (Ib), (Ic), (Id), (Ie), (III), (IIIa), (IIIb), (IIIc), or (IIId), wherein at least one occurrence of $R^6$ or $R^7$ is F. In certain embodiments, a compound of Structure (I), (Ia), (Ib), (Ic), (Id), (Ie), (III), (IIIa), (IIIb), (IIIc), or (IIId), wherein each one occurrence of $R^6$ and $R^7$ are F.

In some more specific embodiments, a compound of Structure (I), (Ia), (Ib), (Ic), (Id), (Ie), (III), (IIIa), (IIIb), (IIIc), or (IIId), wherein at least each occurrence of $R^6$ and $R^7$ are F, $R^8$ is O, $R^9$ is H, and $R^{10}$ is H. In some more specific embodiments, a compound of Structure (I), (Ia), (Ib), (Ic), (Id), (Ie), (III), (IIIa), (IIIb), (IIIc), or (IIId), wherein at least each occurrence of $R^6$ and $R^7$ are H, $R^8$ is O, $R^9$ is C(═O)$OCH_2CH_2CH_2CH_2CH_3$, and $R^{10}$ is F.

In some more specific embodiments, a compound of Structure (I), (Ia), (Ib), (Ic), (Id), (Ie), (III), (IIIa), (IIIb), (IIIc), or (IIId), wherein $x^a$, $x^b$, $x^c$, $x^d$, $x^e$, and $x^f$ are, at each occurrence, independently an integer of 0 or 1. In some more specific embodiments, a compound of Structure (I), (Ia), (Ib), (Ic), (Id), (Ie), (III), (IIIa), (IIIb), (IIIc), or (IIId), wherein q is 0 or 1.

In some embodiments, a method of treating a disease or disorder, comprising administering a therapeutically effective amount of, a compound of Structure (I), (Ia), (Ib), (Ic), (Id), (Ie), (III), (IIIa), (IIIb), (IIIc), or (IIId), or the pharmaceutical composition of the compound of Structure (I), (Ia), (Ib), (Ic), (Id), (Ie), (III), (IIIa), (IIIb), (IIIc), or (IIId), to a subject in need thereof is disclosed. In some more specific embodiments, the disease or disorder is cancer which includes breast cancer, stomach cancer, lung cancer, ovarian cancer, lymphoma, and bladder cancer.

In some embodiments, a compound of Structure (III) has Auristatin F moiety (labeled as "AF") and gemcitabine moiety switched compared to Structure (I), (Ia), (Ib), (Ic), or (Id). For example, the compound of Structure (III) with AF moiety and gemcitabine moiety switched is shown as compound I-13 on Table 2 and can be prepared according to the procedures described in the present disclosure.

In some specific embodiments, a compound of Structure (I), (Ia), (Ib), (Ic), (Id), (Ie), (III), (IIIa), (IIIb), (IIIc), or (IIId) is a compound selected from Table 2. The compounds in Tables 2 and 3 were prepared according to the procedures set forth in the Examples.

TABLE 2

Exemplary Compounds of Structures (I), (Ia), (Ib), (Ic), (Id), (Ie), (III), (IIIa), (IIIb), (IIIc), or (IIId)

| Nos. | Structure |
|---|---|
| I-1 | 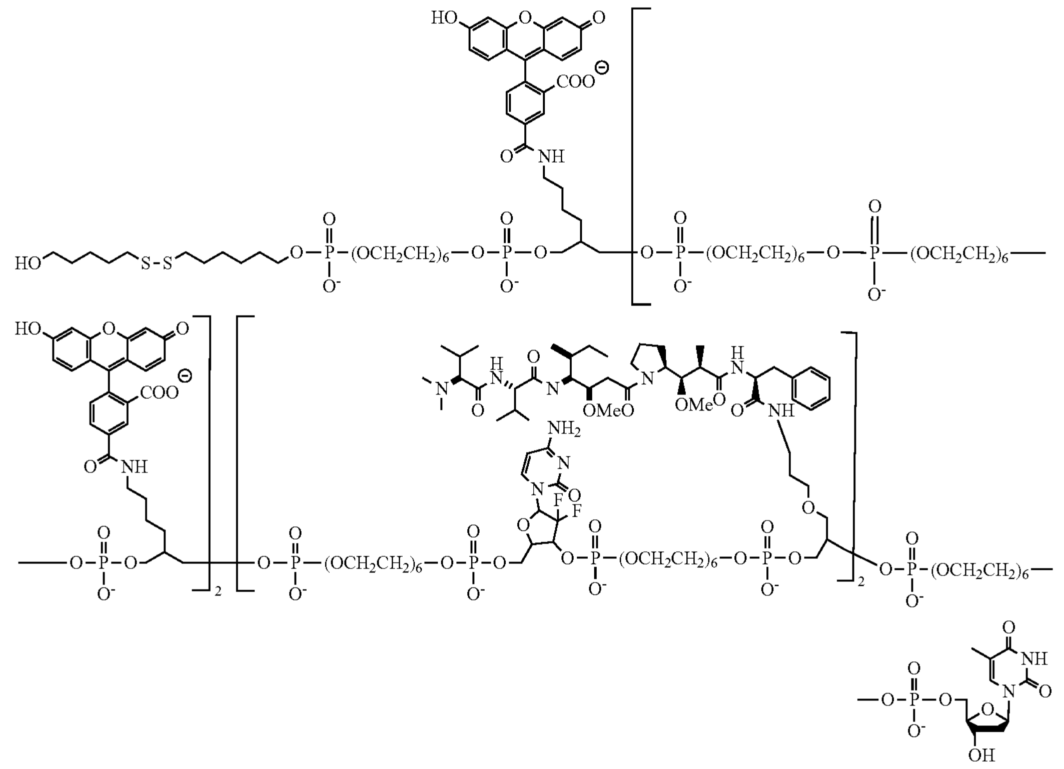 Chemical Formula: $C_{335}H_{522}F_4N_{23}O_{165}P_{18}S_2^{21-}$ Molecular Weight: 8209.51 |
| I-2 | 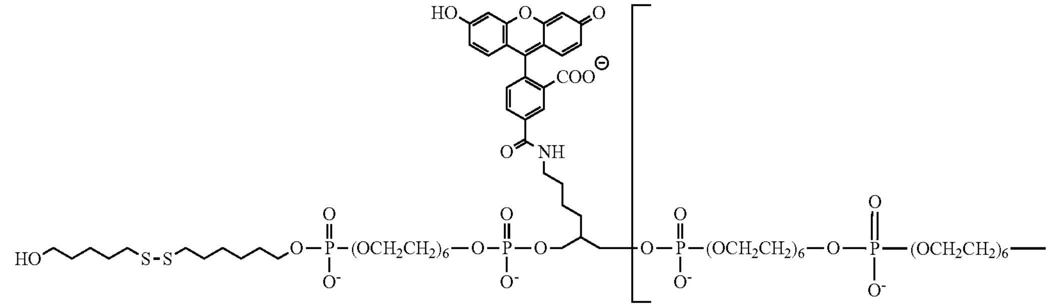 |

TABLE 2-continued
| Exemplary Compounds of Structures (I), (Ia), (Ib), (Ic), (Id), (Ie), (III), (IIIa), (IIIb), (IIIc), or (IIId) | |
|---|---|
| Nos. | Structure |
| | 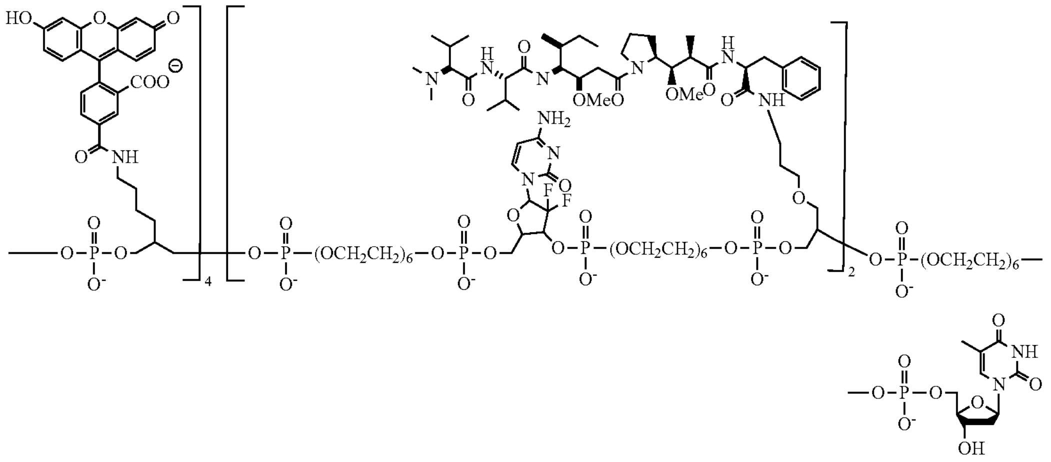<br>Chemical Formula: $C_{440}H_{668}F_4N_{25}O_{221}P_{24}S_2^{29-}$<br>Molecular Weight: 10727.64 |
| I-3 | 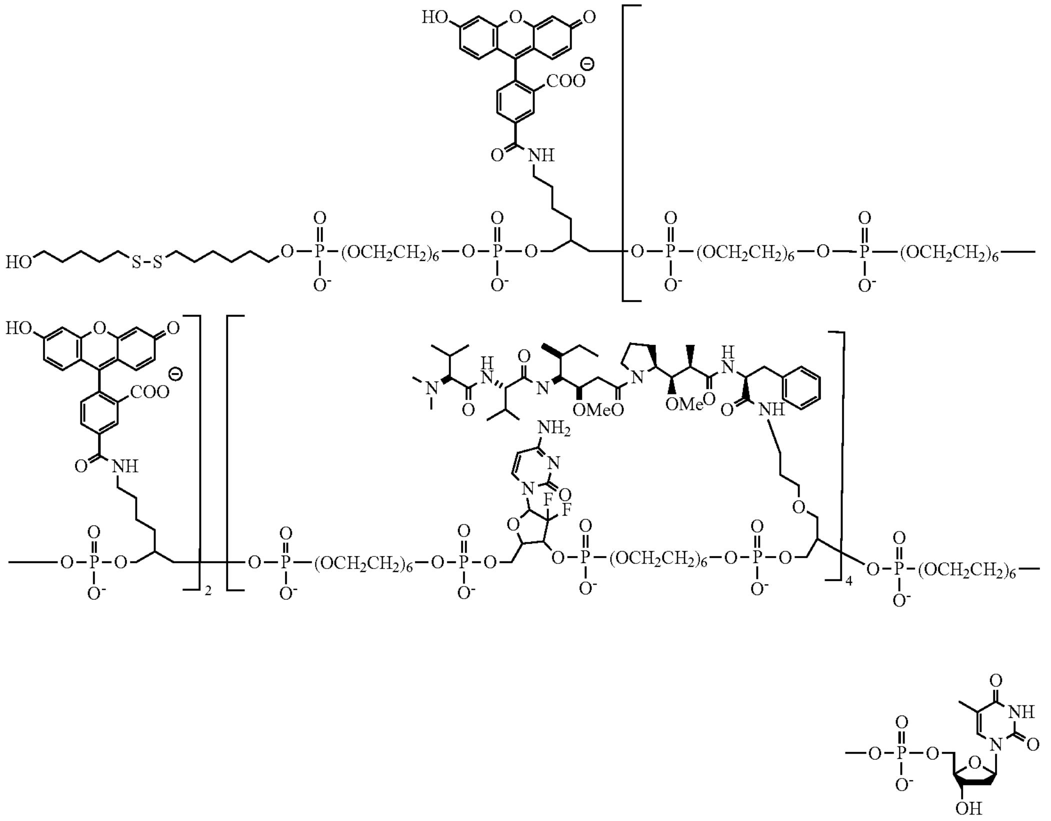<br>Chemical Formula: $C_{493}H_{792}F_8N_{41}O_{237}P_{26}S_2^{29-}$<br>Molecular Weight: 12107.25 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
|---|---|
| I-4 | 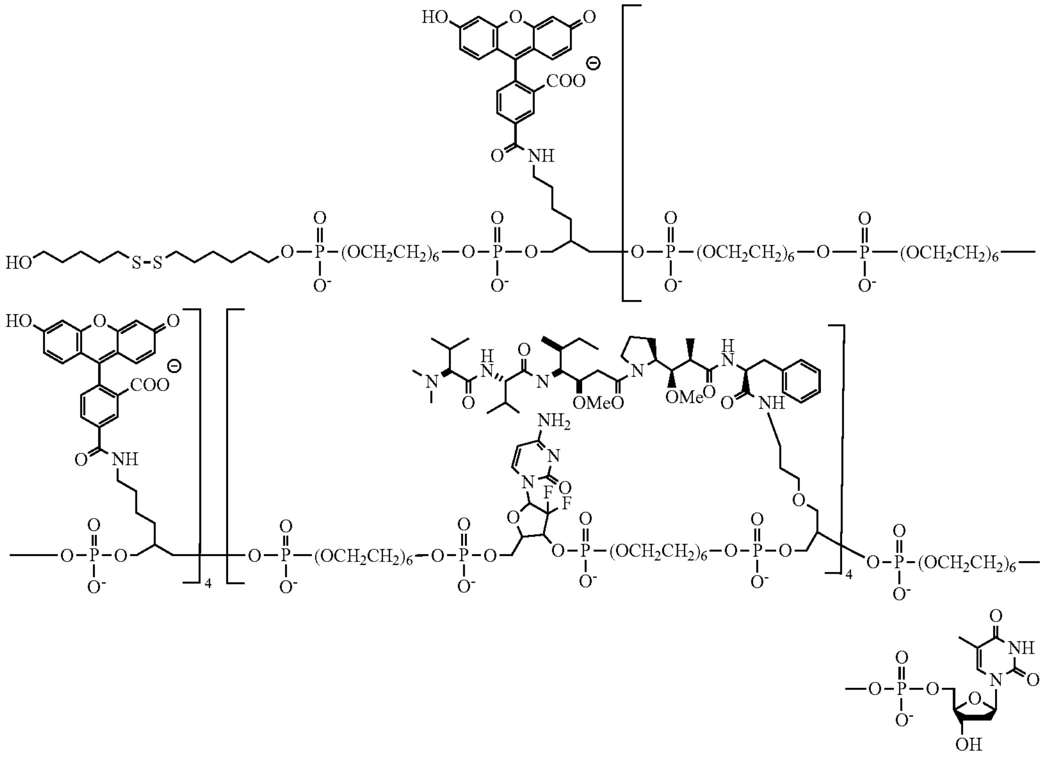<br>Chemical Formula: $C_{597}H_{936}F_8N_{43}O_{293}P_{32}S_2^{37-}$<br>Molecular Weight: 14611.35 |
| I-5 | 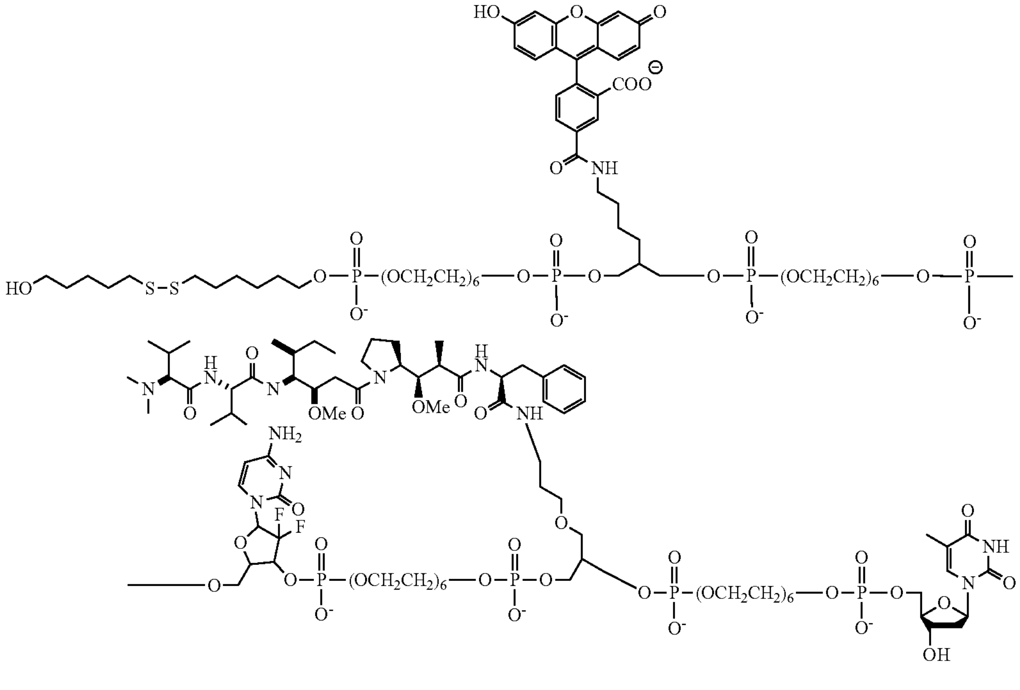<br>Chemical Formula: $C_{152}H_{243}F_2N_{12}O_{73}P_8S_2^{9-}$<br>Molecular Weight: 3756.54 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
|---|---|
| I-6 | 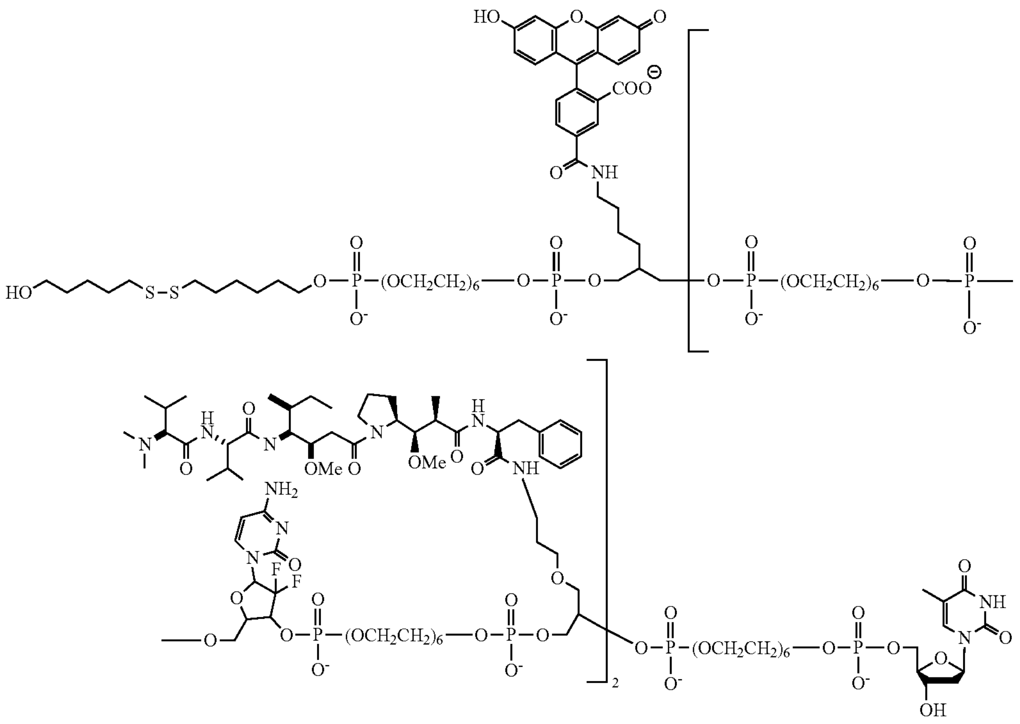<br>Chemical Formula: $C_{232}H_{380}F_4N_{21}O_{109}P_{12}S_2^{13-}$<br>Molecular Weight: 5719.39 |
| I-7 | 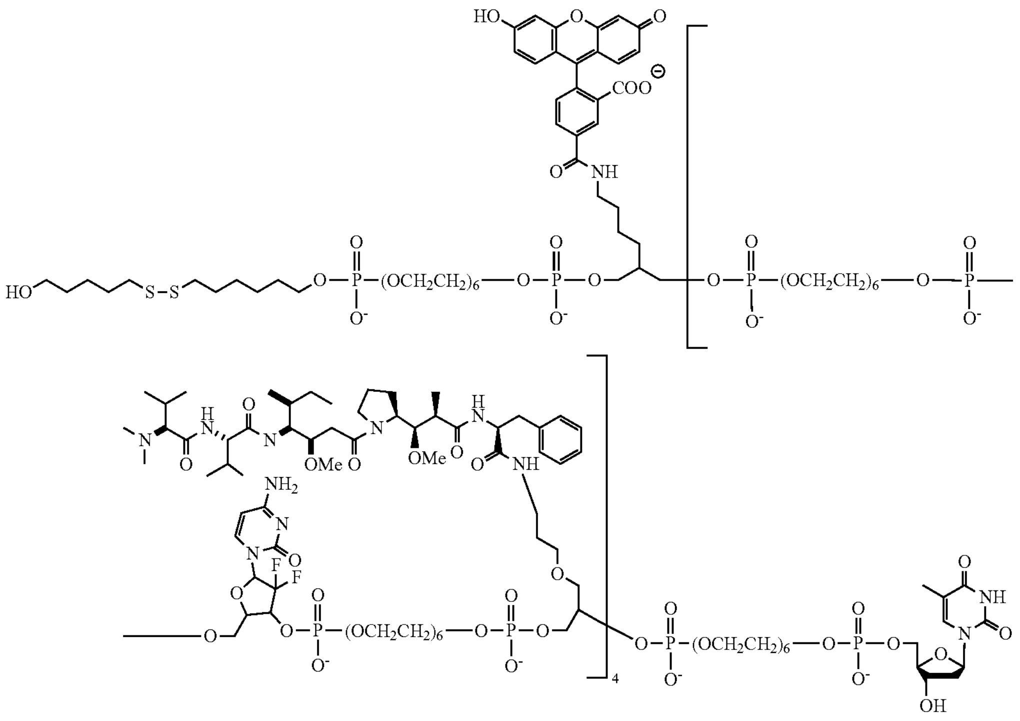<br>Chemical Formula: $C_{389}H_{648}F_8N_{39}O_{181}P_{20}S_2^{21-}$<br>Molecular Weight: 9603.15 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
| --- | --- |
| I-8 | 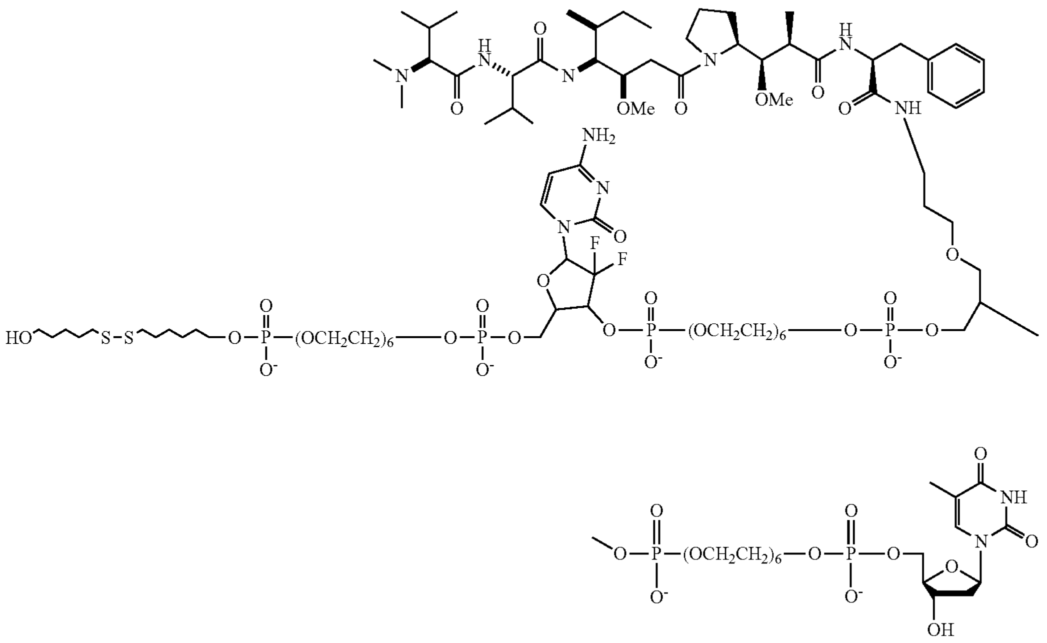 Chemical Formula: $C_{112}H_{195}F_2N_{11}O_{54}P_6S_2^{6-}$ Molecular Weight: 2848.78 |
| I-9 | 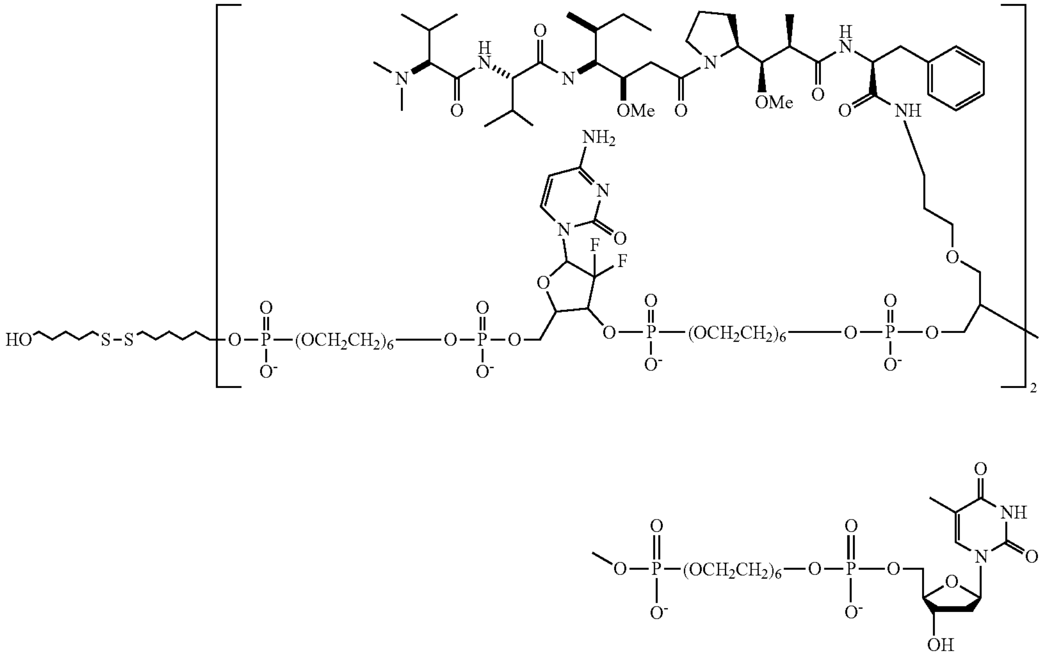 Chemical Formula: $C_{192}H_{332}F_4N_{20}O_{90}P_{10}S_2^{10-}$ Molecular Weight: 4810.64 |

TABLE 2-continued
Exemplary Compounds of Structures (I), (Ia), (Ib), (Ic), (Id), (Ie), (III), (IIIa), (IIIb), (IIIc), or (IIId)
Nos. Structure
I-10
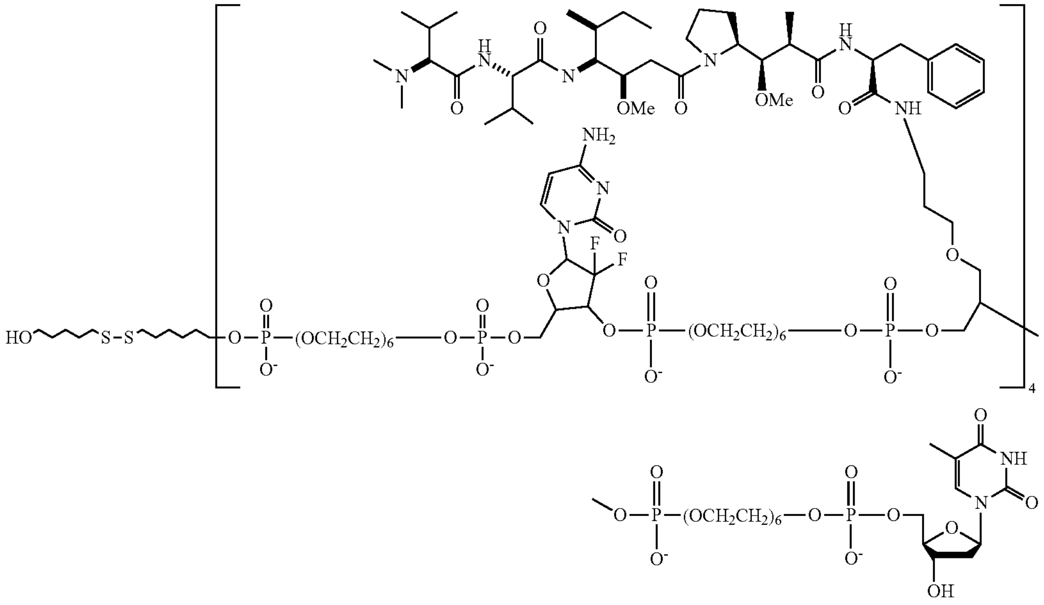
Chemical Formula: $C_{350}H_{602}F_8N_{38}O_{162}P_{18}S_2^{18-}$
Molecular Weight: 8708.34
I-11
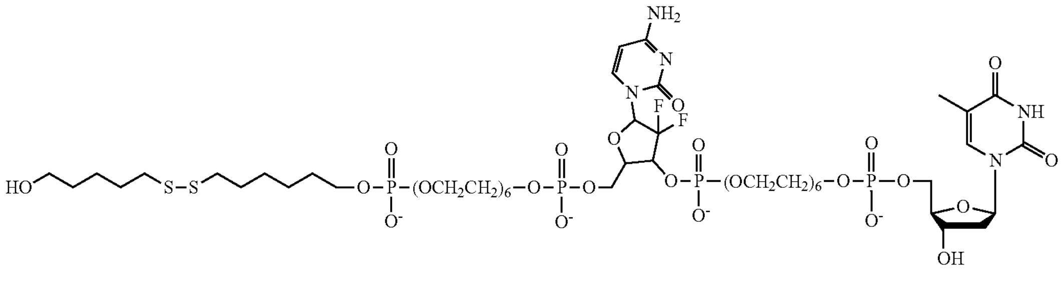
Chemical Formula: $C_{54}H_{93}F_2N_5O_{33}P_4S_2^{4-}$
Molecular Weight: 1566.35
I-12
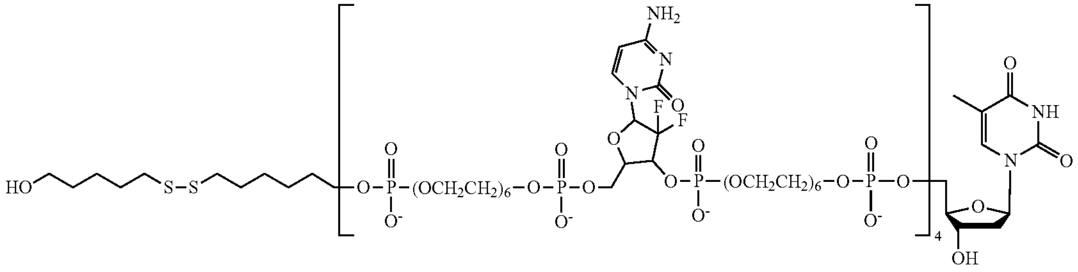
Chemical Formula: $C_{153}H_{264}F_8N_{14}O_{117}P_{16}S_2^{16-}$
Molecular Weight: 4883.47

TABLE 2-continued
| Exemplary Compounds of Structures (I), (Ia), (Ib), (Ic), (Id), (Ie), (III), (IIIa), (IIIb), (IIIc), or (IIId) | |
|---|---|
| Nos. | Structure |
| I-13 | 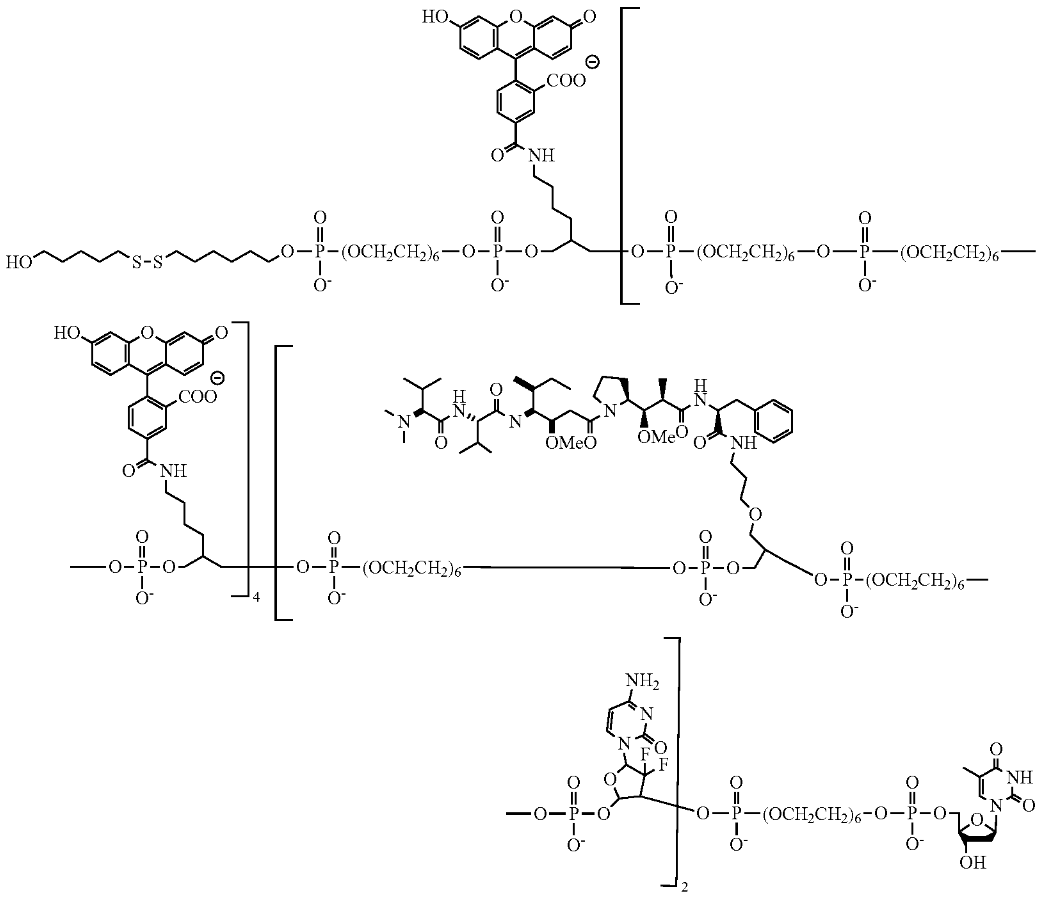 |
| I-14 | 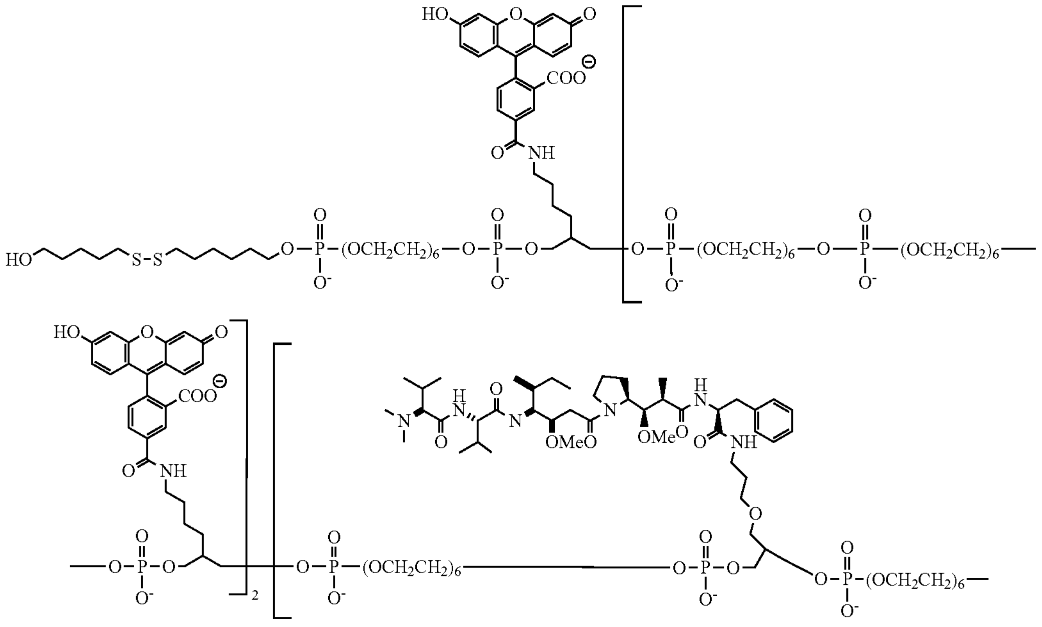 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
| --- | --- |
| | 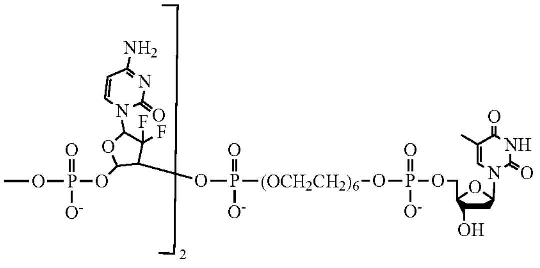 |
| I-15 | 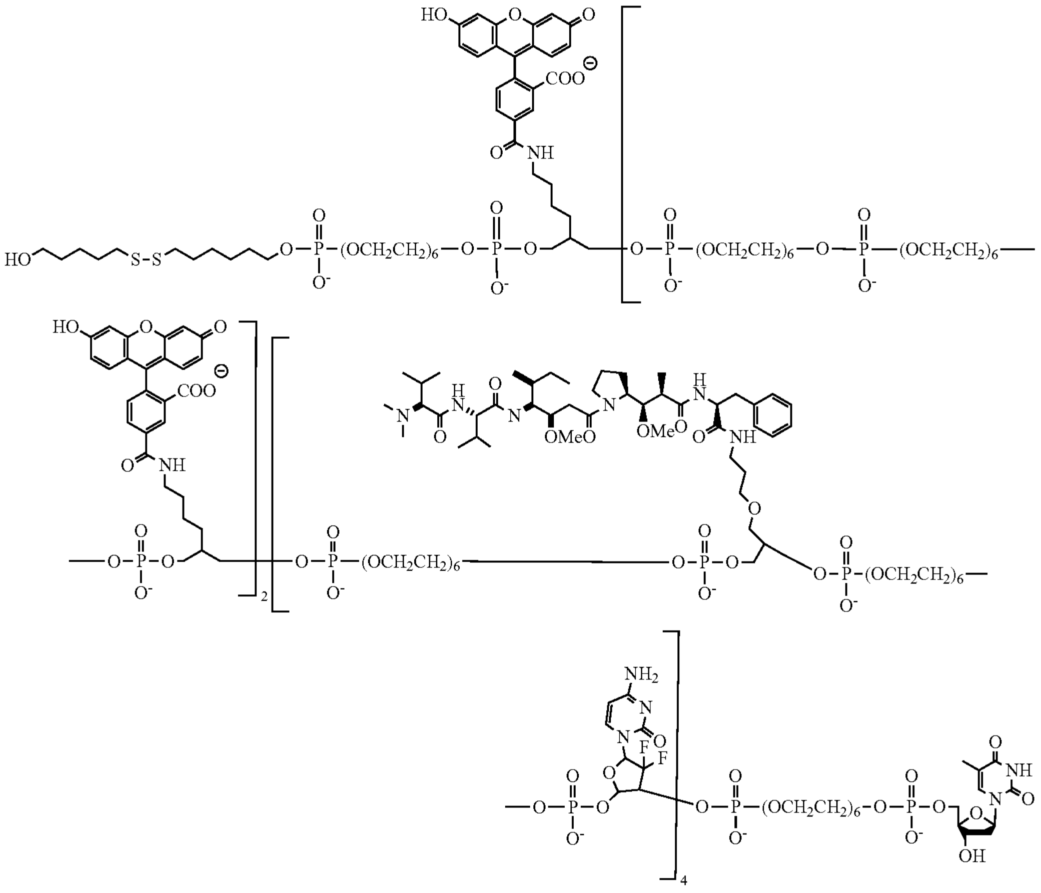 |
| I-16 | 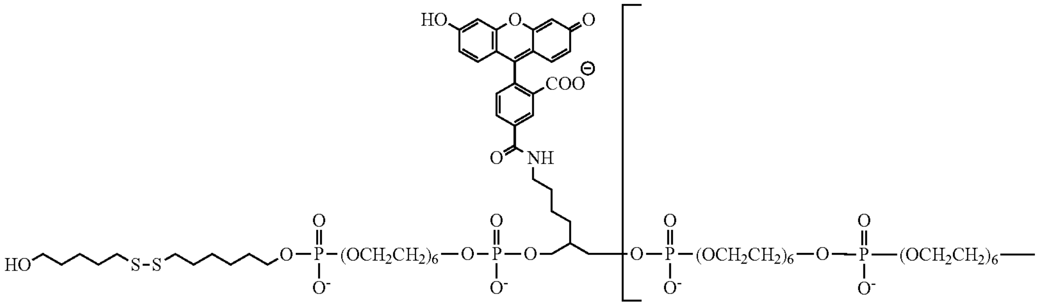 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
|---|---|
| | 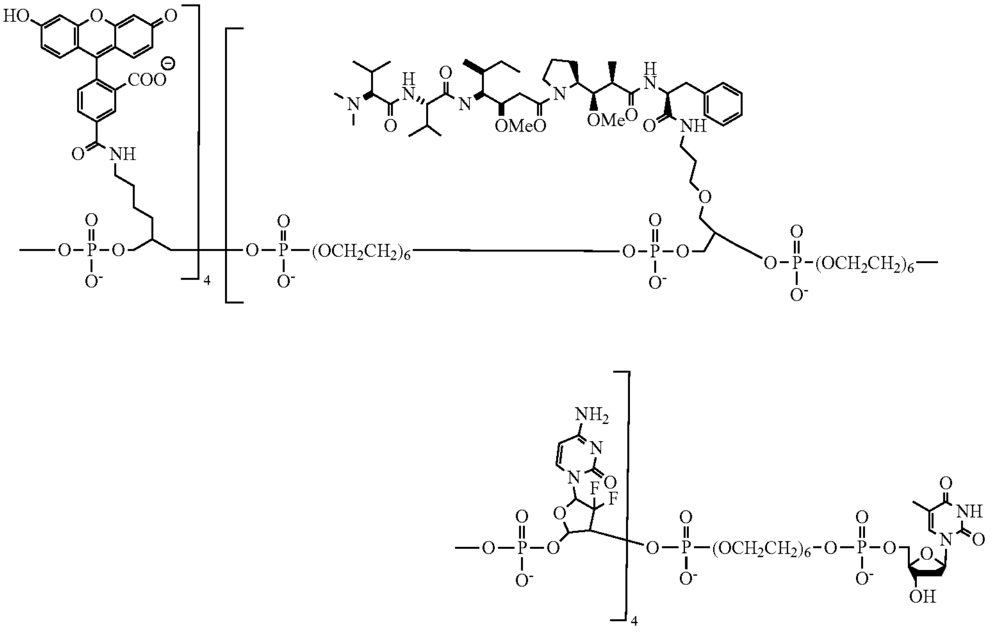 |
| I-17 | 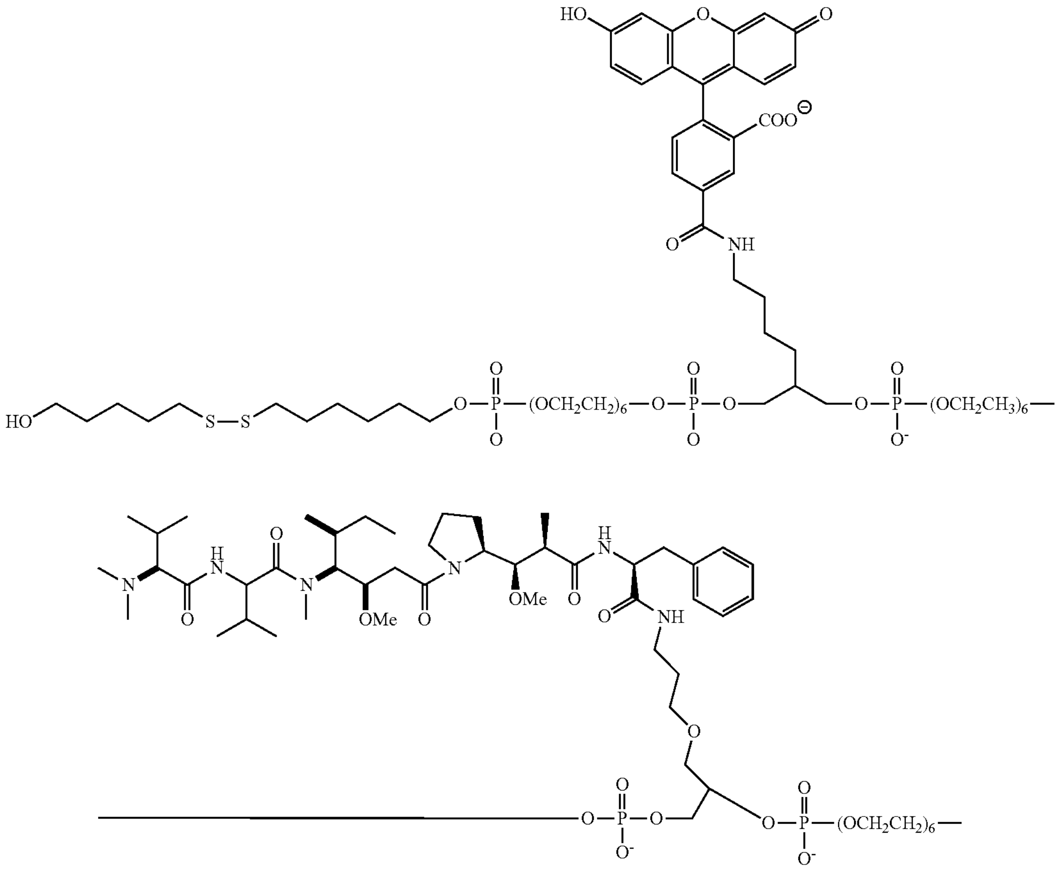 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
|---|---|
| | 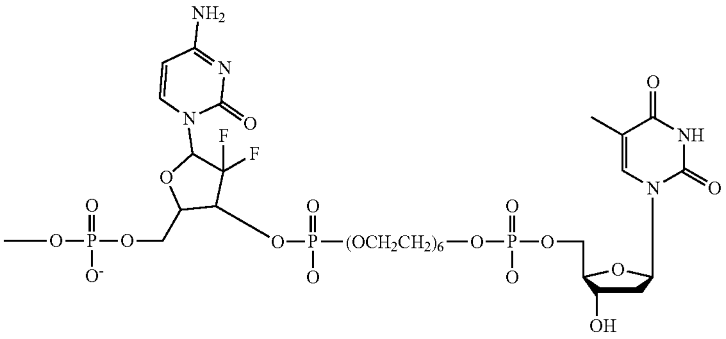 |
| I-18 | 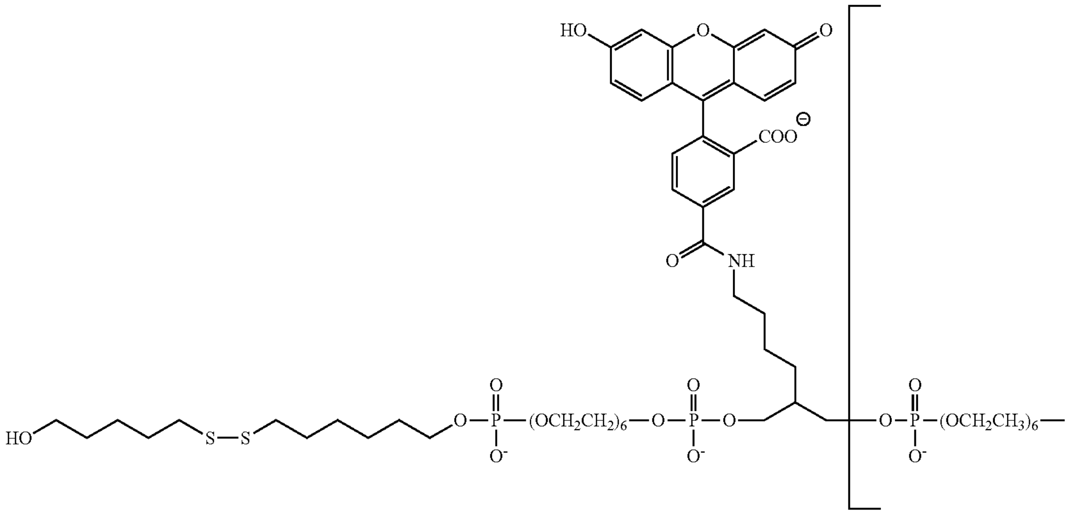 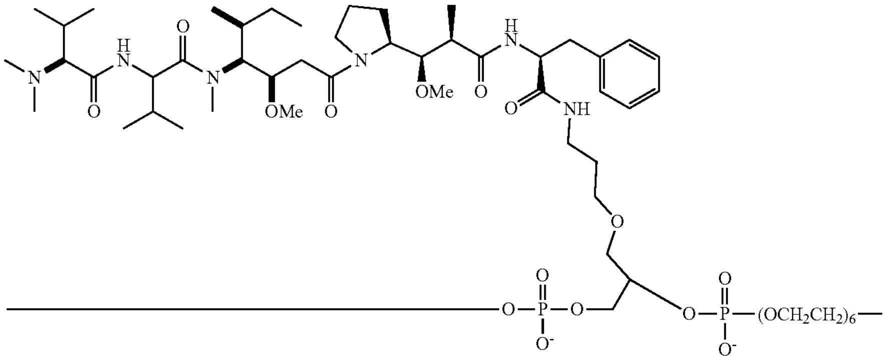 |

TABLE 2-continued
| Exemplary Compounds of Structures (I), (Ia), (Ib), (Ic), (Id), (Ie), (III), (IIIa), (IIIb), (IIIc), or (IIId) | |
|---|---|
| Nos. | Structure |
| | 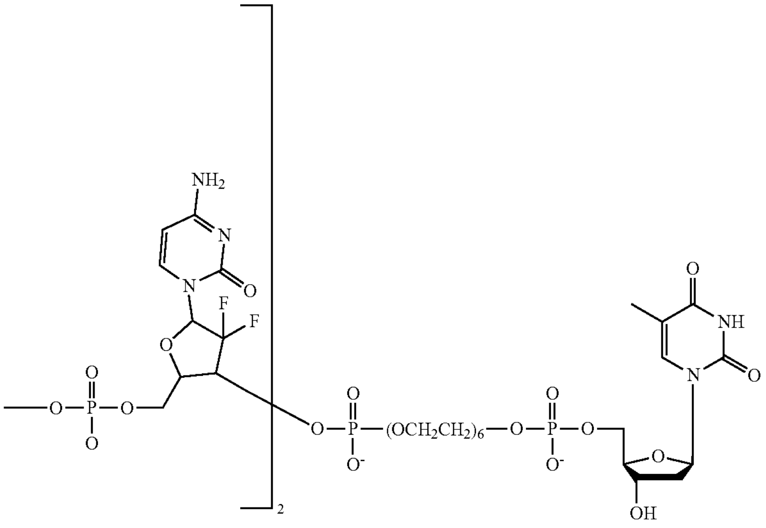 |
| I-19 | 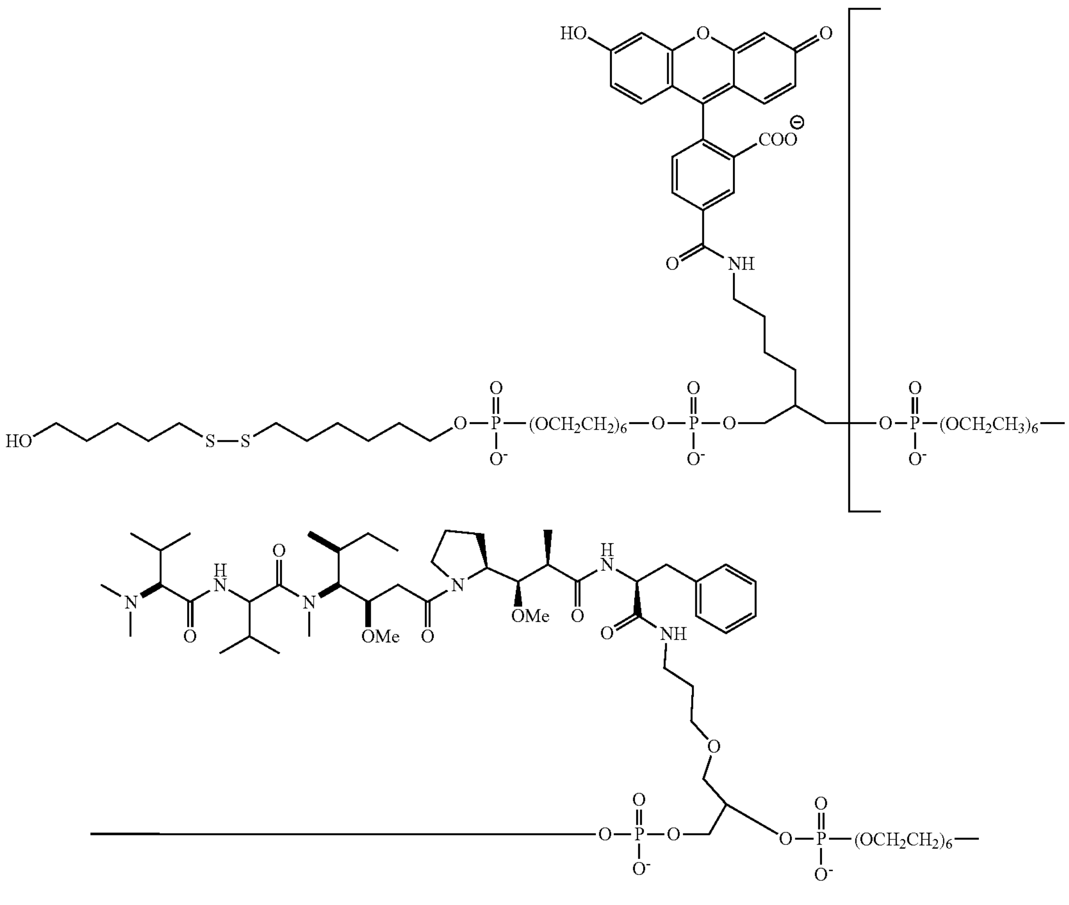 |

TABLE 2-continued
Exemplary Compounds of Structures (I), (Ia), (Ib), (Ic), (Id), (Ie), (III), (IIIa), (IIIb), (IIIc), or (IIId)
| Nos. | Structure |
|---|---|
| | 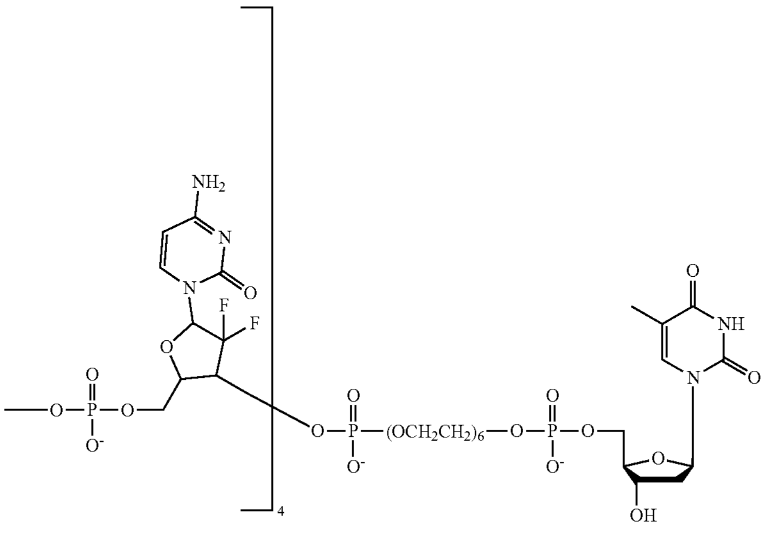 |
| I-20 | 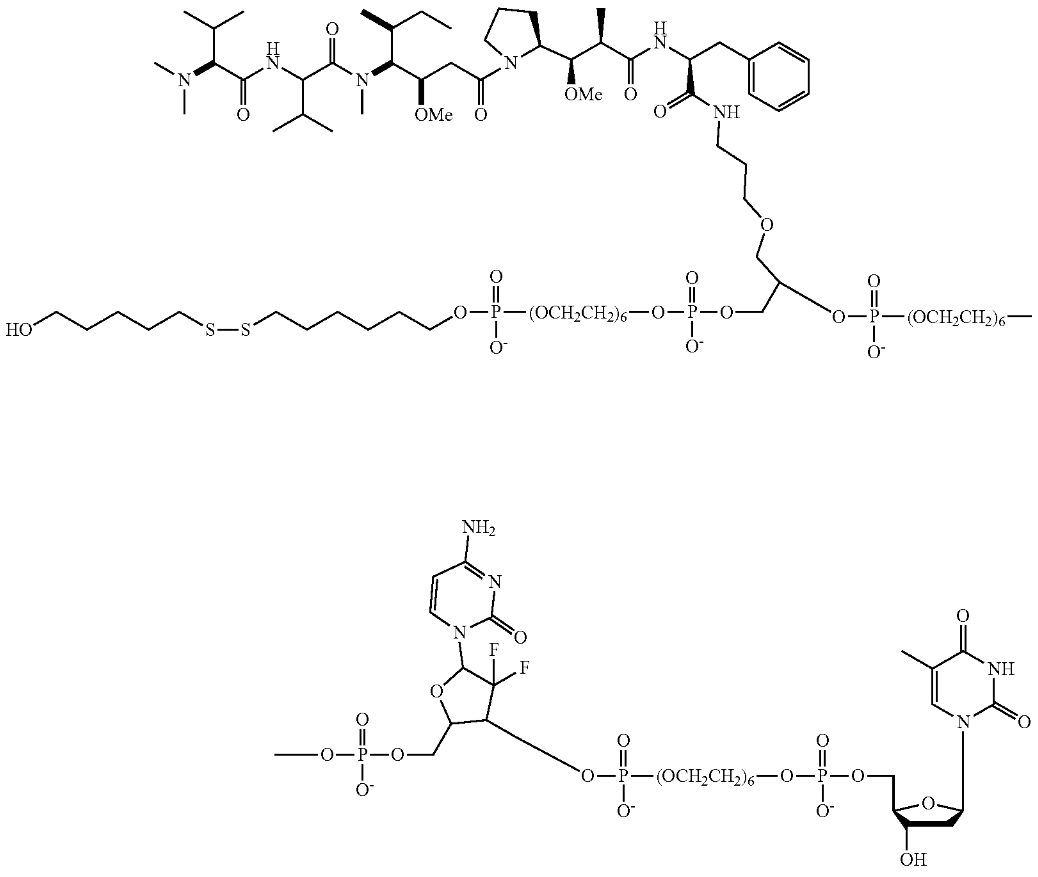 |

TABLE 2-continued
| Exemplary Compounds of Structures (I), (Ia), (Ib), (Ic), (Id), (Ie), (III), (IIIa), (IIIb), (IIIc), or (IIId) | |
|---|---|
| Nos. | Structure |
| I-21 | 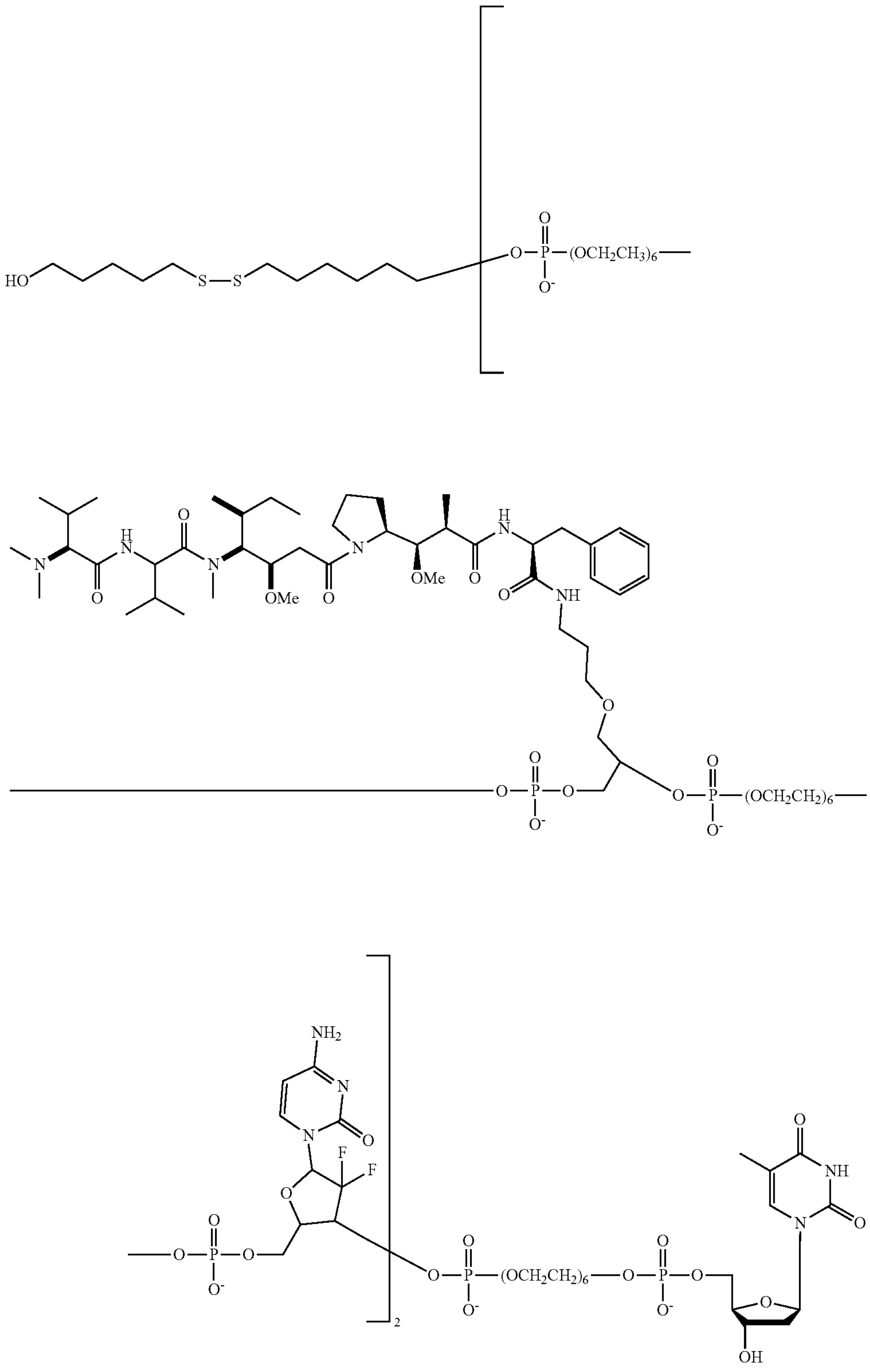 |

TABLE 2-continued

| Exemplary Compounds of Structures (I), (Ia), (Ib), (Ic), (Id), (Ie), (III), (IIIa), (IIIb), (IIIc), or (IIId) | |
|---|---|
| Nos. | Structure |
| I-22 | 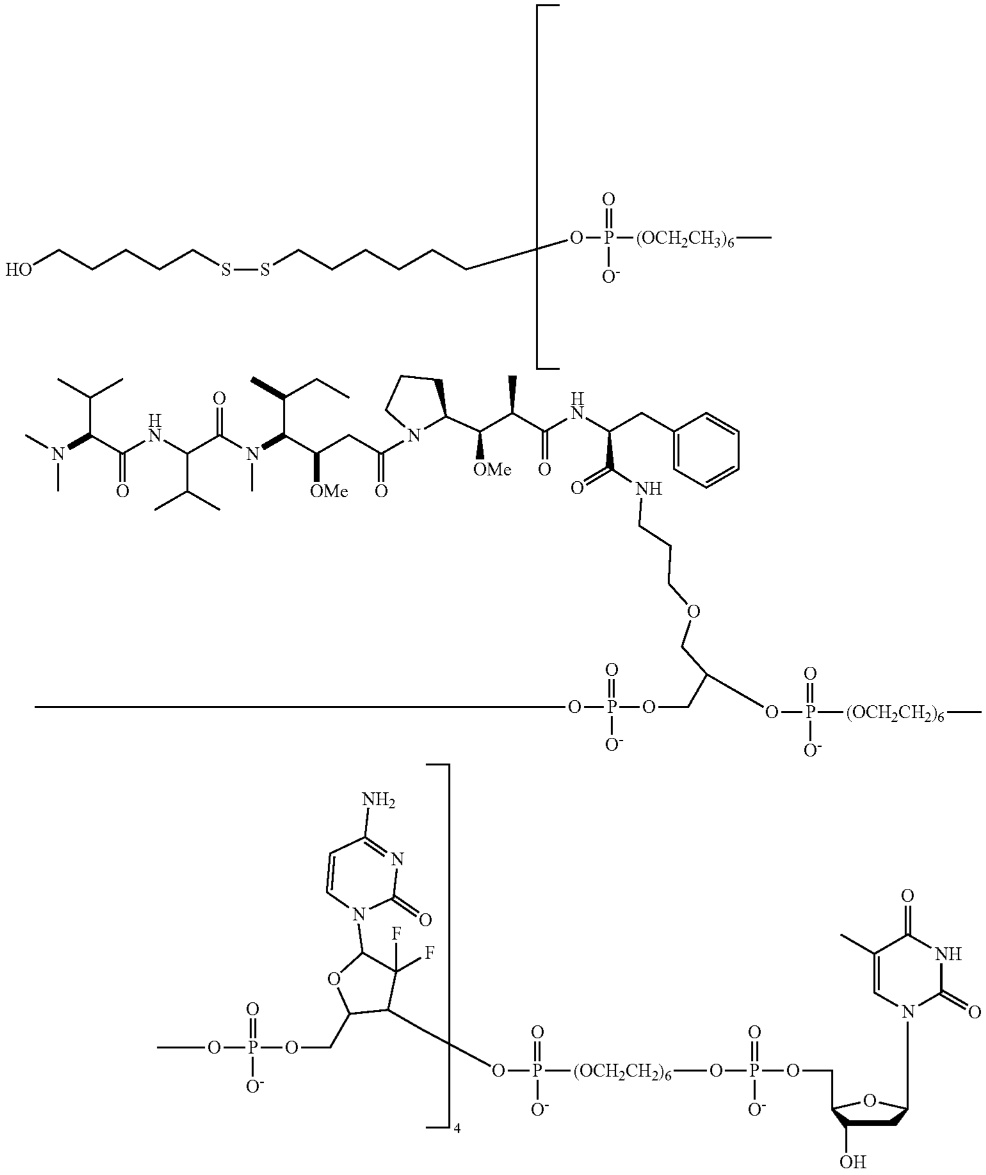 |

Pharmaceutical Compositions

One embodiment provides a composition comprising the compound according any one of the embodiments disclosed herein (e.g., a compound of Structure (I), (Ia), (Ib), (Ic), (Id), (Ie), (III), (IIIa), (IIIb), (IIIc), or (IIId)) and a pharmaceutically acceptable carrier.

Other embodiments are directed to pharmaceutical compositions. The pharmaceutical composition comprises any one (or more) of the compounds of Structure (I), (Ia), (Ib), (Ic), (Id), (Ie), (III), (IIIa), (IIIb), (IIIc), or (IIId) and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound of Structure (I), (Ia), (Ib), (Ic), (Id), (Ie), (III), (IIIa), (IIIb), (IIIc), or (IIId) and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound of Structure (I), (Ia), (Ib), (Ic), (Id), (Ie), (III), (IIIa), (IIIb), (IIIc), or (IIId) is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound of Structure (I), (Ia), (Ib), (Ic), (Id), (Ie), (III), (IIIa), (IIIb), (IIIc), or (IIId) is provided in the form of a rapid release formulation, in the form of an extended release formulation, or in the form of an intermediate release formulation. In yet other embodiments, the compound of Structure (I), (Ia), (Ib), (Ic), (Id), (Ie), (III), (IIIa), (IIIb), (IIIc), or (IIId) is administered topically.

The compounds of Structure (I), (Ia), (Ib), (Ic), (Id), (Ie), (III), (IIIa), (IIIb), (IIIc), or (IIId) are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of Structure (I), (Ia), (Ib), (Ic), (Id), (Ie), (III), (IIIa), (IIIb), (IIIc), or (IIId) is administered in a single dose. Typically, such administration will be by injection, e.g., intravenous injection, in order to introduce the agent quickly. However, other routes are used as appropriate. A single dose of a compound of Structure (I), (Ia), (Ib), (Ic), (Id), (Ie), (III), (IIIa), (IIIb), (IIIc), or (Id) may also be used for treatment of an acute condition.

In some embodiments, a compound of Structure (I), (Ia), (Ib), (Ic), (Id), (Ie), (III), (IIIa), (IIIb), (IIIc), or (IIId) is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of Structure (I), (Ia), (Ib), (Ic), (Id), (Ie), (III), (IIIa), (IIIb), (IIIc), or (Id) and another agent are administered together about once per day to about 6 times per day. In another embodiment the administration of a compound of Structure (I), (Ia), (Ib), (Ic), (Id), (Ie), (III), (IIIa), (IIIb), (IIIc), or (IIId) and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of Structure (I), (Ia), (Ib), (Ic), (Id), (Ie), (III), (IIIa), (IIIb), (IIIc), or (IIId) may continue as long as necessary. In some embodiments, a compound of Structure (I), (Ia), (Ib), (Ic), (Id), (Ie), (III), (IIIa), (IIIb), (IIIc), or (IIId) is administered for more than 1, 2, 3, 4, 5, 6, 7, 14, or 28 days. In some embodiments, a compound of Structure (I), (Ia), (Ib), (Ic), (Id), (Ie), (III), (IIIa), (IIIb), (IIIc), or (IIId) is administered for less than 28, 14, 7, 6, 5, 4, 3, 2, or 1 day. In some embodiments, a compound of Structure (I), (Ia), (Ib), (Ic), (Id), (Ie), (III), (IIIa), (IIIb), (IIIc), or (IIId) is administered chronically on an ongoing basis, e.g., for the treatment of chronic effects.

In some embodiments, the compounds of Structure (I), (Ia), (Ib), (Ic), (Id), (Ie), (III), (IIIa), (IIIb), (IIIc), or (IIId) are administered in dosages. It is known in the art that due to inter-subject variability in compound pharmacokinetics, individualization of dosing regimen is necessary for optimal therapy. Dosing for a compound of the disclosure may be found by routine experimentation in light of the instant disclosure.

In some embodiments, the compounds of Structure (I), (Ia), (Ib), (Ic), (Id), (Ie), (III), (IIIa), (IIIb), (IIIc), or (IIId) are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of Structure (I), (Ia), (Ib), (Ic), (Id), (Ie), (III), (IIIa), (IIIb), (IIIc), or (IIId) and a pharmaceutically acceptable diluent(s), excipient(s), or carrier(s). In certain embodiments, the compounds described are administered as pharmaceutical compositions in which compounds of Structure (I), (Ia), (Ib), (Ic), (Id), (Ie), (III), (IIIa), (IIIb), (IIIc), or (IIId) are mixed with other active ingredients, as in combination therapy. Encompassed herein are all combinations of actives set forth in the combination therapies section below and throughout this disclosure. In specific embodiments, the pharmaceutical compositions include one or more compounds of Structure (I), (Ia), (Ib), (Ic), (Id), (Ie), (III), (IIIa), (IIIb), (IIIc), or (IIId).

A pharmaceutical composition, as used herein, refers to a mixture of a compound of Structure (I), (Ia), (Ib), (Ic), (Id), (Ie), (III), (IIIa), (IIIb), (IIIc), or (Id) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Structure (I), (Ia), (Ib), (Ic), (Id), (Ie), (III), (IIIa), (IIIb), (IIIc), or (IIId) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds of Structure (I), (Ia), (Ib), (Ic), (Id), (Ie), (III), (IIIa), (IIIb), (IIIc), or (IIId) are used singly or in combination with one or more therapeutic agents as components of mixtures.

In one embodiment, one or more compounds of Structure (I), (Ia), (Ib), (Ic), (Id), (Ie), (III), (IIIa), (IIIb), (IIIc), or (IIId) is formulated in an aqueous solution. In specific embodiments, the aqueous solution is selected from, by way of example only, a physiologically compatible buffer, such as Hank's solution, Ringer's solution, or physiological saline buffer. In other embodiments, one or more compound of Structure (I), (Ia), (Ib), (Ic), (Id), (Ie), (III), (IIIa), (IIIb), (IIIc), or (IIId) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of Structure (I), (Ia), (Ib), (Ic), (Id), (Ie), (III), (IIIa), (IIIb), (IIIc), or (IIId)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Structure (I), (Ia), (Ib), (Ic), (Id), (Ie), (III), (IIIa), (IIIb), (IIIc), or (IIId) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Structure (I), (Ia), (Ib), (Ic), (Id), (Ie), (III), (IIIa), (IIIb), (IIIc), or (IIId) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Structure (I), (Ia), (Ib), (Ic), (Id), (Ie), (III), (IIIa), (IIIb), (IIIc), or (IIId) is accomplished by means of iontophoretic patches and the like. In certain embodiments, transdermal patches provide controlled delivery of the compounds of Structure (I), (Ia), (Ib), (Ic), (Id), (Ie), (III), (IIIa), (IIIb), (IIIc), or (IIId). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Structure (I), (Ia), (Ib), (Ic), (Id), (Ie), (III), (IIIa), (IIIb), (IIIc), or (IIId) are formulated for administration by inhalation. Various forms suitable for administration by inhalation include, but are not limited to, aerosols, mists or powders. Pharmaceutical compositions of any of compound of Structure (I), (Ia), (Ib), (Ic), (Id), (Ie), (III), (IIIa), (IIIb), (IIIc), or (IIId) are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of Structure (I), (Ia), (Ib), (Ic), (Id), (Ie), (III), (IIIa), (IIIb), (IIIc), or (IIId) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with melted cocoa butter.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Structure (I), (Ia), (Ib), (Ic), (Id), (Ie), (III), (IIIa), (IIIb), (IIIc), or (IIId) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Structure (I), (Ia), (Ib), (Ic), (Id), (Ie), (III), (IIIa), (IIIb), (IIIc), or (IIId), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of Structure (I), (Ia), (Ib), (Ic), (Id), (Ie), (III), (IIIa), (IIIb), (IIIc), or (IIId) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Structure (I), (Ia), (Ib), (Ic), (Id), (Ie), (III), (IIIa), (IIIb), (IIIc), or (IIId). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds ranges from 0.0001 to 10 g, 0.0005 to 9 g, 0.001 to 8 g, 0.005 to 7 g, 0.01 to 6 g, 0.05 to 5 g, 0.1 to 4 g, 0.5 to 4 g, or 1 to 3 g.

Method of Treatment

Certain compounds of the present disclosure are useful for treating disease (i.e., compounds of Structure (I), (Ia), (Ib), (Ic), (Id), (Ie), (III), (IIIa), (IIIb), (IIIc), or (IIId)). Those compounds disclosed herein offer a targeted approach to drug delivery strategies. Accordingly, one embodiment provides a method of treating a disease (or the symptoms thereof) comprising administering to a mammal (e.g., a human) in need thereof a therapeutically effective amount of a compound of Structure (I), (Ia), (Ib), (Ic), (Id), (Ie), (III), (IIIa), (IIIb), (IIIc), or (IIId).

For example, in certain embodiments the disclosure provides a method of treating solid tumors, multiple myeloma, gliomas, clear cell renal cell carcinoma, prostate cancer, ovarian cancer, non-small cell lung cancer, GI malignancies, acute lymphoblastic leukemia, acute myelogenous leukemia, renal cell carcinoma, colorectal carcinoma, epithelial cancers, pancreatic and gastric cancers, renal cell carcinoma, non-Hodgkin's lymphoma, metastatic renal cell carcinoma, malignant mesothelioma, pancreatic, ovarian, and/or lung adenocarcinoma, B-cell malignancies, breast cancer, melanoma, recurrent multiple myeloma, small cell lung cancer, CD22-positive B cell malignancies, Hodgkin's lymphoma/anaplastic large cell lymphoma, or HER2-positive breast cancer.

In some of the foregoing embodiments, the disease is cancer. For example, in certain embodiments, the cancer is breast cancer, non-Hodgkin's lymphoma, acute myeloid leukemia, multiple myeloma, gastric cancer, renal cell carcinoma, solid tumors, ovarian cancer, prostate cancer, colorectal cancer, pancreatic cancer, small cell lung cancer, diffuse large B-cell lymphoma, a neoplasm, urothelial cancer, ALL, CLL, glioblastoma, Hodgkin's lymphoma, lymphoma, mesothelioma, non-small cell lung cancer, recurrent head and neck cancer, or a combination thereof.

Certain embodiments also relate to a method of treating a hyperproliferative disorder in a mammal (e.g., a human) that comprises administering to said mammal a therapeutically effective amount of a compound of Structure (I), (Ia), (Ib), (Ic), (Id), (Ie), (III), (IIIa), (IIIb), (IIIc), or (IIId), or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Certain particular embodiments provide methods for treatment of lung cancers, the methods comprise administering an effective amount of any of the above described compounds of Structure (I), (Ia), (Ib), (Ic), (Id), (Je), (III), (IIIa), (IIIb), (IIIc), or (IIId) (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Accordingly, in some embodiments of Structure (I), (Ia), (Ib), (Ic), (Id), (Je), (III), (IIIa), (IIIb), (IIIc), or (IIId) A is an antibody or a cell surface receptor antagonist. For example, epidermal growth factor receptor (EGFR) inhibitor, a hepatocyte growth factor receptor (HGFR) inhibitor, an insulin-like growth factor receptor (IGFR) inhibitor, a folate, a MET inhibitor, or antibodies such as trastuzumab.

In even more embodiments, the method further comprises inducing apoptosis.

In some embodiments, the method of treatment comprises treating a tumor having tumor cells with tumor cell receptors. In some embodiments, the tumor cells have receptors ranging from 1,000 to 100,000, from 1,000 to 50,000, from 1,000 to 25,000 receptors, 1,000 to 10,000 receptors per cell. For example, in some embodiments the tumor cells have about 1,000, about 10,000, or less than 100,000 receptors per cell.

Further therapeutic agents that can be combined with a compound of the disclosure are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds of Structure (I), (Ia), (Ib), (Ic), (Id), (Ie), (III), (IIIa), (IIIb), (IIIc), or (IIId) described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few days apart.

In some embodiments, the method further comprises administering an additional therapeutic agent selected from the group consisting of an antineoplastic agent, an enediyne antitumor antibiotic, a maytansinoid, a topoisomerase inhibitor, a kinase inhibitor, an anthracycline, and EGFR inhibitor, an alkylating agent and combinations thereof.

In some more specific embodiments, the method further comprises administering an additional therapeutic agent selected from the group consisting of an antineoplastic agent, an enediyne antitumor antibiotic, a maytansinoid, a topoisomerase inhibitor, a kinase inhibitor, an anthracycline, and EGFR inhibitor, an alkylating agent and combinations thereof.

In certain embodiments, the additional therapeutic agent comprises auristatin F, monomethyl auristatin F, monomethyl auristatin E, paciltaxol, SN-38, calicheamicin, anthramycin, abbeymycin, chicamycin, DC-81, mazethramycin, neothramycin A, neothramycin B, porothramycin prothracarcin, sibanomicin, sibiromycin, tomamycin, mertansine, emtansine, irinotecan, camptothecin, topotecan, silatecan, cositecan, Exatecan, Lurtotecan, gimatecan, Belotecan, and Rubitecan.

The examples and preparations provided below further illustrate and exemplify the compounds of the present disclosure and methods of preparing such compounds. It is to be understood that the scope of the present disclosure is not limited in any way by the scope of the following examples and preparations. In the following examples, and throughout the specification and claims, molecules and moieties with a single stereocenter, unless otherwise noted, exist as a racemic mixture. Those molecules and moieties with two or more stereocenters, unless otherwise noted, exist as a racemic mixture of diastereomers. Single enantiomers/diastereomers may be obtained by methods known to those skilled in the art.

For ease of illustration, various compounds comprising phosphorous moieties (e.g., phosphate and the like) are depicted in the anionic state (e.g., $—OPO(OH)O^-$, $—OPO_3^{2-}$). One of skill in the art will readily understand that the charge is dependent on pH and the uncharged (e.g., protonated or salt, such as sodium or other cation) forms are also included in the scope of embodiments of the disclosure.

Compositions comprising any of the foregoing compounds and one or more analyte molecules (e.g., biomolecules) are provided in various other embodiments. In some embodiments, use of such compositions in analytical methods for detection of the one or more analyte molecules is also provided.

In some embodiments of the foregoing methods, $R^2$ is a linker comprising a covalent linkage to an analyte molecule, such as a biomolecule. For example, a nucleic acid or polymer thereof, or an amino acid or a polymer thereof (e.g., polynucleotide or polypeptide). In still more embodiments, the biomolecule is an enzyme, receptor, receptor ligand, antibody, glycoprotein, aptamer, or prion.

In yet other embodiments of the foregoing method, $R^2$ is a linker comprising a covalent linkage to a solid support such as a microparticle (e.g., controlled pore glass or polystyrene beads). For example, in some embodiments the microparticle is a polymeric bead or non-polymeric bead.

In addition to the above methods, embodiments of the compounds of structure (I), (Ia), (Ib), (Ic), (Id), (Ie), (III), (IIIa), (IIIb), (IIIc), and (IIId) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by conjugating a compound of structure (I), (Ia), (Ib), (Ic), (Id), (Ie), (III), (IIIa), (IIIb), (IIIc), and (IIId) to an antibody or sugar or other moiety that preferentially binds cancer cells; imaging in surgical procedures; binding of histones for identification of various diseases; drug delivery in dental work and other procedures.

It is understood that any embodiment of the compounds of structure (I), (Ia), (Ib), (Ic), (Id), (Ie), (III), (IIIa), (IIIb), (IIIc), and (IIId), as set forth above, and any specific choice set forth herein for a $R^1$, $R^2$, $R^3$, $R^4$, $R^5$, $R^6$, $R^7$, $L^1$, $L^2$, $L^3$, $L^4$, $L^5$, $L^6$, $L^7$, $L^8$, $L^9$, $L^{10}$, $L^{11}$, $M^1$, $M^2$, $M^3$, l, m, n, p, and/or q variable in the compounds of structures (I), (Ia), (Ib), (Ic), (Id), (Ie), (III), (IIIa), (IIIb), (IIIc), or (IIId), as set forth above, may be independently combined with other embodiments and/or variables of the compounds of structures (I), (Ia), (Ib), (Ic), (Id), (Ie), (III), (IIIa), (IIIb), (IIIc), and (IIId) to form embodiments of the disclosure not specifically set forth above. In addition, in the event that a list of choices is listed for any particular $R^1$, $R^2$, $R^3$, $R^4$, $R^5$, $R^6$, $R^7$, $L^1$, $L^2$, $L^3$, $L^4$, $L^5$, $L^6$, $L^7$, $L^8$, $L^9$, $L^{10}$, $L^{11}$, $M^1$, $M^2$, $M^3$, l, m, n, p, and/or q variable in a particular embodiment and/or claim, it is understood that each individual choice may be deleted from the particular embodiment and/or claim and that the remaining list of choices will be considered to be within the scope of the disclosure.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would methods known to one skilled in the art. It is also understood that one skilled in the art would be able to make, in a similar manner as described below, other compounds of structure (I), (Ia), (Ib), (Ic), (Id), (Ie), (III), (IIIa), (IIIb), (IIIc), and (IIId) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this disclosure.

DNA synthesis methodology can be applied to build compounds of Structure (I) and (III). Monomers (e.g., phosphoramidite monomers) can be purchased commercially (e.g., from ChemGenes Corporation, Wilmington Mass.) or synthesized using methods described herein (see, e.g., Examples 1-3). Introduction of desired moieties can be accomplished during the DNA synthesis steps by including the desired moiety as a portion of the monomer (see, e.g., $G^1$ of General Reaction Scheme I). An exemplary DNA synthesis scheme is shown below.

A REPRESENTATIVE DNA SYNTHESIS CYCLE

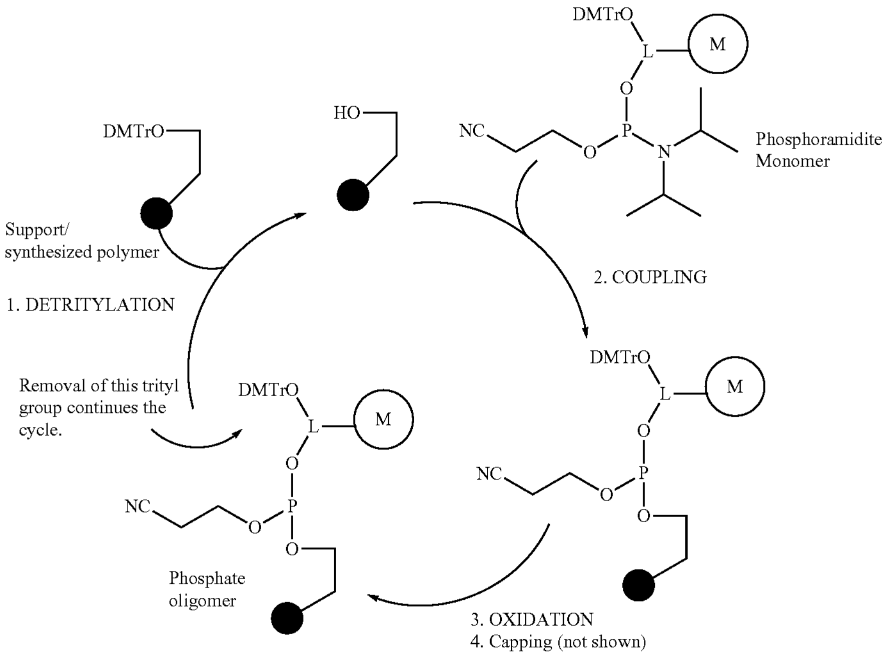

appreciate, the protecting group may also be a polymer resin such as a Wang resin, Rink resin or a 2-chlorotrityl-chloride resin.

Furthermore, all compounds of the disclosure which exist in free base or acid form can be converted to their salts by treatment with the appropriate inorganic or organic base or acid by methods known to one skilled in the art. Salts of the compounds of the disclosure can be converted to their free base or acid form by standard techniques.

The following Reaction Schemes illustrate exemplary methods of making compounds of this disclosure. It is understood that one skilled in the art may be able to make these compounds by similar methods or by combining other Oligomerization is initiated, typically, through the removal of a protecting group (e.g. a dimethoxytrityl group, DMTr) to reveal a free —OH (hydroxyl) group (Step 1, DETRITYLATION). In a subsequent coupling step, a phosphoramidite monomer is introduced that reacts with the free OH group making a new covalent bond to phosphorus, with concomitant loss of the diisopropyl amine group (Step 2, COUPLING). The resultant, phosphite triester is oxidized (e.g. with 12 and pyridine) to the more stable phosphate ester (Step 3, OXIDATION) and a capping step renders unreactive any remaining free OH groups (Step 4, CAPPING). The new product, phosphate oligomer, contains a DMTr protected OH group that can be deprotected to reinitiate the synthetic cycle so another phosphoramidite monomer can be appended to the oligomer.

Customization occurs at step 2 through the choice of phosphoramidite monomer. The nature of L (i.e., a linker group) and M (i.e., a chemotherapeutic agent) in the scheme above are selected such that a desired compound of Structure (I), (Ia), (Ib), (Ic), (Id), (Ie), (III), (IIIa), (IIIb), (IIIc), and (IIId) is synthesized. M can be optionally absent to incorporate desired spacing between M moieties. A person of ordinary skill in the art can select multiple monomer types to arrive at compounds of the disclosure containing multiple therapeutic agents and/or other moieties (e.g., fluorophores or chromophores) with concurrent variability in linker groups.

GENERAL REACTION SCHEME 1 (PHOSPHORAMIDITE)

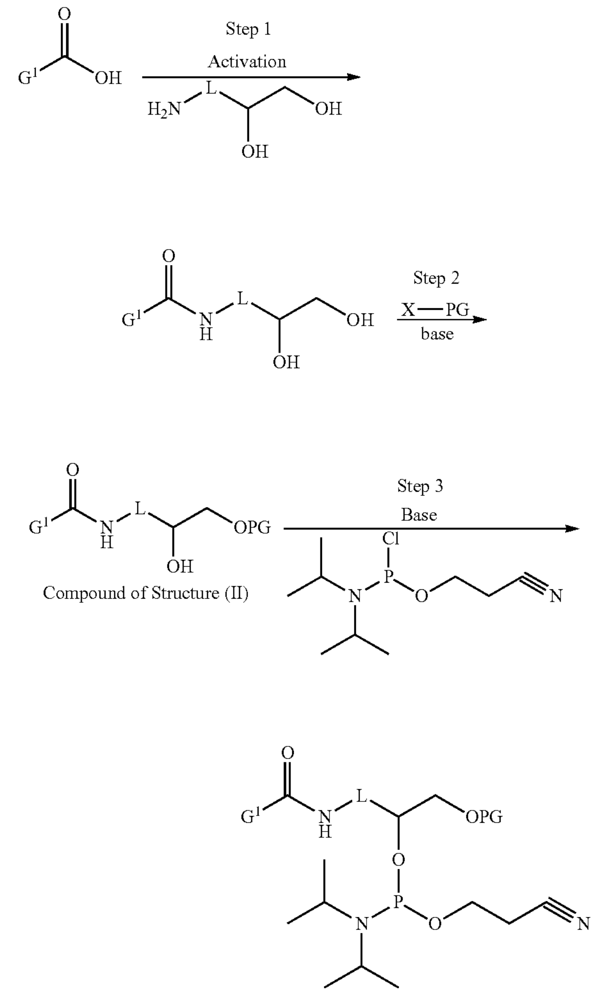

Compound of Structure (II)

Reaction Scheme I illustrates a method for preparation of phosphoramidite intermediates useful for preparation of compounds of Structure (I), (Ia), (Ib), (Ic), (Id), (Ie), (III), (IIIa), (IIIb), (IIIc), or (IIId). Referring to Reaction Scheme I, $G^1$ represents a desired moiety containing a carboxylic acid functional group (e.g., a drug moiety such as Auristatin F, gemcitabine, capecitabine, or SN 38), L represents a bivalent linker moiety (e.g., an alkylene, or alkylene ether), X represents a leaving group (e.g., halo such as Cl), and PG represents a protecting group (e.g., 4,4'-dimethoxytriphenylmethyl). Step 1 of Reaction Scheme I starts with an activation of the carboxylic acid functional group of the first compound shown using known reagents under basic conditions (e.g., HATU and DIPEA in DMF). The activated acid is then reacted with an amine to provide the reaction product of Step 1. The resulting diol is then protected under standard conditions (e.g., 4,4'-dimethoxytriphenylmethyl chloride and pyridine). A diol such as gemcitabine starts from step 2. The protected product is then reacted with 3-((chloro(diisopropylamino)phosphaneyl)oxy)propanenitrile (or other appropriate reagent) to yield a desired compound of Structure (II) as shown above.

The resultant compound of Structure (II) can then be used to synthesize a desired compound of Structure (I), (Ia), (Ib), (Ic), (Id), (Ie), (III), (IIIa), (IIIb), (IIIc), and (IIId) by reaction under well-known (automated) DNA synthesis conditions. In addition to compounds of Structure (II), additional repeat units may be incorporated to achieve a final compound of Structure (I), (Ia), (Ib), (Ic), (Id), (Ie), (III), (IIIa), (IIIb), (IIIc), and (IIId). Generally, compounds having the following structure may be used:

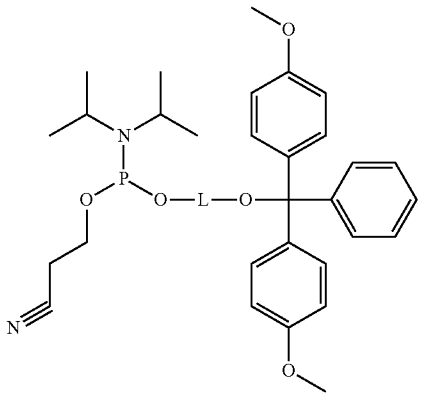

wherein:

L is a desired linker moiety (e.g., including PEG or dye-containing moiety).

In some specific embodiments, the following compound may be used in the synthesis of a compound of Structure (I), (Ia), (Ib), (Ic), (Id), (Ie), (III), (IIIa), (IIIb), (IIIc), and (IIId):

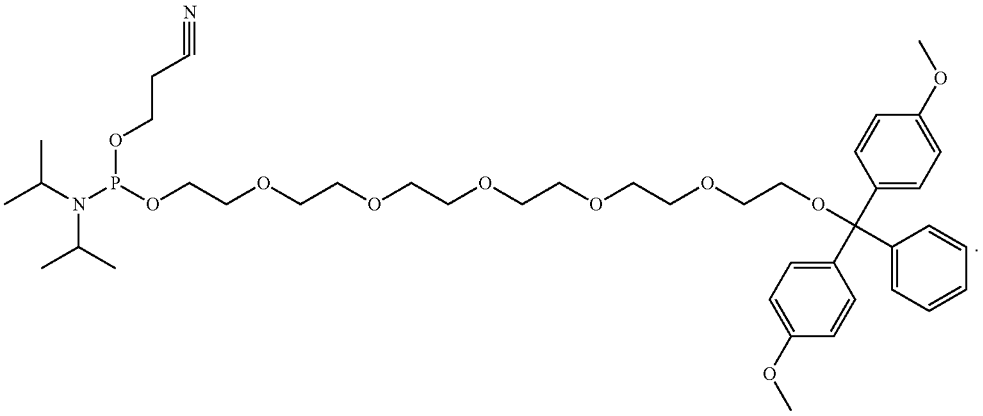 [SMILES: COc1ccc(C(OCCOCCOCCOCCOCCOCCOP(OCCC#N)N(C(C)C)C(C)C)(c2ccccc2)c2ccc(OC)cc2)cc1]

EXAMPLES

General Methods

Mass spectral analysis is performed on a Waters/Micromass Quattro micro MS/MS system (in MS only mode) using MassLynx 4.1 acquisition software. Mobile phase used for LC/MS on dyes is 100 mM 1,1,1,3,3,3-hexafluoro-2-propanol (HFIP), 8.6 mM triethylamine (TEA), pH 8. Phosphoramidites and precursor molecules are also analyzed using a Waters Acquity UHPLC system with a 2.1 mm×50 mm Acquity BEH-$C_{18}$ column held at 45° C., employing an acetonitrile/water mobile phase gradient. Molecular weights for monomer intermediates are obtained using tropylium cation infusion enhanced ionization on a Waters/Micromass Quattro micro MS/MS system (in MS only mode). Excitation and emission profiles experiments are recorded on a Cary Eclipse spectra photometer.

All reactions are carried out in oven dried glassware under a nitrogen atmosphere unless otherwise stated. Commercially available DNA synthesis reagents are purchased from Glen Research (Sterling, VA). Anhydrous pyridine, toluene, dichloromethane, diisopropylethyl amine, triethylamine, acetic acid, pyridine, and THE are purchased from Aldrich. All other chemicals are purchase from Aldrich or TCI and are used as is with no additional purification.

Example 1

SYSNTHESIS OF DMT PROTECTED GEMCITABINE COMPOUND

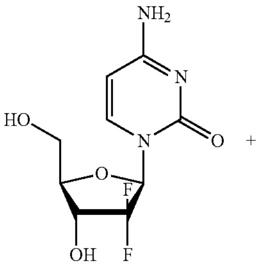

-continued

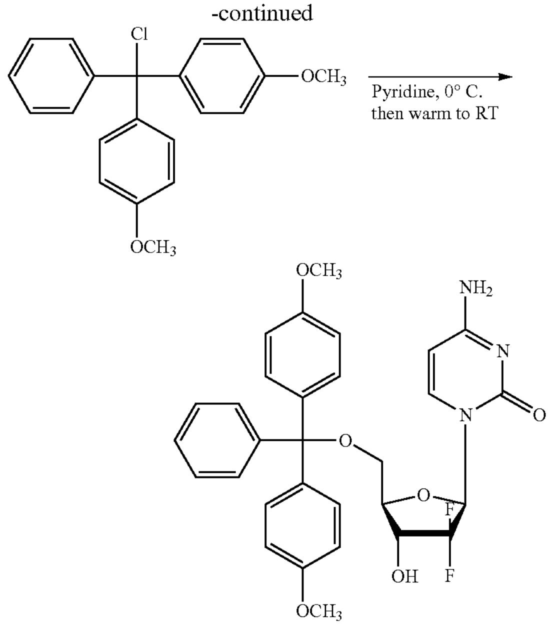

Gencitabine (0.5057 mmole theoretical) is added to a dried round bottom flask, under inert gas blanket, with magnetic stir bar, followed by addition of pyridine, anhydrous (5.06 mL). The reaction flask is then transferred to an ice water bath (0° C.) and allowed to cool with mixing until thermally equalized (approximately 10 minutes). Then, 4,4'-Dimethoxytrityl chloride (0.257 g, 0.759 mmole) is added to the cooled mixture with continuous mixing under inert gas. The reaction mixture is allowed to warm to room temperature then sampled for TLC analysis. When reaction completion verified, the remaining unreacted 4,4'-Dimethoxytrityl chloride is quenched by addition of methanol to the reaction mixture (0.160 g, 5.06 mmole). The solvent is stripped off by rotary evaporation, under vacuum (10 mbar), with heating (55° C.). The concentrated residue is then suspended in toluene (5.06 mL) and toluene stripped off by rotary evaporation, under vacuum (10 mbar), with heating (55° C.); repeated two time. The crude produce is dissolved in dichloromethane (5.06 mL) and washed with sodium bicarbonate (5.06 mL, saturate aq.) and separated. This process is repeated one time. The separated organic phase is washed with sodium chloride (5.06 mL, saturated aq.) and separated.

The separated organic phase is dried over sodium sulfate, anhydrous and the sodium sulfate filtered off. The product containing organic phase is sampled for TLC and LC-UV/MS analysis. Solvent is removed by rotary evaporation, resulting in crude DMT protected gemcitabine.

This crude material is then combined with crude material from a small-scale test reaction. The combined crude material is purified by silica gel flash chromatography, dichloromethane/methanol mobile phase, product containing fractions are pooled and solvent is removed by rotary evaporation, and then placed on vacuum line for at least 24 hours to yield DMT protected gemcitabine.

Example 2

SYSTHESIS OF DMT PROTECTED GEMCITABINE PHOSPHORAMIDITE

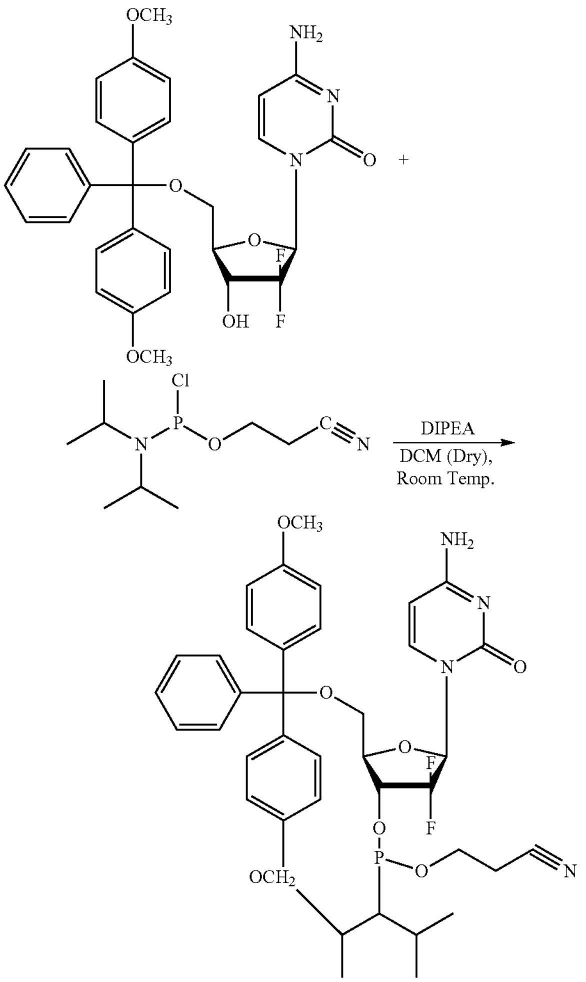

The purified DMT protected gemcitabine (0.226 mmole), dried under vacuum for at least 24 hours is dissolved in dichloromethane (2.26 mL), under inert gas blanket, with magnetic stir bar, followed by addition of DIPEA (0.117 g), and then addition of Cl-Phos. (0.107 g). The reaction is allowed to mix for approximately 15 minutes and then sampled for TLC analysis (TLC showed reaction completion). When reaction completion is verified, the reaction mixture is washed by adding directly to sodium bicarbonate (2.26 mL, saturated aq.) and organic phase separated, repeated one time. The organic phases are combined and dried over sodium sulfate, anhydrous, and then the sodium sulfate filtered off. The product containing organic phase is sampled for TLC and LC-UV/MS analysis. Then, dichloromethane is stripped off by rotary evaporation and proceeded to purification without crude weight. This crude material is then combined with crude material from a small-scale test reaction. The combined crude material is purified by silica gel solid phase extraction, dichloromethane/methanol/triethylamine mobile phase, product containing fractions are pooled. The mobile phase is stripped off by rotary evaporation, and then placed on vacuum line for at least 24 hours to yield DMT protected gemcitabine phosphoramidite. Alternatively, the DMT protected gemcitabine phosphoramidite can be purchased from Glen Research and used as is with no additional purification.

Example 3

Synthesis of Compound I-1

Stock Solution Preparation

Borate buffer prepared at 250 mM, pH 10

Fluorscein-NHS solution prepared at 350 mM (300 mg in 1.35 mL DMSO:acetonitrile at 25:75)

Solid Phase Synthesis

Compound I-1 is prepared on the DNA synthesizer via solid support using standard DNA synthesis techniques (i.e., DMT protected 2-cyanoethyl phosphoramidite). The polymer is removed from the solid support with ammonium hydroxide and lyophilized to a paste. 250 mg aliquots are reconstituted in water. A small aliquot is removed and serial dilutions are prepared in 100 mM $NaCO_3$ at pH 9 to determine concentration (A 263 ε=10,000). Final stock concentration is found to be 14.5 mM.

Dye Coupling Reaction

In 50 mL centrifuge tube equipped with magnetic stir bar is placed water (1.110 μL), borate buffer (1.800 μL), Compound I-1 polymer solution (466 μL), acetonitrile (137.5 μL), triethylamine (313 μL) and fluorescein-NHS solution (675 μL). The tube is wrapped in aluminum foil and the mixture stirred overnight at room temperature.

Size Exclusion Filtration

To an Amicon Ultra-15 Centrifugal filter (Millipore UFC900324, MW cutoff=3000) is added 1 mL of water. The crude reaction from the dye coupling reaction (4.5 mL) is added to the filtration setup. The reaction vessel is rinsed 2× with 4 mL of 100 mM NaOH and the rinseates are transferred to the filtration setup. The filtration setup is centrifuged at max speed (3220 g, swing bucket, 30 minutes). The filtrate is removed and the retentate treated with an additional 10 mL of 100 mM NaOH. The filtration setup is centrifuged as before. Again, the filtrate is removed and a third 10 mL 100 mM NaOH aliquot is added to the retentate. The setup is centrifuged as before and the filtrate removed. A fourth 10 mL 100 mM NaOH aliquot is added to the retentate and centrifuged as before. The filtrate is removed and 10 mL of water are added to the filtration setup. The mixture is centrifuged as before. The retentate is removed, the filtration vessel is washed with water and the rinseates are added to the final volume (3.5 mL). The desired product is confirmed by LC-MS and absorbance is used to determine concentration.

Analytical LC-$UV_{495\ nm}$ chromatogram showed 62% target product I-2 by total peak area or related peak area identified by MS (expected molecular weight 10755.1 and observed molecular weight 70760.7 was found).

Analytical LC-$UV_{495\ nm}$ chromatogram showed 65% target product I-6 by total peak area or related peak area identified by MS (expected molecular weight 5730.7 and observed molecular weight 5734.1 was found).

Analytical LC-$UV_{266\ nm}$ chromatogram showed 22% target product I-10 by total peak area or related peak area identified by MS (expected molecular weight 8722.8 and observed molecular weight 8730.1 was found).

Analytical LC-$UV_{266\ nm}$ chromatogram showed 59% target product I-4 by total peak area or related peak area identified by MS (expected molecular weight 4818.9 and observed molecular weight 4822.1 was found).

Example 4

ACTIVATION AND ANTIBODY CONJUGATION OF COMPOUND I-1

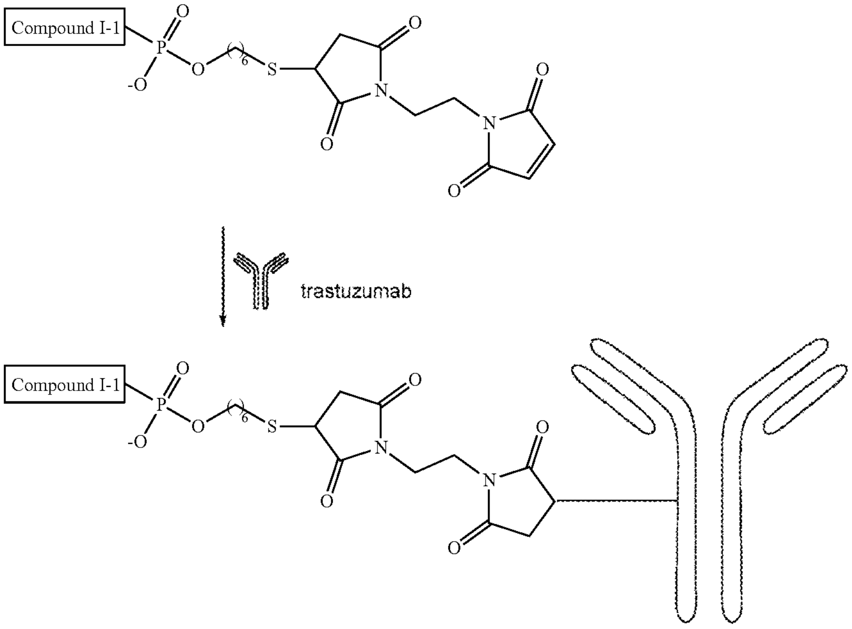

The maleimide functionalized Compound I-1 is prepared according to the method described in Example 1. In parallel, a trastuzumab antibody is treated with bis-maleimidoethane ("BMOE") to reduce disulfide bonds. The reduced antibody is reacted with Compound I-1 in a 5:1 molar ratio of polymer to antibody. The reaction results in a final product having a polymer to antibody ratio of 1:1 as detected by size exclusion chromatography. In some embodiments, anti-CD33, anti-CD70, or anti-CD123 may be used with bis-maleimidoethane ("BMOE") to reduce disulfide bonds. I-2, I-6, and I-9 ADCs were prepared according to EXAMPLE 4 procedure and shown below:

Compound I-9 ADC
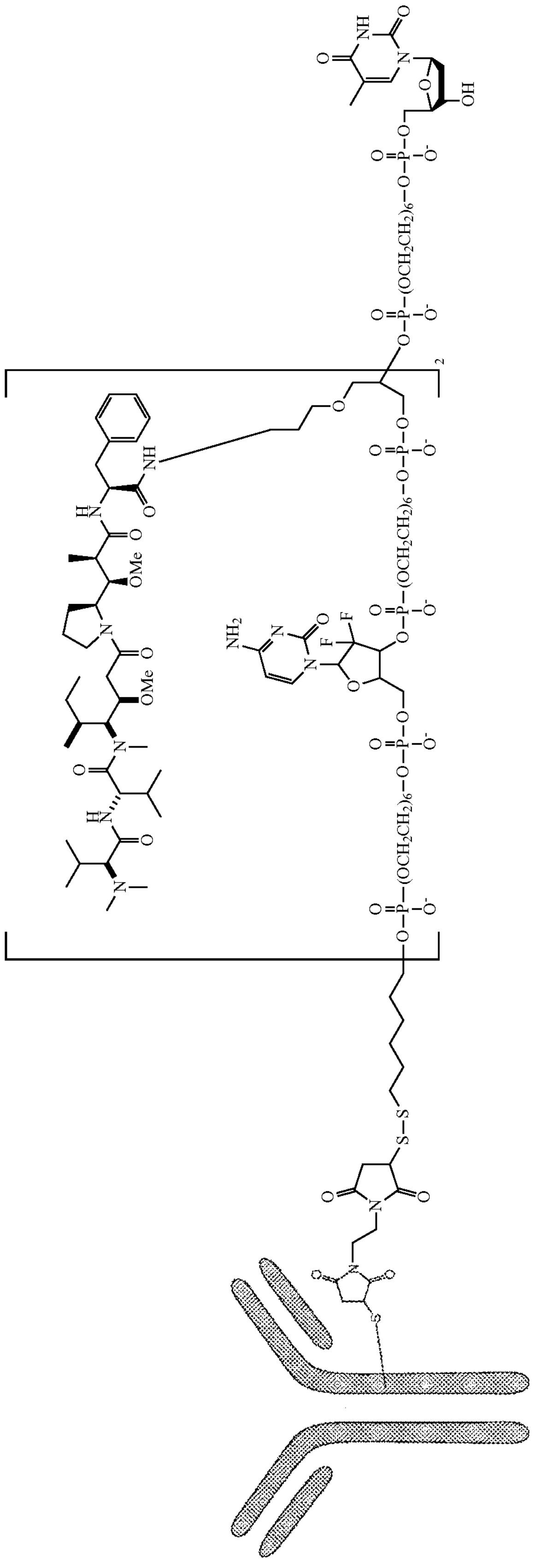

-continued
Compound I-6 ADC
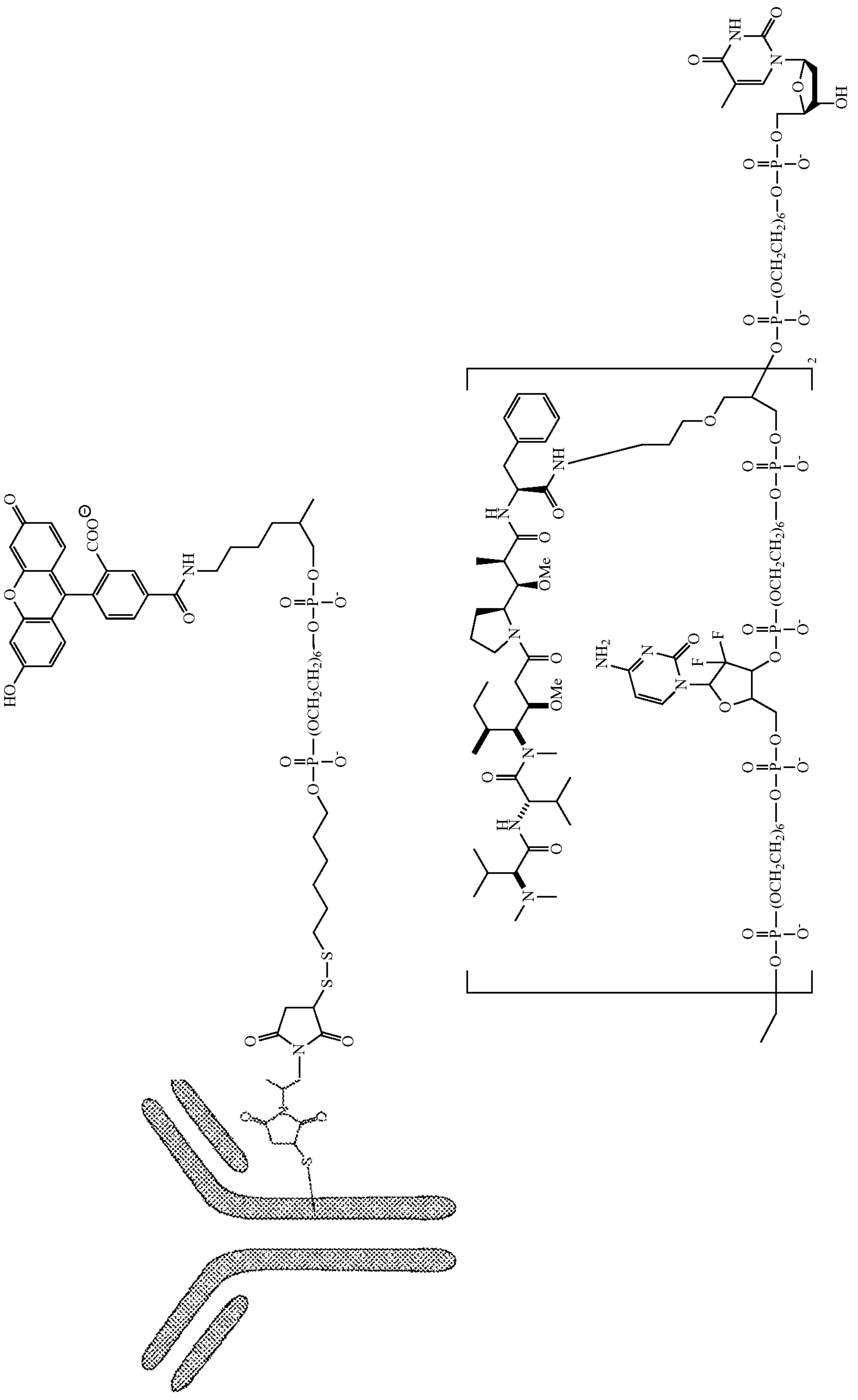

-continued
Compound I-2 ADC
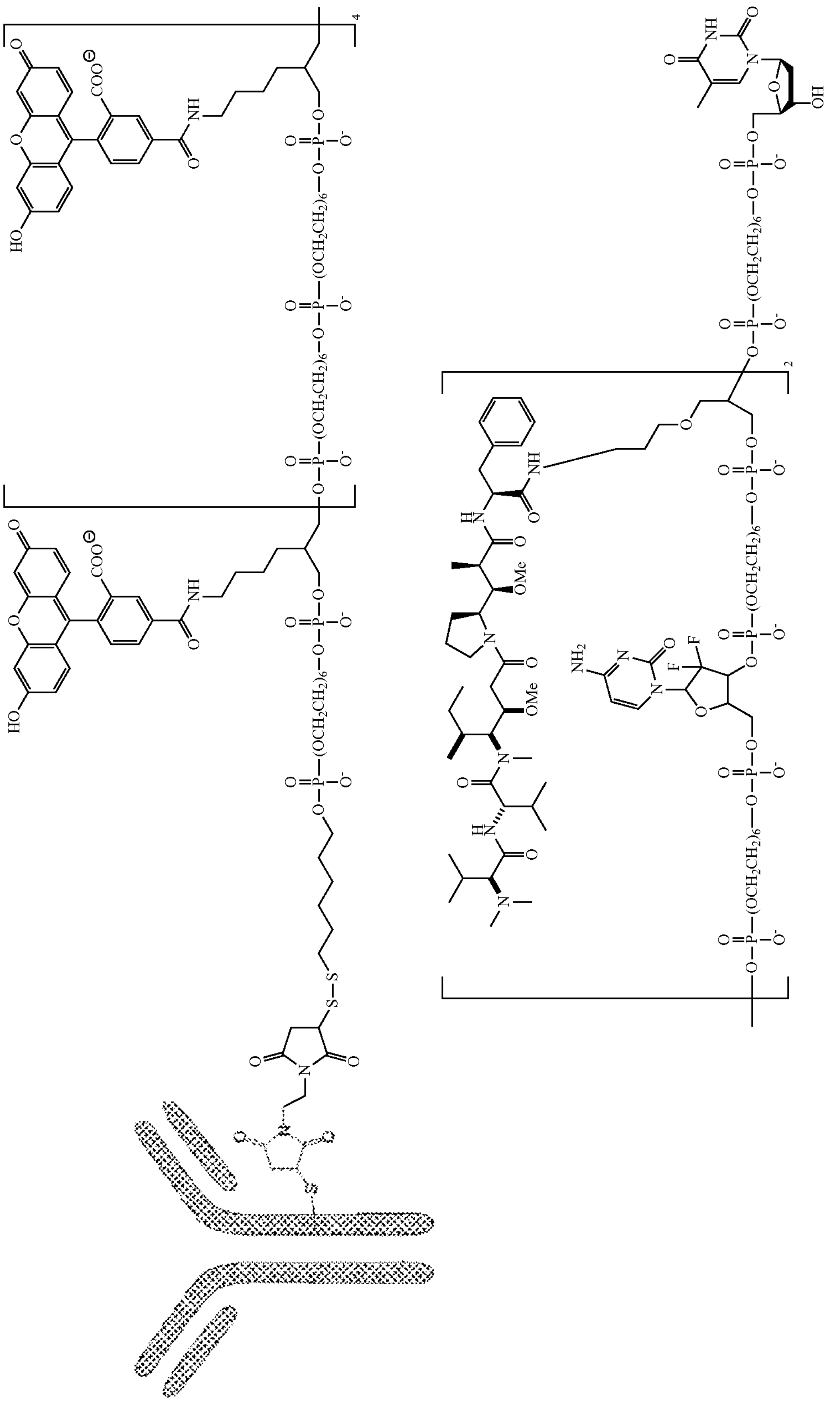

Other compounds disclosed herein (I-1, I-3-I-5, I-7-I-8, and I-10-I-22) can be conjugated with antibody by the same method described above to generate other ADCs. Although antibody trastuzumab is used in EXAMPLE 4 demonstrating conjugation between compounds disclosed herein and an antibody, it is used for merely an illustration and can include other antibodies such as brentuximab, gemtuzumab, trastuzumab, inotuzumab, polatuzumab, enfortumab, trastuzumab, sacituzumab, belantamab, or moxetumomab.

Example 5

Cell Proliferation Assay

Figure 2:
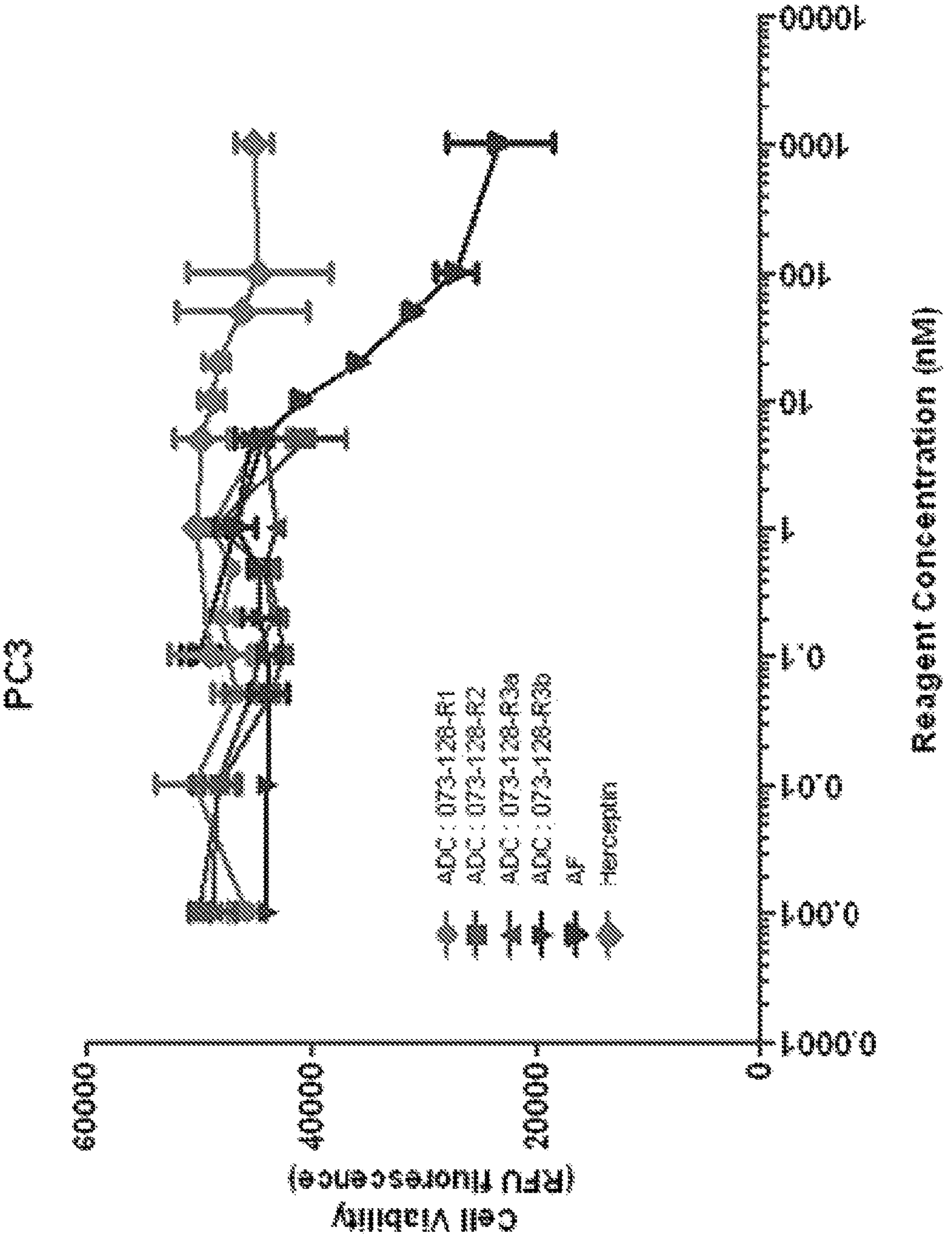

Compounds I-2, I-6, and I-9 were prepared on the DNA synthesizer as disclosed in the present disclosure. Compounds 1-2, 1-6, and I-9 were activated and conjugated to the commercial antibody Trastuzumab. As shown in FIGS. 1-2, compound I-2 ADC (labeled as "ADC: 073-128-R3a") was more potent and cytotoxic than other ADCs (I-9 ADC labeled as "ADC: 073-128-R1" and I-6 ADC labeled as ADC: 073-128-R2") and its component parts including Auristatin F alone (labeled as "AF") and Trastuzumab alone (labeled as "Herceptin"). Compound I-2 ADC was found to be potent and selective versus cell lines expressing the Her2 antigen. Compound I-2 ADC (labeled as "ADC: 073-128-R3a") and compound I-2 ADC (labeled as "ADC: 073-128-R3b") differ by average number of polymers attached per antibody (degree of labeling, DOL). ADC: 073-128-R3a has a DOL of 1.7 and ADC: 073-128-R3b has a DOL of 0.9.

All of the U.S. patents, U.S. patent application publications, U.S. patent applications, foreign patents, foreign patent applications and non-patent publications referred to in this specification and/or listed in the Application Data Sheet, including U.S. Provisional Patent Application No. 63/250,913, filed Sep. 30, 2021, and U.S. Provisional Patent Application No. 63/253,071, filed Oct. 6, 2021, are incorporated herein by reference, in their entirety to the extent not inconsistent with the present description. Aspects of the embodiments can be modified, if necessary to employ concepts of the various patents, applications and publications to provide yet further embodiments.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

The invention claimed is:

1. A compound having the following Structure (I):

(I)

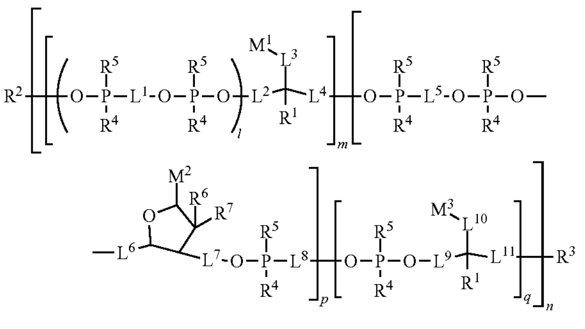

or a pharmaceutically acceptable salt, stereoisomer, or tautomer thereof, wherein $R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q, or a protected form thereof, or L';

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

$R^4$ is, at each occurrence, independently OH, SH, $O^-$, $S^-$, $OR_d$ or $SR_d$;

$R^5$ is, at each occurrence, independently oxo or thioxo;

$R^6$ and $R^7$ are, at each occurrence, independently H, OH, or halo, provided that at least one of $R^6$ or $R^7$ is halo;

$L^3$ and $L^{10}$ are, at each occurrence, independently a linker;

$L^1$, $L^2$, $L^4$, $L^5$, $L^6$, $L^7$, $L^8$, $L^9$, and $L^{11}$ are, at each occurrence, independently a direct bond or an optionally substituted linker;

$M^1$ is, at each occurrence, independently absent, or a moiety comprising a fluorescent dye;

$M^2$ is, at each occurrence, independently a chromophore;

$M^3$ is, at each occurrence, independently a moiety comprising an anticancer therapeutic;

Q is, at each occurrence, independently a moiety comprising a reactive group, or protected form thereof, capable of forming a covalent bond with a complementary reactive group Q' on a targeting moiety;

L' is, at each occurrence, independently a linker comprising a covalent bond to Q, a targeting moiety, a linker comprising a covalent bond to a targeting moiety, a linker comprising a covalent bond to a solid support, a linker comprising a covalent bond to a solid support residue, a solid support residue, a linker comprising a covalent bond to a nucleoside, or a linker comprising a covalent bond to a further compound of Structure (I);

l is, at each occurrence, independently an integer of one or greater;

m is, at each occurrence, independently an integer of zero or greater;

n is an integer of one or greater;

at least one occurrence of p is an integer of 1 or greater, and each remaining p is either 0 or an integer of 1 or greater; and q is, at each occurrence, independently an integer of zero or greater.

2. The compound of claim 1, wherein at least one occurrence of $L^1$, $L^5$, or $L^8$ is alkylene.

3. The compound of claim 1, wherein at least one occurrence of $L^1$, $L^5$, or $L^8$ is methylene.

4. The compound of claim 1, wherein at least one occurrence of $L^1$, $L^5$, or $L^8$ is heteroalkylene.

5. The compound of claim 1, wherein at least one occurrence of $L^1$, $L^5$, or $L^8$ comprises alkylene oxide.

6. The compound of claim 1, wherein the alkylene oxide is ethylene oxide.

7. The compound of claim 6, wherein the ethylene oxide is polyethylene oxide.

8. The compound of claim 1, wherein $R^2$ is L'.

9. The compound of claim 1, wherein L' is a linker to a targeting moiety.

10. The compound of claim 1, wherein L' is a linker to a targeting moiety, the linker comprising an alkylene oxide or phosphodiester moiety, or combinations thereof.

11. The compound of claim 1, wherein L' has one of the following structures:

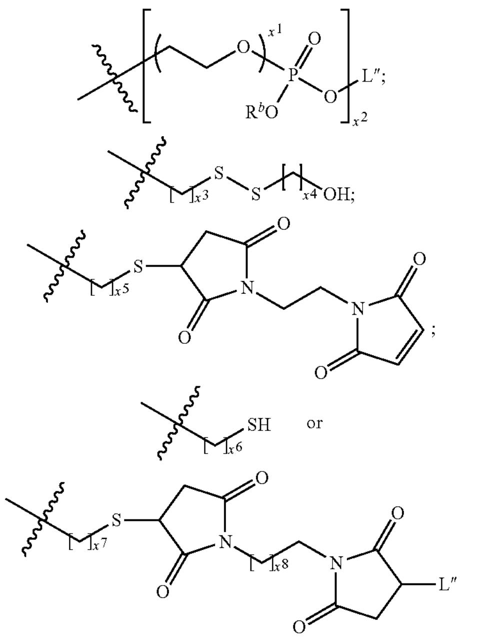

wherein:

$x^1$, $x^2$, $x^3$, $x^4$, $x^5$, $x^6$, $x^7$ and $x^8$ are independently an integer from 1 to 10;

$R_b$ is H, an electron pair or a counter ion; and

L" is the targeting moiety or a linkage to the targeting moiety.

12. The compound of claim 1, wherein the targeting moiety is an antibody or cell surface receptor antagonist.

13. The compound of claim 12, wherein the antibody or cell surface receptor antagonist is an epidermal growth factor receptor (EGFR) inhibitor, a hepatocyte growth factor receptor (HGFR) inhibitor, an insulin-like growth factor receptor (IGFR) inhibitor, a folate, or a MET inhibitor.

14. The compound of claim 1, wherein the targeting moiety is a monoclonal antibody.

15. The compound of claim 14, wherein the monoclonal antibody is Abciximab, Adalimumab, Alemtuzumab, Alirocumab, Avibactam, Basiliximab, Benralizumab, Bezlotoxumab, Blinatumomab, Brodalumab, Burosumab, Canakinumab, Caplacizumab, Certolizumab pegol, Daclizumab, Denosumab, Dupilumab, Eculizumab, Emicizumab, Erenumab, Evolocumab, Fremanezumab, Galcanezumab, Golimumab, Guselkumab, Ibalizumab, Idarucizumab, Infliximab, Itolizumab, Ixekizumab, Lanadelumab, Lokivetmab, Mepolizumab, Natalizumab, Obiltoxaximab, Ocrelizumab, Omalizumab, Palivizumab, Ranibizumab, Raxibacumab, Reslizumab, Rmab, Rovelizumab, Ruplizumab, Sarilumab, Secukinumab, Tildrakizumab, Thiomab, Tocilizumab, Ustekinumab, Vedolizumab, Abrilumab, Actoxumab, Aducanumab, Afasevikumab, Afelimomab, Anifrolumab, Anrukinzumab (IMA-638), Aselizumab, Atorolimumab, Bapineuzumab, BCD-100, Bertilimumab, Besilesomab, Biciromab, Bimagrumab, Bimekizumab, Birtamimab, Bleselumab, Blosozumab, Bococizumab, Brazikumab, Briakinumab, Brolucizumab, Carlumab, Carotuximab, Cedelizumab, Clazakizumab, Clenoliximab, Concizumab, Cosfroviximab, CR6261, Crenezumab, Crizanlizumab, Crotedumab, Depatuxizumab, mafodotin, Derlotuximab biotin, Dezamizumab, Diridavumab, Domagrozumab, Dusigitumab, Ecromeximab, Edobacomab, Efalizumab, Efungumab, Eldelumab, Elezanumab, Enokizumab, Eptinezumab, Erlizumab, Etrolizumab, Evinacumab, Exbivirumab, Fanolesomab, Faralimomab, Faricimab, Fasinumab, Felvizumab, Fezakinumab, Flanvotumab, Fletikumab, Flotetuzumab, Fontolizumab, Foravirumab, Frovocimab, Fulranumab, Gantenerumab, Gavilimomab, Gevokizumab, Gimsilumab, Gomiliximab, Gosuranemab, Ianalumab, Inclacumab, Inolimomab, Iomab-B, Keliximab, Lampalizumab, Landogrozumab, Larcaviximab, Lebrikizumab, Lenvervimab, Lerdelimumab, Letolizumab, Libivirumab, Ligelizumab, Lodelcizumab, Lulizumab pegol, Marstacimab, Mavrilimumab, Metelimumab, Mirikizumab, Motavizumab, Muromonab CD3, Nebacumab, Nemolizumab, NEOD001, Nirsevimab, Odulimomab, Olendalizumab, Olokizumab, OMS721, Opicinumab, Orticumab, Otelixizumab, Otilimab, Oxelumab, Ozanezumab, Ozoralizumab, Pagibaximab, Panobacumab, Pascolizumab, Pateclizumab, PDR001, Perakizumab, Pexelizumab, Placulumab, Plozalizumab, Ponezumab, Porgaviximab, Prasinezumab, Priliximab, PRO 140, Quilizumab, Rafivirumab, Ralpancizumab, Ranevetmab, Ravagalimab, Ravulizumab, Refanezumab, Regavirumab, Relatlimab, Rinucumab, Risankizumab, Roledumab, Romosozumab, Rontalizumab, SA237, Satralizumab, Sevirumab, SHP647, Sifalimumab, Simtuzumab, Siplizumab, Sirukumab, Solanezumab, Sonepcizumab, Spartalizumab, Stamulumab, Sulesomab, Suptavumab, Sutimlimab, Suvizumab, Suvratoxumab, Tadocizumab, Talizumab, Tamtuvetmab, Tanezumab, Tefibazumab, Telimomab aritox, Teneliximab, Teplizumab, Teprotumumab, Tezepelumab, Tibulizumab, Toralizumab, Tralokinumab, Trevogrumab, Tuvirumab, Ulocuplumab, Urtoxazumab, Varisacumab, Vepalimomab, Vesencumab, Visilizumab, Vobarilizumab, Zolimomab aritox, trastuzumab, gemtuzumab, brentuximab, vorsetuzumab, lorvotuzumab, cantuzumab, bivatuzumabor, inotuzumab, or vadastuximab.

16. The compound of claim 1, wherein $R^2$ or $R^3$ has one of the following structures:

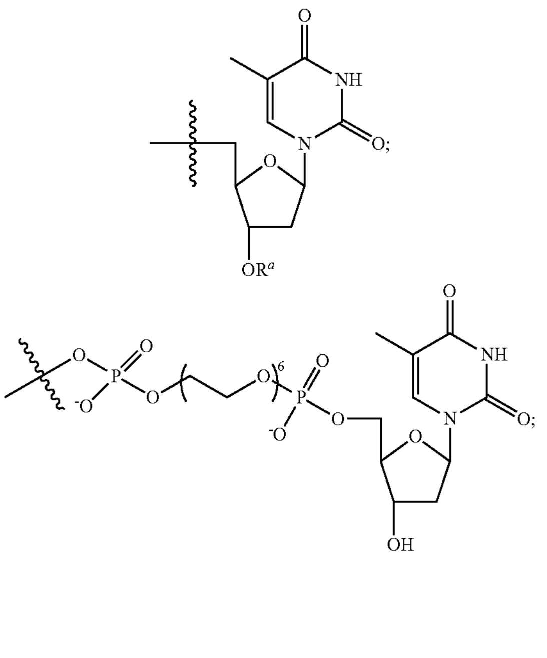

-continued
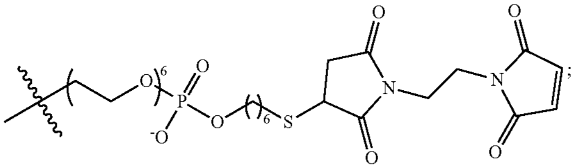
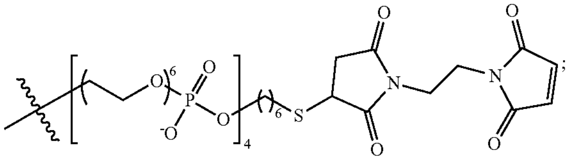
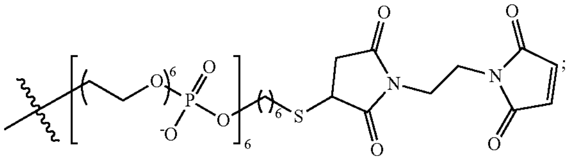
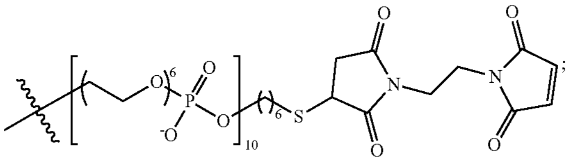
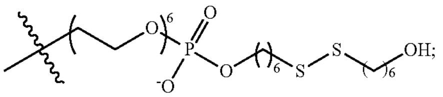
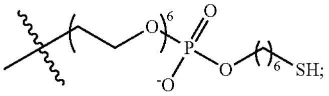
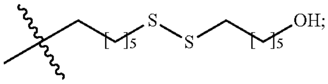
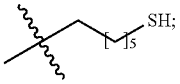
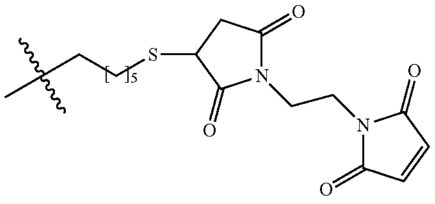
or
-continued
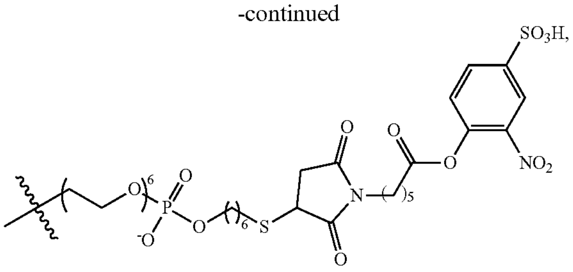
wherein
$R_a$ is H or a solid support.
17. The compound of claim 1, wherein $R^2$ has one of the following structures:
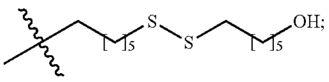
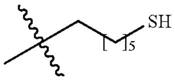
or
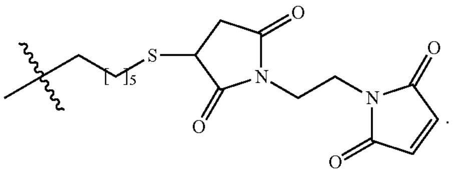
18. The compound of claim 1, wherein $R^3$ has the following structure:
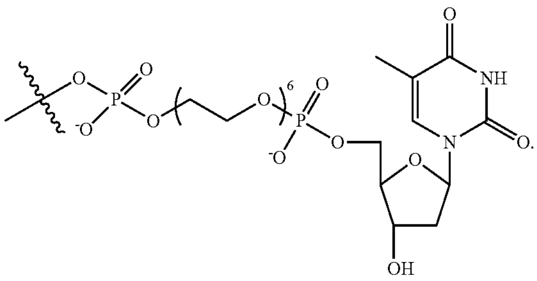
19. The compound of claim 1, wherein the compound has the following structure (Ia):
(Ia)
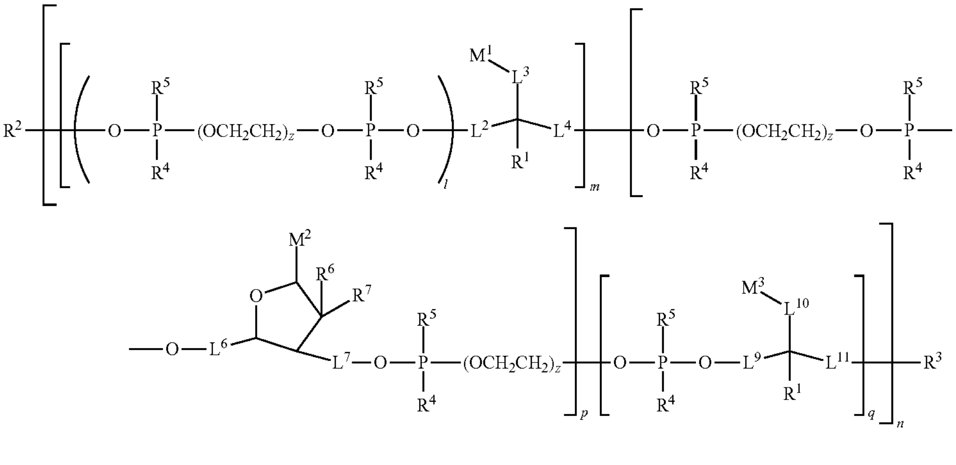

or a pharmaceutically acceptable salt, stereoisomer, or tautomer thereof, wherein z is, at each occurrence, independently an integer from 1 to 10.

20. The compound of claim 1, wherein $R^5$ is, at each occurrence, independently OH, $O^-$ or $OR_d$.

* * * * *